(12) United States Patent
Veerasamy

(10) Patent No.: US 7,504,957 B2
(45) Date of Patent: Mar. 17, 2009

(54) LIGHT SENSOR EMBEDDED ON PRINTED CIRCUIT BOARD

(75) Inventor: Vijayen S. Veerasamy, Ann Arbor, MI (US)

(73) Assignee: Guardian Industries Corp., Auburn Hills, MI (US)

(*) Notice: Subject to any disclaimer, the term of this patent is extended or adjusted under 35 U.S.C. 154(b) by 0 days.

(21) Appl. No.: 12/076,255

(22) Filed: Mar. 14, 2008

(65) Prior Publication Data

US 2008/0225395 A1 Sep. 18, 2008

Related U.S. Application Data

(63) Continuation-in-part of application No. 11/700,251, filed on Jan. 31, 2007, which is a continuation-in-part of application No. 11/340,869, filed on Jan. 27, 2006, which is a continuation-in-part of application No. 11/340,864, filed on Jan. 27, 2006, which is a continuation-in-part of application No. 11/340,859, filed on Jan. 27, 2006, which is a continuation-in-part of application No. 11/340,847, filed on Jan. 27, 2006.

(60) Provisional application No. 60/757,479, filed on Jan. 10, 2006.

(51) Int. Cl.
*G08B 21/00* (2006.01)

(52) U.S. Cl. .................. 340/602; 359/601; 362/459; 250/200

(58) Field of Classification Search .................. 340/602
See application file for complete search history.

(56) References Cited

U.S. PATENT DOCUMENTS 4,867,561 A * 9/1989 Fujii et al. ............... 356/239.8

| | | | |
|---|---|---|---|
| 6,105,461 A | 8/2000 | Bauer et al. | |
| 6,552,690 B2 | 4/2003 | Veerasamy | |
| 6,614,241 B2 | 9/2003 | Schmitt et al. | |
| 6,759,761 B1 * | 7/2004 | Schmitt et al. ............. | 307/10.8 |
| 6,809,530 B2 | 10/2004 | Schmitt et al. | |
| 6,861,636 B2 * | 3/2005 | Ockerse et al. ............. | 340/461 |

(Continued)

OTHER PUBLICATIONS

U.S. Appl. No. 11/700,251, filed Jan. 31, 2007.

(Continued)

*Primary Examiner*—Benjamin C Lee
*Assistant Examiner*—Samuel J Walk
(74) *Attorney, Agent, or Firm*—Nixon & Vanderhye P.C.

(57) ABSTRACT

A system and/or method for sensing the presence of moisture (e.g., rain) and/or other material(s) on a window such as a vehicle window (e.g., vehicle windshield, sunroof or backlite). Such techniques may be used in connection with a light sensor. In certain example embodiments, a flexible printed circuit board (PCB) includes a light sensor comprising a light sensor flip-chip, with the light sensor flip-chip including at least two light sensor arrays, and with each said sensor array being configured to sense light of a predetermined wavelength. An adhesive bonds the light sensor to the PCB. A hole is formed in the PCB and the opaque layer so as to allow the light sensor arrays to see through the hole formed in the PCB and the opaque layer. A state of the vehicle lights is settable in dependence on the light sensor. The PCB is located in or is supported by the vehicle windshield.

21 Claims, 41 Drawing Sheets

U.S. PATENT DOCUMENTS

| | | |
|---|---|---|
| 6,888,465 B2 | 5/2005 | Schmitt et al. |
| 7,156,168 B2 | 1/2007 | Gutbrod et al. |
| 7,198,402 B2 | 4/2007 | Ruettiger |
| 7,235,767 B2 | 6/2007 | Gutbrod et al. |
| 7,256,385 B2 | 8/2007 | Rüttiger et al. |
| 7,325,972 B2 | 2/2008 | Ruettiger |
| 7,331,531 B2 | 2/2008 | Rüttiger et al. |
| 2007/0157720 A1 | 7/2007 | Veerasamy |
| 2007/0157721 A1 | 7/2007 | Veerasamy |
| 2007/0157722 A1 | 7/2007 | Veerasamy |
| 2007/0162201 A1 | 7/2007 | Veerasamy |
| 2007/0200718 A1 | 8/2007 | Veerasamy |

OTHER PUBLICATIONS

U.S. Appl. No. 11/340,847, filed Jan. 27, 2006.
U.S. Appl. No. 11/340,864, filed Jan. 27, 2006.
U.S. Appl. No. 11/340,859, filed Jan. 27, 2006.
U.S. Appl. No. 11/340,869, filed Jan. 27, 2006.
U.S. Appl. No. 60/757,479, filed Jan. 10, 2006.
U.S. Appl. No. 12/076,239, filed Mar. 14, 2008 (Veerasamy).
U.S. Appl. No. 12/076,238, filed Mar. 14, 2008 (Veerasamy).

* cited by examiner

Outer line width = 2mm
Inner line width = 1mm
Air gap = 0.6mm

All units are in mm

Inner circle diameter = 6mm
Outer circle diameter = 13mm
Distance between contact pads = 1mm

|   | C1 | C2 | C3 | C4 |
|---|----|----|----|----|
| C1 | H | L | H | H |
| C2 | L | H | H | H |
| C3 | H | H | H | L |
| C4 | H | H | L | H |

*Fig. 12B*

|   | C1 | C2 | C3 | C4 |
|---|----|----|----|----|
| C1 | H | L | H | H |
| C2 | L | H | H | H |
| C3 | H | H | H | L |
| C4 | H | H | L | H |

*Fig. 12A*

Autocorrelation Example

|  | $-t_2$ | $-t_1$ | $t=0$ | $t_1$ | $t_2$ | $t_3$ |  |
|---|---|---|---|---|---|---|---|
| C1 | 0 | 0 | 1 | 1 | 0 | 0 | |
| × C1 | 0 | 0 | 1 | 1 | 0 | 0 | |
| $ac_0 =$ | 0 + | 0 + | 1 + | 1 + | 0 + | 0 | = 2 [Sum] |
| | | | | | | | |
| × | 0 | 0 | 0 | 1 | 0 | 0 | |
| | 0 | 0 | 1 | 1 | 0 | 0 | |
| $ac_1 =$ | 0 | 0 | 0 | 1 | 0 | 0 | = 1 [Sum] |

|  | Signal | Delta |
|---|---|---|
| No-Disturbance @ 65 F | N1 | 0 |
|  | N2 | 0.8 |
|  | N3 | 0.3 |
|  | N4 | 0.7 |
|  | N5 | 0.3 |
|  |  |  |
|  |  |  |
| on target water @ 65 F | S1 | 6 |
|  | S2 | 55 |
|  | S3 | 52 |
|  | S4 | 63 |
|  | S5 | 60 |
|  |  |  |
|  |  |  |
| off target water @ 65 F | F1 | 1 |
|  | F2 | 0.3 |
|  | F3 | 5 |
|  | F4 | 3 |
|  | F5 | 0.6 |
|  |  |  |
|  |  |  |
| no-disturbance @ 130 F | H1 | 0.3 |
|  | H2 | 0.5 |
|  | H3 | 0.4 |
|  | H4 | 0.7 |
|  |  |  |
|  |  |  |
| on target water @ 130 F | W1 | 61 |
|  | W2 | 49 |
|  | W3 | 66 |
|  | W4 | 19 |
|  | W5 | 64 |
|  |  |  |
|  |  |  |
| off target water @ 130 F | K1 | 6 |
|  | K2 | 24 |
|  | K3 | 4.8 |
|  | K4 | 4 |
|  | K5 | 2 |

*Fig. 14*

*Note:* Delta = difference computed between each signal's normalized autocorrelation datapoint and the normalized autocorrelation of a reference (no-disturbance)

1. (S1 & S3)

2. (S2 & S4)

3. (S3 & S2)

4. (S1, S5)

5. (S4 & S1)

1. (W1 & W2)

4. (W4 & W1)

5. (W4 & W5)

2. (W3 & W4)

3. (W2, W5)

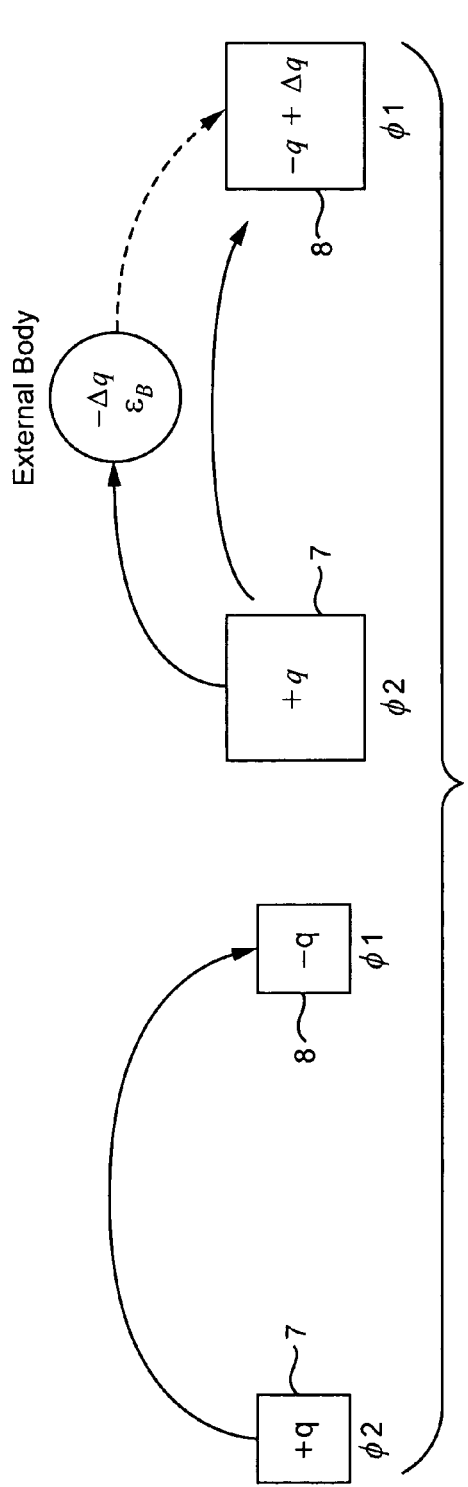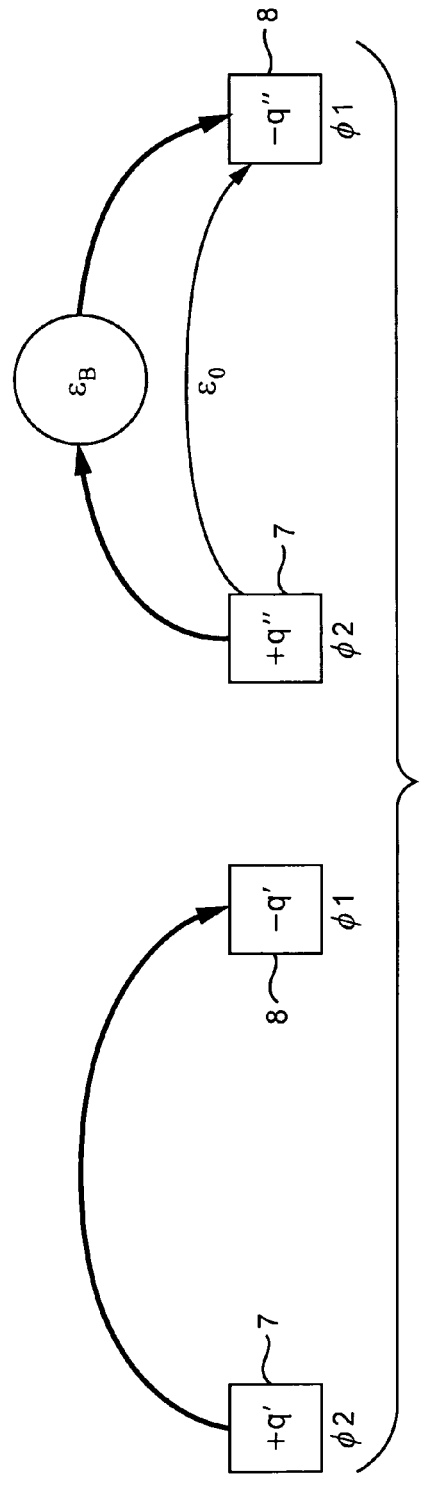
Fig. 28A
Fig. 28B

LIGHT SENSOR EMBEDDED ON PRINTED CIRCUIT BOARD

CROSS-REFERENCES TO RELATED APPLICATIONS

This application is a continuation-in-part (CIP) of U.S. Ser. No. 11/700,251, filed Jan. 31, 2007, which is a CIP of each of U.S. Ser. No. 11/340,847, filed Jan. 27, 2006, Ser. No. 11/340,864, filed Jan. 27, 2006, Ser. No. 11/340,859, filed Jan. 27, 2006, and Ser. No. 11/340,869, filed Jan. 27, 2006, all of which claim priority on U.S. Provisional Patent Application No. 60/757,479, filed Jan. 10, 2006, the disclosures of which are all hereby incorporated herein by reference.

FIELD OF THE INVENTION

This invention relates to a system and/or method for sensing the presence of rain and/or the disturbances or presence of other materials on a sheet(s) of glass such as a vehicle windshield, backlite, or sunroof. Such techniques may be used in connection with a light sensor. In certain example embodiments, a flexible printed circuit board (PCB) includes a light sensor comprising a light sensor flip-chip, with the light sensor flip-chip including at least two light sensor arrays, and with each said sensor array being configured to sense light of a predetermined wavelength. An adhesive bonds the light sensor to the PCB. A hole is formed in the PCB and the opaque layer so as to allow the light sensor arrays to see through the hole formed in the PCB and the opaque layer. A state of the vehicle lights is settable in dependence on the light sensor. The PCB is located in or is supported by the vehicle windshield.

BACKGROUND AND SUMMARY OF EXAMPLE EMBODIMENTS OF THE INVENTION

The presence of moisture (e.g., rain or condensation) and/or other material or debris on vehicle windshields and/or backlites may create hazardous driving conditions for drivers, passengers, and pedestrians if not promptly removed. Wiper blades are a well-known, common way to remove such materials and reduce the hazards of driving during dangerous conditions. Rain sensors have been developed to detect the presence of moisture (e.g., rain or other condensation) on a vehicle windshield, and to turn on and off wipers, as necessary, when such moisture is detected. Automatically detecting rain, sleet, fog, and the like, and taking appropriate action—for example, turning on/off wiper blades at a proper speed—potentially reduces distractions to the driver, allowing the driver to better concentrate on the road ahead. However, inappropriately turning on/off wipers or failing to actuate wipers when moisture is present may also create hazardous conditions. Moreover, such systems are also susceptible to "dirt" distractions which may cause false reads/wipes when dirt is on the windshield.

Certain conventional rain sensors are based on an electro-optical concept. According to certain such techniques, rain droplets are sensed solely by measuring the change in the total internal reflection of a light beam off the glass-air interface. Other electro-optical techniques have attempted to analyze the brightness of a section of a window "image" to detect rain droplets or fog on a window. However, these optical techniques have limited sensing areas, are fairly expensive, and may result in erroneous detection indications due to the use of optical imaging as the sole detection method.

Thus, it will be appreciated that there exists a need in the art for a moisture (e.g., rain) sensor that is efficient in operation and/or detection.

In certain example embodiments of this invention, a plurality of sensing capacitors are supported by a window such as a vehicle windshield, the capacitors each having a different field. A sensing circuit outputs an analog signal that is based on and/or related to the capacitances of the sensing capacitors. In certain example embodiments, a switching circuit is provided in order to selectively switch between different sensing capacitors or different combinations thereof (or even possibly antennas and/or bands), in order to change the sensing field being analyzed and/or change the feature being searched for. For example, in certain example embodiments, the switching circuit may selectively switch between: (a) capacitor(s) for detecting rain on an exterior surface of the window, and (b) capacitor(s) for detecting one or more of ice on an exterior surface of the window, mist on an exterior surface of the window, and/or moisture on an interior surface of the window. Such embodiments may or may not be used in combination with any other embodiment(s) of this invention discussed herein.

In certain example embodiments of this invention, there is provided a rain sensor comprising: a sensing circuit comprising a plurality of sensing capacitors supported by a vehicle window, one or more of the sensing capacitors being sensitive to moisture on an external surface of the window and including first and second spaced apart capacitor electrodes that are substantially coplanar; and a switching circuit for selectively coupling the plurality of sensing capacitors to read-out circuitry of the rain sensor.

In other example embodiments of this invention, there is provided an electronic device (e.g., rain sensor, antenna system, or the like) comprising: a sensing circuit comprising a plurality of different fractal structures, and a switching circuit for selectively coupling different ones or combinations of the fractal structures to read-out circuitry. The fractal structures may be capacitive sensors, antennas having different bands, or the like in different example instances.

In certain example embodiments of this invention, there is provided a rain sensor comprising: a sensing circuit comprising at least one sensing capacitor that is sensitive to moisture on an external surface of a window; an adder receiving, directly or indirectly, an analog output signal from the sensing circuit and determining a difference between the analog output signal from the sensing circuit and a feedback signal; a quantizer including a comparator downstream of the adder that outputs a bitstream based at least on whether a received signal level is higher or lower than a predetermined threshold; a lowpass digital filter downstream of the quantizer for lowpass filtering the bitstream so as to output a filtered digital signal; and a correlation engine that performs correlation on the filtered digital signal in order to determine whether rain is present on the external surface of the window. In certain example instances, this system may be said to use sigma-delta modulation in analog to digital signal conversion.

In certain example embodiments of this invention, there is provided a method of determining whether moisture is present on an external surface of a vehicle window, the method comprising: receiving a signal relating to at least one sensing capacitor, and processing the signal to obtain a signal footprint; and comparing the signal footprint with one or more predetermined signal footprints stored in memory to determine whether a detected material on the external surface of the vehicle is moisture or some other material.

In certain example embodiments of this invention, there is provided a rain sensor comprising: at least one sensing capacitor supported by a window, the sensing capacitor being sensitive to rain on an external surface of the window; and wherein the sensing capacitor comprises fractal geometry.

In certain example embodiments of this invention, there is provided a rain sensor comprising: at least one sensing capacitor that is sensitive to moisture on an external surface of a window; and the first sensing capacitor comprising first and second capacitor electrodes each have a meandering shape, and wherein the first and second capacitor electrodes are substantially parallel to each other.

In certain example embodiments of this invention, there is provided a rain sensor comprising: a sensing circuit comprising at least first and second sensing capacitors that are sensitive to moisture on an external surface of a window; the sensing circuit further comprising at least one mimicking capacitor that mimics at least charging and/or discharging of at least one of the first and second sensing capacitors; wherein a writing pulse causes at least the first sensing capacitor to be charged, and an erasing pulse causes each of the first sensing capacitor and the mimicking capacitor to substantially discharge; wherein presence of rain on the external surface of the window in a sensing field of the first sensing capacitor causes a voltage at an output electrode of the mimicking capacitor to fluctuate in a manner proportional to fluctuation of voltage at an output electrode of the first sensing capacitor, even though the rain is not present in a field of the mimicking capacitor; and wherein rain is detected based on an output signal from the output electrode of the mimicking capacitor, wherein the output signal is read at least between an end of the writing pulse and a beginning of the erase pulse.

In other example embodiments of this invention, there is provided a method of detecting rain on a surface of a window, the method comprising: supplying first and second spaced apart writing pulses which respectively cause first and second sensing capacitors of a sensing circuit to charge, wherein the first sensing capacitor charges when the second sensing capacitor is substantially discharged, and the second sensing capacitor charges when the first sensing capacitor is substantially discharged, so that the first and second sensing capacitors are charged at different times; each of the first and second sensing capacitors being sensitive to moisture on the surface of the window; supplying a first erasing pulse, between times of the first and second writing pulses, the first erasing pulse causing the first sensing capacitor to substantially discharge, and supplying a second erasing pulse after the second writing pulse wherein the second erasing pulse causes the second sensing capacitor to substantially discharge; wherein a magnitude of an output of the sensing circuit is affected by presence of rain on the surface of the window; and converting an analog output signal of the sensing circuit to a digital signal and based on the digital signal determining whether rain is present on the surface of the window.

In certain example embodiments of this invention, there is provided a rain sensor comprising: at least one sensing capacitor that is sensitive to moisture on an external surface of a window, the sensing capacitor including a first capacitor electrode that receives a charging signal and a second capacitor electrode spaced apart from the first capacitor electrode; and wherein the second capacitor electrode is floating so that the sensing capacitor is isolated from ground. The floating characteristic has been found to be advantageous in that it permits false reads due to EMI or external objects (e.g., human hand) to be reduced or prevented.

In certain example embodiments of this invention, there is provided a method of sensing the presence of moisture (e.g., rain, dew, fog, or the like) on a vehicle window, the method comprising: receiving data relating to at least two capacitors supported by the vehicle window; autocorrelating the data relating to each capacitor to obtain autocorrelated data; and determining, based at least on said autocorrelated data, whether moisture is present on an exterior surface of the vehicle window. In certain example embodiments, the data relating to the at least two capacitors is received from circuitry that receives and/or reads capacitance data from the at least two capacitors. In certain example embodiments, the data relating to the at least two capacitors is output from circuitry that: (a) receives and/or reads data and/or signals from the at least two capacitors, and/or (b) includes a capacitor(s) or other circuit element(s) that mimics or substantially mimics charging and/or discharging of the at least two capacitors. In certain example embodiments, the autocorrelation may be used as an initial step to determine whether water may be present on the window. However, it is possible that the autocorrelation may also detect the presence of other materials (e.g., dust or dirt) on the window because the correlation signatures of these materials can be different.

In certain example embodiments of this invention, there is provided a moisture sensor (e.g., rain sensor) for sensing the presence of moisture on a vehicle window, the moisture sensor comprising: one, two or more capacitors; means for autocorrelating data from one, two, three, more, or all of the capacitors to obtain autocorrelated data; and means for determining, based at least on said autocorrelated data, whether moisture is present on the vehicle window.

In certain example embodiments of this invention, cross-correlating data from the at least two capacitors may be performed so as to correlate data from different capacitors to obtain cross-correlated data. Then, based at least on the cross-correlated data, a type and/or amount of moisture may be determined. The cross-correlated data may also or instead be used to determine if the material detected via the autocorrelation is a material other than moisture such as dust or dirt, and if so then not actuating the wipers. In certain example embodiments, the cross-correlating may be performed after the autocorrelating when certain conditions are met. As an example, the cross-correlation may be performed so as to determine whether the moisture on the window is light rain, heavy rain, fog, sleet, snow, or ice (a type of moisture).

In certain example embodiments of this invention, the autocorrelated data from the capacitor(s) may be checked for negative values. When the autocorrelated data has negative value(s), then the system or method may indicate that it is not raining and/or may not actuate windshield wipers.

Moreover, in certain example embodiments, the system or method may calculate whether a gradient of an autocorrelation curve associated with the autocorrelated data is greater than one or some other predetermined value; and if not then the system or method may indicate that it is not raining, park the wipers if they were moving, and/or not actuate wipers of the vehicle.

In certain example embodiments of this invention, the system or method may determine whether the shape of the autocorrelation curve or signal footprint associated with the autocorrelated data is different than a predetermined autocorrelation curve or signal footprint associated with normalized non-disturbed autocorrelation data. When it is not different or substantially different, then it may be indicated that it is not raining, wipers may be parked if they had been moving, and/or wipers may be not actuated. While the footprints are based on autocorrelation data in certain example embodiments of this invention, other types of footprints may instead be used in certain instances.

In certain example embodiments of this invention, conditions checked for in the autocorrelation function include (i)

the gradient of the normalized autocorrelation function (e.g., when there is no disturbance the absolute value of the gradient is unity and changes with disturbance), (ii) the sign of the autocorrelation function (e.g., with a CB radio turned on or with a human hand on the windshield the values are oscillatory with positive and negative parts), and (iii) the shape of the autocorrelation function as a function of time lag may also be used as a signature or footprint to distinguish rain from other disturbances, and this shape may also be used to distinguish between different nuances of rain or water content. Thus, in certain example instances, cross-correlating of data from at least two capacitors is only performed when one, two or all of the following conditions are met: (a) the autocorrelated data has no negative values; (b) a gradient of an autocorrelation curve associated with said autocorrelated data is greater than one; and (c) the shape of the autocorrelation curve associated with the autocorrelated data (e.g., signal footprint) is different than a predetermined autocorrelation curve associated with normalized non-disturbed autocorrelation data (e.g., predetermined footprint). Alternatively, (c) may be replaced with (c') the shape of the autocorrelation curve associated with the autocorrelated data (e.g., signal footprint) matches or substantially matches a predetermined autocorrelation curve (e.g., predetermined signal footprint) associated with a known moisture pattern. In certain example embodiments of this invention, a symmetry level of a cross-correlation curve associated with the cross-correlated data can be determined.

In certain example embodiments of this invention, it is possible to compare the autocorrelation between various capacitors. In certain example embodiments of this invention, such a comparison may be used to tell the system whether to initiate a wipe if water is present on the window when the sensor system is turned on.

In certain example embodiments, a sensing capacitor array may include at least n sensing capacitors, wherein n may be two, four, ten or any other suitable number. The array may be any type of array such as a linear array, any of the arrays shown in the figures, or any other type of array. Autocorrelating of data from and/or related to all or less than all of the sensing capacitors may be performed to obtain the autocorrelated data.

In certain example embodiments of this invention, capacitors are formed based on a fractal pattern. For example and without limitation, one or more of the capacitors may be formed based on a fractal pattern, such as a Hilbert fractal pattern. Other capacitive fractal patterns may also be used, including but not limited to a Cantor set. These fractal structures maximize or enlarge the periphery and thus result in a large capacitance for a given area. The use of two dimensional fractal designs also allows the sensor to occupy a small amount of physical space on the window while at the same time being electrically larger than its physical size. The concentration of lateral flux in a fractal geometry may also allow the sensor to detect rain/water not necessarily spread over the actual physical area of the sensor in certain example embodiments of this invention. Furthermore, in its higher iteration(s) a fractal capacitor(s) has an attribute of being its own Faraday shield or quasi-Faraday shield. Also, in certain example embodiments, the rain sensor may be electrically connected to a Local Interconnect Bus of the vehicle.

In certain example embodiments of this invention, there is provided a method of sensing the presence of moisture on a vehicle window such as a windshield, backlite or sunroof, the method comprising: receiving data from at least two capacitors supported by the vehicle window; correlating data from one or more of the capacitors to obtain correlated data; determining, based at least on said correlated data, (a) whether moisture is present on an exterior surface of the vehicle window, and/or (b) a type and/or amount of material present on an exterior surface of the vehicle window. For example and without limitation, the correlation may be autocorrelation and/or cross-correlation.

In certain example embodiments of this invention, there is provided a method of engaging vehicle windshield wiper(s) in response to detected rain, the method comprising reading data from a capacitive array having at least two capacitors; autocorrelating data from each capacitor individually; determining from the autocorrelation data whether it is raining; cross-correlating data from the capacitors; determining from the cross-correlated data a type and/or an amount of rain; engaging the wipers if rain is detected; and, stopping or not actuating the wipers if one or both of the determining steps determines that it is not raining. In certain example embodiments, a symmetry level of the cross-correlation curve may be determined, and a wiper speed related to the symmetry level may be selected. A wiper speed may be selected from a plurality of predetermined wiper speeds in certain example instances. In some example embodiments, only a single wipe is initiated for boundary conditions detected in one or both of the determining steps.

In certain example embodiments of this invention, there is provided a method of engaging windshield wipers of a vehicle in response to detected rain, the method comprising reading data from a capacitive array having at least two capacitors; mathematically comparing data from each capacitor individually (e.g., autocorrelating); determining from the mathematically compared individual capacitor data whether it is raining; mathematically comparing data from different capacitors (e.g., cross-correlating); determining from the mathematically compared different capacitor data a type and/or an amount of rain; engaging the wipers if rain is detected; and, stopping or not actuating the wipers if one or both of the determining steps determines that it is not raining.

In certain example embodiments, a sigma-delta modulator or other suitable circuit or software may be used to perform an analog-to-digital (A/D) conversion of data from the capacitive array. Additionally, in certain example embodiments, a software or other type of comparator may perform at least one of checking autocorrelation data for negative values, calculating whether a gradient of autocorrelation data is greater than one, and/or attempting to match or substantially match a shape of autocorrelation data with autocorrelation data stored in a database. In certain instances, the correlating engine computes cross-correlations when all conditions tested for by the comparator are met.

In certain example embodiments of this invention, there is provided a system or method for engaging windshield wipers in response to detected rain, the system (or method) comprising a capacitive array having at least two capacitors; circuitry that reads capacitance data from the capacitive array; a correlating engine or correlator that autocorrelates data from the circuitry to determine the existence of rain, and cross-correlates data from the circuitry to determine a type and/or an amount of rain if it is determined that rain exists; and, a wiper motor that is capable of receiving a signal for directing whether the wipers should move or stop. In certain example embodiments, a symmetry level of a cross-correlation curve is computed, and the wiper motor may select a wiper speed related to the symmetry level.

In certain example embodiments, a rain sensor comprises at least two sensing devices (e.g., sensing capacitors or the like) that are affected by rain on a surface of a window; circuitry that provides an output related to the sensing devices; and at least one correlating engine that (a) autocorrelates information from said circuitry to determine whether rain is present, and/or (b) cross-correlates information from said circuitry to determine how fast to operate at least one wiper of a vehicle and/or an amount of rain.

In certain example embodiments, a method or system for engaging window wiper(s) in response to detected rain is provided and comprises a capacitive array having at least two capacitors; circuitry that reads capacitance data from the capacitive array; an algorithm that mathematically determines existence of rain on the window based on data from the circuitry, and mathematically quantifies a type and/or amount of rain if it is determined that rain exists; and, a wiper motor capable of receiving a signal(s) directing whether the wiper(s) should move or stop.

In certain example embodiments, a rain sensor for a vehicle is provided. A printed circuit board (PCB) supported by a vehicle window comprises first and second outer layers and at least one inner layer. The first outer layer is closest to an interior of the vehicle, and the second outer layer is closest to an exterior of the vehicle. First and second capacitor arrays are provided. The first capacitor array is formed on an outer surface of the first outer layer of the PCB, and the second capacitor array is formed on an outer surface of the second outer layer of the PCB. One or more sensing capacitors in the first and/or second capacitor arrays is/are sensitive to moisture on an external surface of the window. Programmed logic circuitry is configured to distinguish between moisture on the exterior surface of the vehicle window, humidity on the interior surface of the vehicle window, and EMI. The at least one inner layer is arranged so as to decouple the first and second capacitor arrays and to shield the first capacitor array from fields emanating from the second capacitor array and vice versa. EMI is detected when the first and second capacitor arrays detect identical or similar signals substantially simultaneously.

In certain example embodiments, a flexible printed circuit board (PCB) supported by a vehicle window is provided. A first outer layer is provided, with the first outer layer being closest to an interior of the vehicle and being formed from a flexible polymer. A second outer layer is provided, with the second outer layer being closest to an exterior of the vehicle and being formed from a flexible polymer. A first capacitor array comprising a first plurality of sensing capacitors is printed or etched on the first outer layer of the PCB. A second capacitor array comprising a second plurality of sensing capacitors is printed or etched on the second outer layer of the PCB closest to the vehicle window. Programmed logic circuitry is configured to distinguish between moisture on the exterior surface of the vehicle window, humidity on the interior surface of the vehicle window, and EMI, in dependence on signals generated by the first and second capacitor arrays. At least one substantially metallic inner layer is arranged so as to decouple the first and second capacitor arrays and to shield the first capacitor array from fields emanating from the second capacitor array and vice versa. The first and second capacitor arrays are formed on opposing surfaces of the flexible PCB. EMI is detected when the first and second capacitor arrays detect identical or similar signals substantially simultaneously.

In certain example embodiments, an electronic device mountable in or on a vehicle window is provided. A flexible printed circuit board (PCB) is provided. First and second sensing circuits are formed on opposing sides of the flexible PCB, with each said sensing circuit comprising a plurality of different fractal structures. A ground plane is located between the first and second sensing circuits, with the ground plane being arranged so as to decouple the first and second capacitor arrays and to shield the first capacitor array from fields emanating from the second capacitor array and vice versa. The electronic device is configured to detect moisture on an exterior surface of the vehicle window, humidity on an interior surface of the vehicle window, and EMI.

In certain example embodiments, a light sensor for a vehicle is provided. A printed circuit board (PCB) supported by a vehicle window comprises first and second outer layers and at least one inner layer, with the first outer layer being closest to an interior of the vehicle and the second outer layer being closest to an exterior of the vehicle. A light sensor flip-chip is mounted to an inner surface of the first outer layer of the PCB, with the light sensor flip-chip including at least two light sensor arrays, and with each said sensor array being configured to sense light of a predetermined wavelength. Programmed logic circuitry is configured to set a state of the vehicle lights in dependence on the light sensor. The at least two light sensor arrays are arranged so as to see through a hole formed in the PCB, the hole in the PCB acting as a lens.

In certain example embodiments, a flexible printed circuit board (PCB) supported by a vehicle window is provided. A first outer layer is provided, with the first outer layer being closest to an interior of the vehicle and being formed from a flexible polymer. A second outer layer is provided, with the second outer layer being closest to an exterior of the vehicle and being formed from a flexible polymer. At least one substantially metallic inner layer is provided. A light sensor comprising a light sensor flip-chip is mounted to an inner surface of the first outer layer of the PCB, with the light sensor flip-chip including at least two light sensor arrays, and with each said sensor array being configured to sense light of a predetermined wavelength. Programmed logic circuitry is configured to set a state of the vehicle lights in dependence on the light sensor. The at least two light sensor arrays are arranged so as to see through a hole formed in the PCB, the hole in the PCB acting as a lens.

In certain example embodiments, a vehicle window is provided. First and second substantially parallel spaced-apart glass substrates are laminated together via a polymer-inclusive layer. An opaque layer is provided. A printed circuit board (PCB) includes a light sensor comprising a light sensor flip-chip, the light sensor flip-chip including at least two light sensor arrays, each said sensor array being configured to sense light of a predetermined wavelength. An adhesive bonds the light sensor to the PCB. A hole is formed in the PCB and the opaque layer so as to allow the light sensor arrays to see through the hole formed in the PCB and the opaque layer. A state of the vehicle lights is settable in dependence on the light sensor. The PCB is located in or is supported by the vehicle windshield.

BRIEF DESCRIPTION OF THE DRAWINGS

These and other features and advantages will be better and more completely understood by reference to the following detailed description of exemplary illustrative embodiments in conjunction with the drawings, of which:

FIG. 1(*e*) is a cross sectional view of a rain sensor according to another example embodiment of this invention, that may use the features of FIG. 1(*a*) and/or one or more of FIGS. 2-12.

FIG. 1(*f*) is a cross sectional view of a rain sensor according to another example embodiment of this invention, that may use the features of FIG. 1(*a*) and/or one or more of FIGS. 2-12.

FIG. 12A is an exemplary correlation matrix indicative of light rain.

FIG. 12B is an exemplary correlation matrix indicative of heavy rain.

FIG. 14 is a chart setting forth example cross-correlation data from capacitors C1, C2 according to examples of certain embodiments of this invention.

FIGS. 28(*a*) AND 28(*b*) are schematic diagrams illustrating advantages of using floating electrodes for sensing capacitors (e.g., C1-C4) according to certain example embodiments of this invention.

FIG. 31 illustrates a switching circuit which may be used in conjunction with any of the other embodiments of this invention, so as to selectively switch between different sensing capacitors in order to change the sensing field being analyzed and/or change the feature being searched for.

DETAILED DESCRIPTION OF EXAMPLE EMBODIMENTS OF THE INVENTION

Figure 1A:
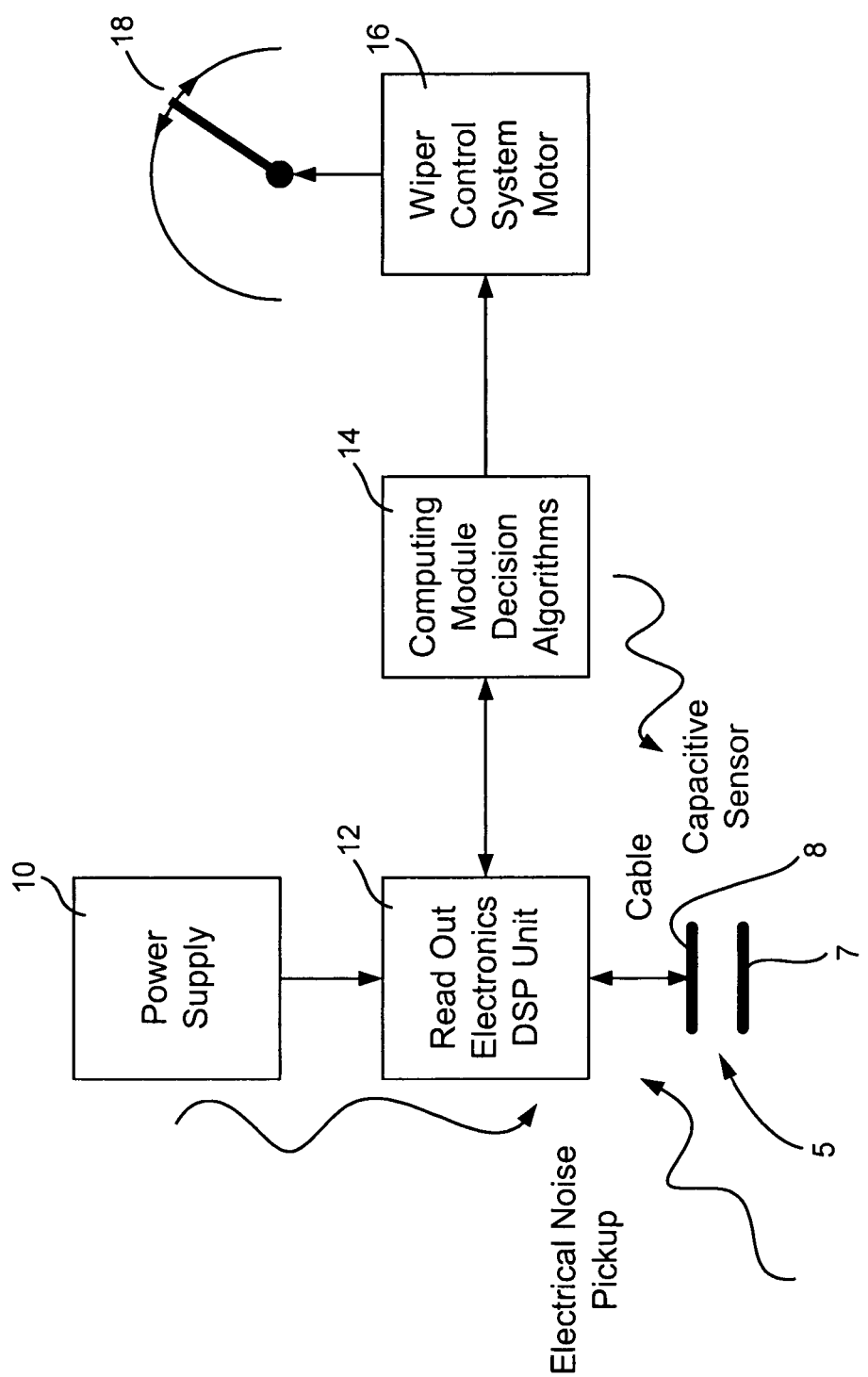
FIG. 1(a) is a block diagram of components of an exemplary rain sensor according to an example embodiment of this invention.

Referring now more particularly to the accompanying drawings in which like reference numerals indicate like parts throughout the several views.

In certain example embodiments of this invention, a moisture (e.g., rain) sensor system and/or method is provided and includes capacitance-based detection which translates a physical input signal (e.g., the presence of a drop of water on a windshield, or the like) into a digital electrical voltage signal which is received and interpreted by a software program(s) or circuit(s) that decides whether windshield wipers should be activated, and, if so, optionally their proper speed. Thus, capacitive coupling is used to detect water and/or other material in the exterior surface of a window such as a vehicle windshield, sunroof, and/or backlite. It will be appreciated that computational methods may be performed by hardware or a combination of hardware and software in different example embodiments of this invention. In certain example embodiments of this invention, no reference capacitance or capacitor is needed (i.e., no compensation capacitor is needed).

In certain example embodiments of this invention, a plurality of sensing capacitors are supported by a window such as a vehicle windshield, the capacitors each having a different field. A sensing circuit outputs an analog signal that is based on and/or related to the capacitances of the sensing capacitors. In certain example embodiments, a switching circuit is provided in order to selectively switch between different sensing capacitors or different combinations thereof (or even possibly antennas and/or bands), in order to change the sensing field being analyzed and/or change the feature being searched for (e.g., see FIGS. 4, 5, 26 and 31). For example, in certain example embodiments, the switching circuit may selectively switch between: (a) capacitor(s) for detecting rain on an exterior surface of the window, and (b) capacitor(s) for detecting one or more of ice on an exterior surface of the window, mist on an exterior surface of the window, and/or moisture on an interior surface of the window. Such embodiments may or may not be used in combination with any other embodiment(s) of this invention discussed herein.

Certain example embodiments of this invention take advantage of a permittivity equation, which gives a physical quantity that describes how an electric field affects and is affected by a medium. An example basic permittivity equation is:

$$D = \epsilon_0 E + P,$$

where D is electrical flux, $\epsilon_0$ is the dielectric constant of a vacuum, E is an electrical field (e.g., the voltage setup between plates or electrodes divided by distance, or V/m), and P is polarization. Polarization P can be further described mathematically as:

$$P = \epsilon_r \epsilon_0 E,$$

where $\epsilon_r$ is relative permittivity (e.g., the dielectric constant of water, ice, dirt or anything else that could be on an exterior surface of a window such as a windshield). In general, a high value of $\epsilon_i$ will correspond to high polarizability. The permittivity of glass is approximately 8, and the permittivity of water is approximately 85. By substitution and factorization, then, the permittivity equation can be rewritten as:

$$D = \epsilon_0(\epsilon_r + 1)E.$$

In this form, it will be appreciated that D is the response to excitation E.

Capacitance C is given by C=Q/V, where Q is the charge and V is the potential, in volts. Additionally, C=Φ/V, where Φ is the electric flux associated with charge Q. By Gauss' Law:

$$\Phi = \oint E \cdot dA,$$

where dA is the area of a differential square on the closed surface S. By substitution, then, it becomes clear that capacitance is related to potential difference:

$$C = \int D \, dA / V.$$

These equations form the basis of an example technique for measuring the interaction of water on glass by using a sensor with a capacitive array to probe above the window (e.g., glass). In particular, data from a sensor including at least one, or two or more, capacitor(s) (e.g., C1, C2, C3, etc.) may be used to detect whether moisture (e.g., rain, or the like) is present on an exterior surface of a window such as a vehicle windshield or backlite. The above equations illustrate that the presence of water on the surface of a window can affect the capacitance of an appropriately positioned sensing capacitor.

FIG. 1(a) is a block diagram of example components of a moisture (e.g., rain) sensor according to an example embodiment of this invention. Power supply 10 is connected to readout electronics 12 which may include one or more of hardware, firmware, and/or software. As will be described in greater detail below, the sensor includes one or more capacitors so as to make up a capacitive sensor 5 in certain example embodiments. While different types of capacitors may be used, capacitors each having a pair of approximately coplanar electrodes arranged in a fractal pattern may be used in the sensor in certain example embodiments of this invention. In certain example embodiments, a fractal pattern may be divided into a capacitive array. Data from and/or related to the sensing capacitor(s) of the capacitive sensor 5 is received and read by readout electronics 12 which may be made up of one or more of hardware, firmware and/or software. Readout electronics 12 pick up electrical noise and convert the same to digital signal(s). This digital signal(s) is passed to computing module 14 (which may be made up of one or more of hardware, firmware and/or software) which determines what action the wipers should take. For example, the wipers might initiate a single wipe, low-speed wipes, high-speed wipes, etc., based on the data analyzed from and/or related to the capacitive sensor. The wipers also may be caused to turn off, slow/increase the speed at which they are wiping, etc., based on the data analyzed from and/or related to the capacitive sensor. Wiper control system motor 16 receives instructions from computing module 14 and directs wipers 18 to take the appropriate action.

In certain example embodiments, the capacitive sensor 5 interfaces with a Local Interconnect Bus (LIN bus) of a vehicle. A LIN bus (not shown) typically is a serial bus to which slave devices in an automobile are connected. A LIN bus typically executes a handshake(s) with slave devices to ensure that they are, for example, connected and functional. Additionally, a LIN bus may provide other information to slave devices, such as, for example, the current time.

In certain example embodiments of this invention, the capacitive sensor 5 includes a plurality of capacitors in the form of any suitable array.

Figure 1B:
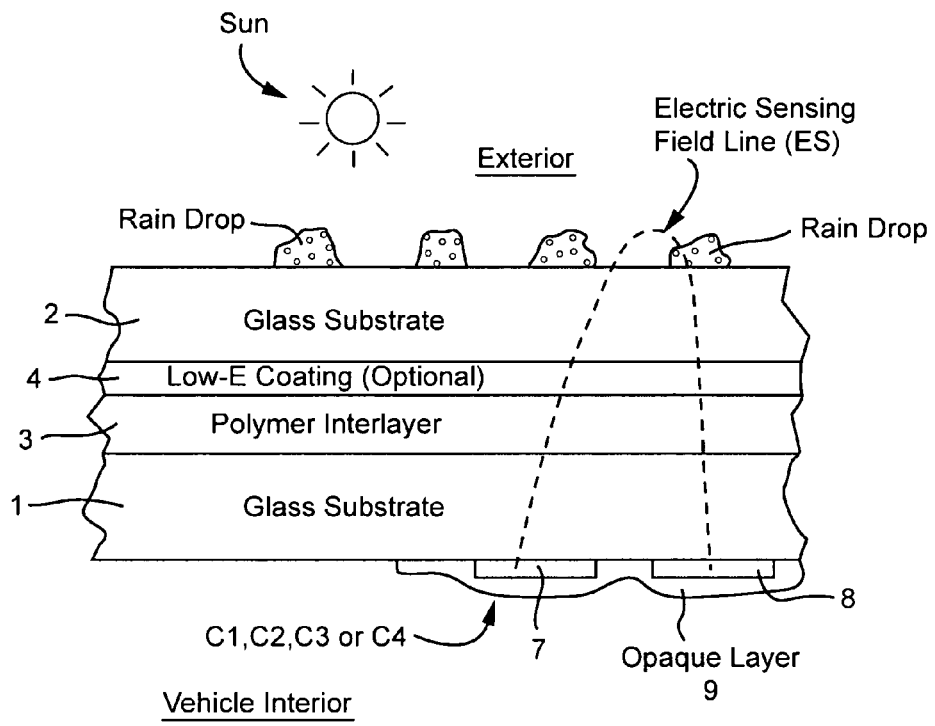
FIG. 1(b) is a cross sectional view of a rain sensor according to an example embodiment of this invention, that may use the features of FIG. 1(a) and/or one or more of FIGS. 2-12.
Figure 1C:
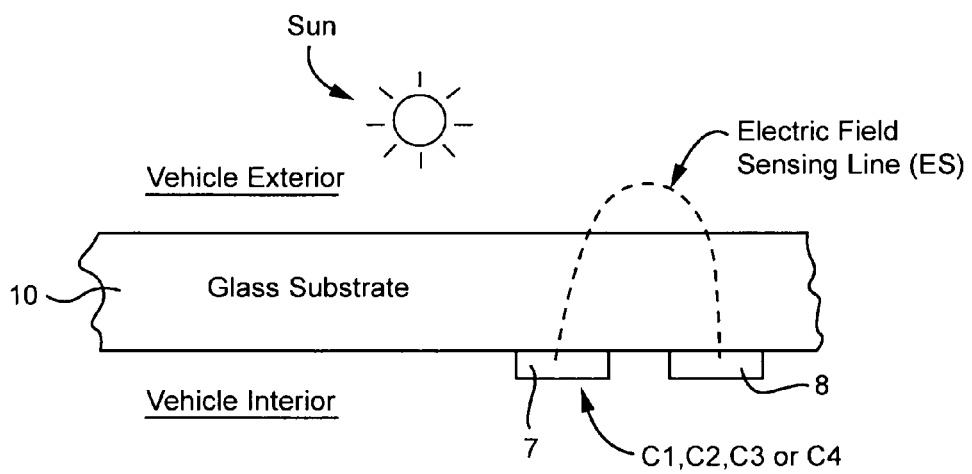
FIG. 1(c) is a cross sectional view of a rain sensor according to another example embodiment of this invention, that may use the features of FIG. 1(a) and/or one or more of FIGS. 2-12.
Figure 1D:
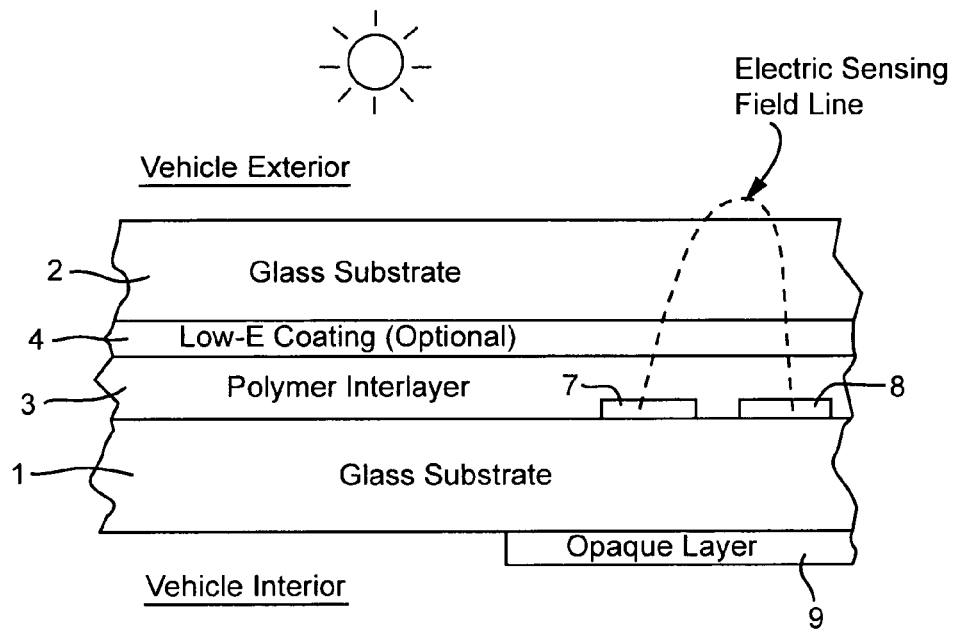
FIG. 1(*d*) is a cross sectional view of a rain sensor according to another example embodiment of this invention, that may use the features of FIG. 1(*a*) and/or one or more of FIGS. 2-12.
Figure 1E:
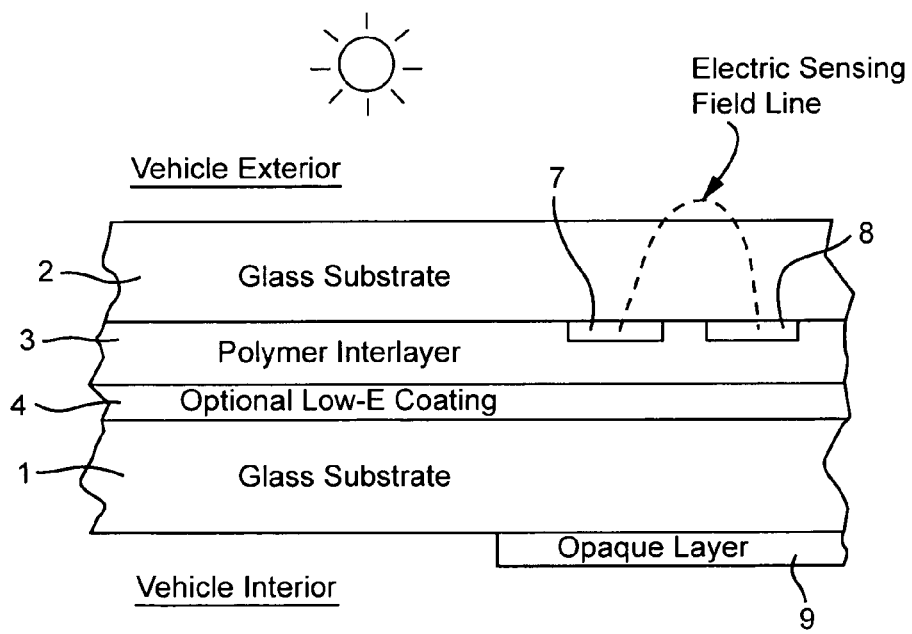
Figure 1F:
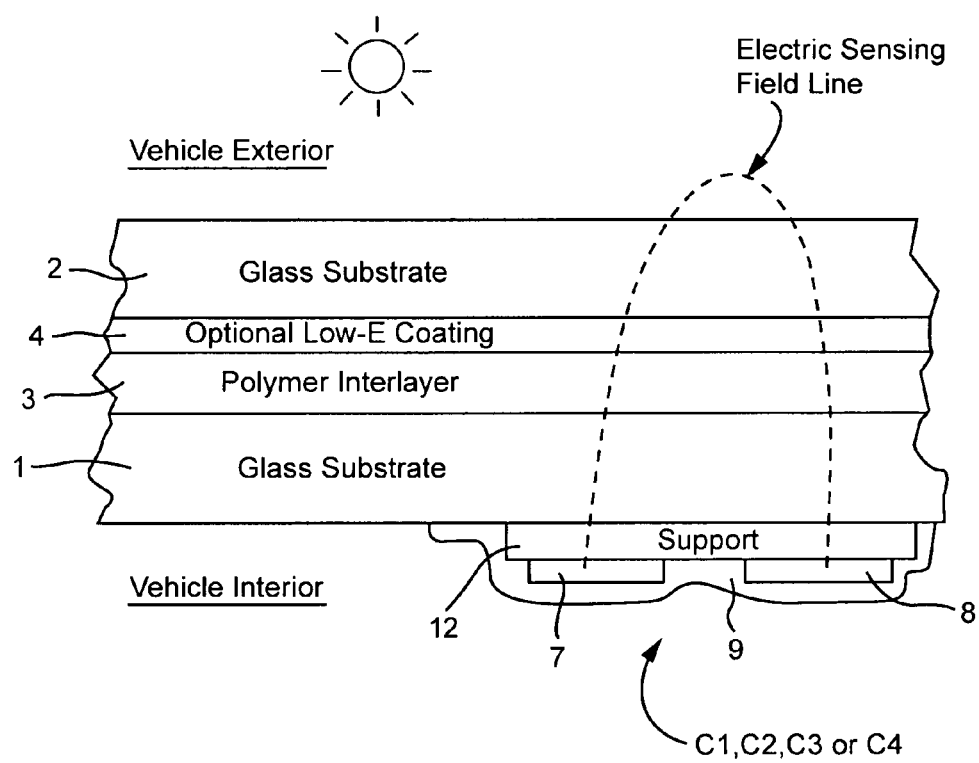

FIG. 1(b) is a cross-sectional view of a vehicle window including a moisture sensor according to an example embodiment of this invention. A windshield of the vehicle includes inner glass substrate 1 and outer glass substrate 2 that are laminated together via a polymer-inclusive interlayer 3 of a material such as polyvinyl butyral (PVB) or the like. An optional low-e (low emissivity) coating 4 may be provided on the inner surface of the exterior glass substrate 2 (or even on the surface of substrate 1) in certain example embodiments of this invention. A low-E coating 4 typically includes at least one thin IR reflecting layer of a material such as silver, gold or the like sandwiched between at least first and second dielectric layers of material such as silicon nitride, tin oxide, zinc oxide, or the like. Example low-E coatings 4, for purposes of example and without limitation, are described in U.S. Pat. Nos. 6,686,050, 6,723,211, 6,782,718, 6,749,941, 6,730,352, 6,802,943, 4,782,216, 3,682,528, and 6,936,347, the disclosures of which are hereby incorporated herein by reference.

FIG. 1(b) illustrates an example capacitor of the capacitive sensor. While the capacitive sensor of FIG. 1(a) typically includes a plurality of capacitors in an array, only one capacitor of the sensor is shown in FIG. 1(b) for purposes of simplicity. The other capacitors are similar in cross section to the one shown in FIG. 1(b) in certain example embodiments of this invention. The example capacitor (C1, C2, C3 or C4) of the capacitive sensor shown in FIG. 1(b) includes a pair of spaced apart coplanar or substantially coplanar capacitor electrodes 7 and 8. The electrodes 7 and 8 are of a conductive material that may be printed or otherwise formed on the window. For example, the capacitor electrodes 7 and 8 of the sensing capacitor may be made of or include silver, ITO (indium tin oxide), or other suitable conductive material. In certain example embodiments, the capacitor shown in FIG. 1(b) is affected by a rain droplet on the exterior surface of the window because electric field Es of the capacitor extends to or beyond the exterior surface of the window as shown in FIG. 1(b) and thus can interact with the rain droplet or other material on the window's exterior surface. Signals received from and/or relating to the sensing capacitor(s) and analysis thereof is described herein.

In the FIG. 1(b) embodiment, an opaque insulating layer (e.g., black frit or enamel, or the like) 9 is provided on the window over the electrodes 7 and 8 in order to shield the electrodes 7, 8 from the view of a passenger(s) sitting inside the vehicle. Thus, it will be appreciated that the opaque layer 9 is only provided on a small portion of the window, including in the area where the capacitive array of the rain sensor's array of capacitors is located. In certain example instances, the rain sensor's capacitive array and thus the opaque layer 9 may be located on a vehicle windshield in an area proximate the rear-view mirror mounting bracket. In certain example embodiments, the opaque layer 9 (e.g., black frit or enamel) may contact the fractal pattern of the capacitor electrodes 7, 8 directly because the layer 9 is not conductive. However, even if a black frit layer 9 were conductive (which is possible), its dielectric constant is close to that of water so that it will not adversely interfere with the capturing of data from and/or related to the capacitors C1-C4 and associated analysis.

Figure 2A:
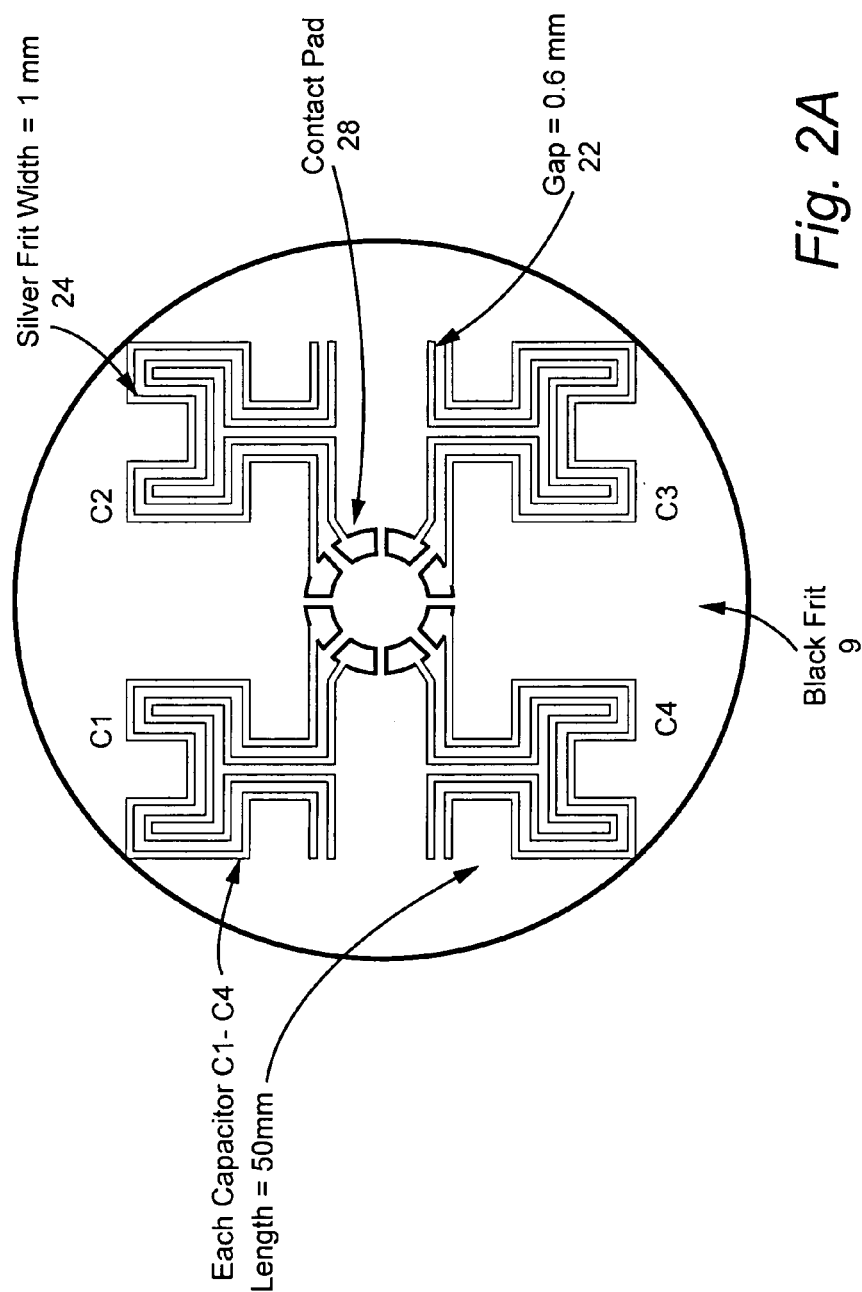
FIG. 2A is an exemplary optimized pattern for a quadrant capacitive array based on Hilbert fractals, where such capacitors may be provided on the window as a sensor array in the embodiments of one or more of FIGS. 1(*a*)-1(*f*) and 4-12 for example.

FIG. 2A is a top or plan view illustrating an example capacitive sensor array including four capacitors C1, C2, C3 and C4. Each of these capacitors C1, C2, C3 and C4 includes first and second spaced apart coplanar capacitor electrodes 7 and 8 as shown in FIG. 1(b) (or any of FIGS. 1(c)-1(f)). The capacitor electrodes 7 and 8 of each capacitor C1-C4 may be made of conductive silver frit or the like as shown in FIG. 2A. Moreover, in certain example embodiments, there may be a gap 22 of from about 0.2 to 1.5 mm, more preferably from about 0.3 to 1.0 mm (e.g., 0.6 mm), between the coplanar capacitor electrodes 7 and 8 of a capacitor (C1, C2, C3 and/or C4) as shown in FIG. 2A. In the FIG. 2A embodiment, the capacitors C1-C4 are covered with an insulating black frit layer 9 which is the same as the opaque layer 9 discussed above with respect to FIG. 1(b). In FIG. 2A, a contact pad array is provided in the center of the sensor array, and includes four contact pads electrically connected to the respective electrodes 7 of the capacitors C1-C4, and four contact pads electrically connected to the respective electrodes 8 of the capacitors C1-C4. An example contact pad is referred to by reference numeral 28 in FIG. 2A. The four white colored contact pads 28 in FIG. 2A are electrically connected to the respective capacitor electrodes 7 of capacitors C1-C4, whereas the dark grey colored contact pads 28 in FIG. 2A are electrically connected to the respective capacitor electrodes 8 of the capacitors C1-C4. All of the sensing capacitors C1-C4 are sensitive to moisture such as rain on the external surface of the window.

In the FIG. 2A embodiment, each of the capacitors C1-C4 of the capacitive sensor is formed using fractal geometry. In particular, each of the coplanar electrodes 7 and 8 of each capacitor C1-C4 is formed with a fractal geometry. Fractal design patterns allow, for example, a high capacitance to be realized in a small area, and are therefore desirable over other geometries in certain example rain sensor applications. Fractal geometry may be grouped into (a) random fractals, which may be called chaotic or Brownian fractals and include a random noise component, and (b) deterministic or exact fractals. In deterministic fractal geometry, a self-similar structure results from the repetition of a design or motif (or "generator") (i.e., self-similarity and structure at all scales). In deterministic or exact self-similarity, fractal capacitors may be constructed through recursive or iterative means. In other words, fractals are often composed of or include many copies of themselves at different scales.

In the FIG. 2A embodiment, it can be seen that the coplanar electrodes 7 and 8 of each capacitor (where the electrodes 7 and 8 are shown but not labeled in FIG. 2A due to the dark color of the frit 9, but are spaced apart by gaps 22) have fractal geometries and are arranged substantially parallel to each other throughout the meandering length of each capacitor. In other words, each electrode 7, 8 of a given capacitor (e.g., C1, C2, C3 or C4) has a meandering shape in the fractal geometry, but stays substantially parallel to the other electrode (the other of 7, 8) of the capacitor throughout the meandering length of the capacitor. The overall length of each capacitor (e.g., C1), along the meandering length of the fractal, is from about 25 to 200 mm in certain example embodiments of this invention, more preferably from about 30 to 90 mm, with an example being about 50 mm.

Figure 2B:
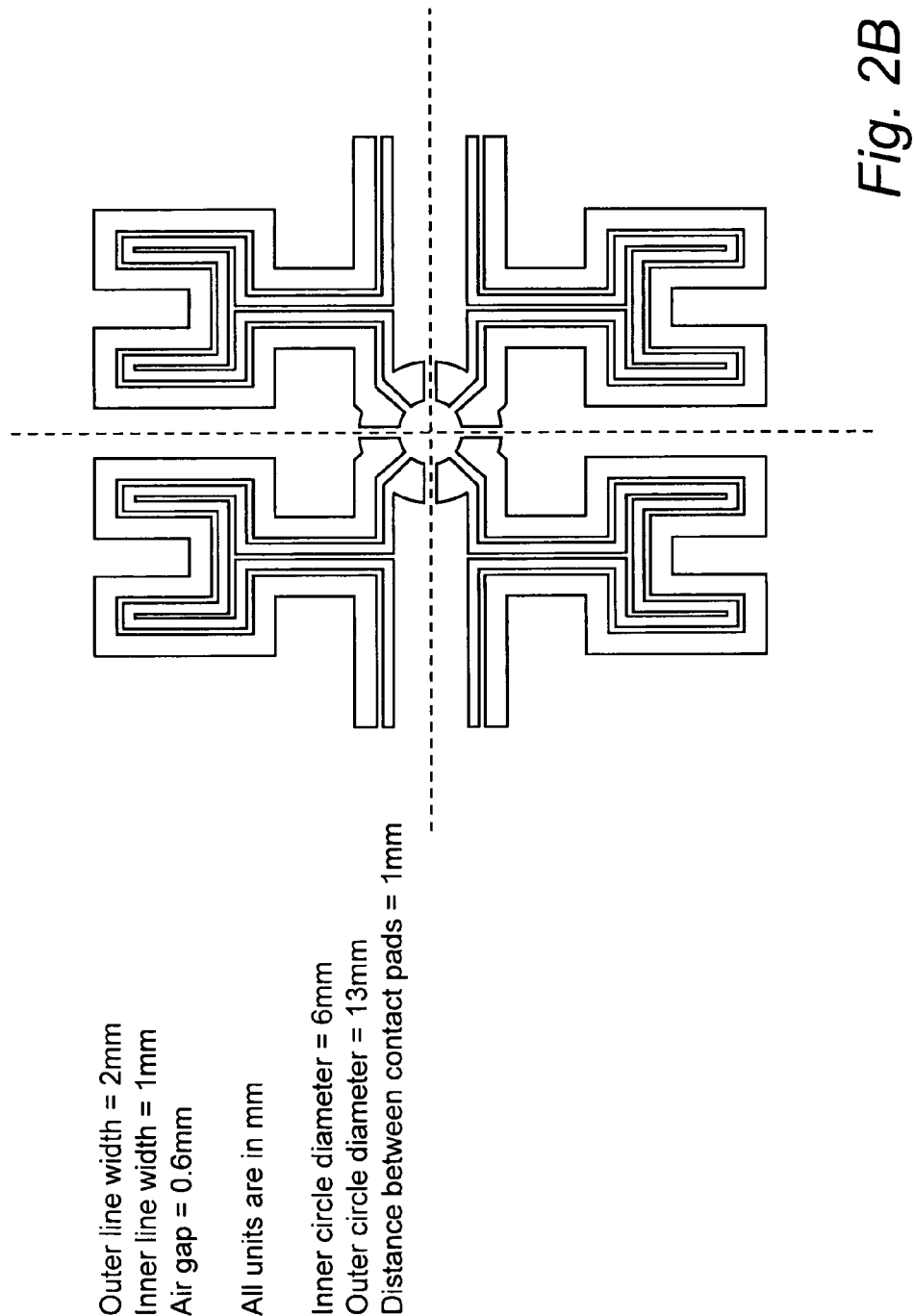
FIG. 2B is another exemplary optimized pattern for a quadrant capacitive array, where such capacitors may be provided on the window as a sensor array in the embodiments of one or more of FIGS. 1(*a*)-1(*f*) and 4-12 for example.
Figure 3:
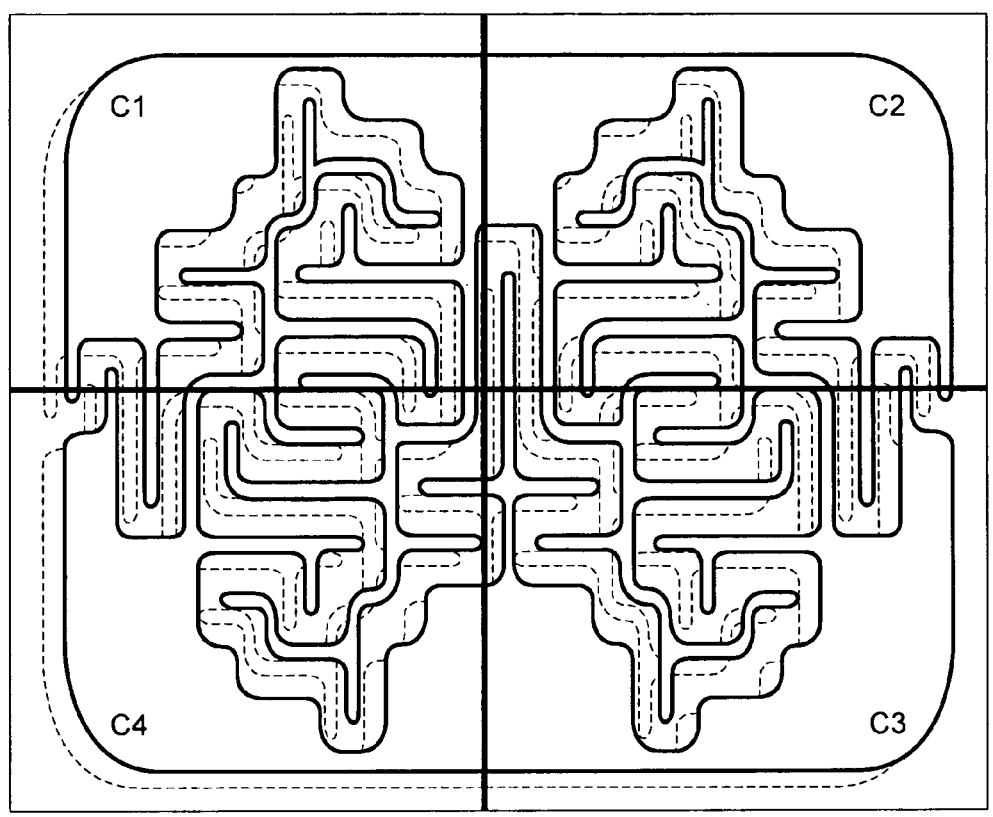
FIG. 3 is an enlarged picture of yet another exemplary quadrant capacitive array, where such capacitors may be provided on the window as a sensor array in the embodiments of one or more of FIGS. 1(*a*)-1(*f*) and 4-12 for example.

The fractal pattern of FIG. 2A is a Hilbert fractal pattern. The electrodes 7, 8 of the capacitors C1-C4 in the FIG. 2A embodiment form a Hilbert fractal pattern, for purposes of example only and without limitation. In particular, the capacitors shown in FIG. 2A are shaped in a third-order Hilbert fractal manner. Hilbert fractals are continuous space-filling fractals, with fractal dimensions of two. This means that higher-order fractals will become more square-like. A Hilbert fractal can be formed by using the following L-system:

```
Hilbert {
    Angle 90
    Axiom X
    X = -YF+XFX+FY-
    Y = +XF-YFY-FX+
}
``` where "Angle 90" sets the following rotations to 90 degrees, X and Y are defined functions, "F" means "draw forward", "+" means "turn counterclockwise", and "−" means "turn clockwise". While Hilbert fractal geometries may be used in forming the capacitors C1-C4 in certain example embodiments of this invention, this invention is not so limited, and other types of fractals may also be used to form the capacitor shapes. For example, the capacitor electrodes 7, 8 of capacitors C1-C4 in any embodiment herein may be formed using any of the fractal designs disclosed in any of U.S. Pat. Nos. 6,552,690, 6,104,349, 6,140,975, 6,127,977, 6,084,285, 6,975,277, the disclosures of which are hereby incorporated herein by reference. In certain example embodiments of this invention, as shown in FIGS. 2A, 2B and 3, all sensing capacitors of the sensing array may be identical or substantially identical in shape.

In preferred embodiments, each of the capacitors C1-C4 in the sensor array may be electrically floating (this may be called a virtual ground in certain example instances) so as to not have a fixed common ground such as a fixed zero volts, and/or spatially separated or the like which may be useful with respect to the correlation functions. Additionally, the lack of a common ground means that the capacitive array will not be subject to adverse effects from interference such as, for example, EMI interference thereby reducing the potential for false wipes, false detections, and the like.

The fractal design for capacitors C1-C4 may be used in any of the embodiments of FIGS. 1(*a*)-1(*f*).

FIG. 1(*c*) is a cross sectional view of another example embodiment of this invention, which may use the system of FIG. 1(*a*) and one or more of the embodiments of FIGS. 2-12. In the FIG. 1(*c*) embodiment, the vehicle window (e.g., backlite) is made up of only one glass sheet 10, and the electrodes 7, 8 of the capacitor are provided on, directly or indirectly, the interior major surface of the glass sheet 10. The capacitor (e.g., C1) shown in FIG. 1(*c*) is designed such that it is affected by a rain droplet (or other material) on the exterior surface of the window because the electric field Es of the capacitor extends to or beyond the exterior surface of the window as shown in FIG. 1(*c*) and thus can interact with the rain droplet or other material on the window's exterior surface. Each of the capacitors C1-C4 is formed in a similar manner. It is noted that the use of the word "on" herein covers both directly on and indirectly on, and is not limited to physical contact or touching unless expressly stated. An opaque layer 9, similar to that shown in the FIG. 1(*b*) embodiment, may also be provide in the FIG. 1(*c*) embodiment if desired.

FIG. 1(*d*) is a cross sectional view of another example embodiment of this invention, which may use the system of FIG. 1(*a*) and one or more of the embodiments of FIGS. 2-12. In the FIG. 1(*d*) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(*d*) embodiment differs from the FIG. 1(*b*) embodiment in that the electrodes 7, 8 of the capacitor are provided on the major surface of glass substrate 1 that is furthest from the vehicle interior. The capacitor electrodes 7, 8 may contact the polymer interlayer 3 in this embodiment, in certain example instances. The capacitor (e.g., C1, C2, C3 or C4) shown in FIG. 1(*d*) is designed such that it is affected by a rain droplet (or other material) on the exterior surface of the window because the electric field Es of the capacitor extends to or beyond the exterior surface of the window as shown in FIG. 1(*d*) and thus can interact with the rain droplet or other material on the window's exterior surface. Each of the capacitors C1-C4 of the sensor array is formed in a manner similar to that shown for the capacitor of FIG. 1(*d*). Opaque layer 9 may also be provided in the FIG. 1(*d*) embodiment if desired, over a portion of the window so as to shield the capacitor electrodes from a vehicle passenger's view. In the embodiment shown in FIG. 1(*d*), the electrodes 7 and 8 may be formed of a conductive silver frit or ITO printed or patterned directly on and contacting the surface of substrate 1. However, this invention is not so limited, and the electrodes 7 and 8 of one or more capacitors of the sensor may instead be formed and patterned from a metallic conductive IR reflecting layer (e.g., silver based layer) of a low-E coating 4 that is supported by the window.

FIG. 1(*e*) is a cross sectional view of another example embodiment of this invention, which may use the system of FIG. 1(*a*) and one or more of the embodiments of FIGS. 2-12. In the FIG. 1(*e*) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(*e*) embodiment differs from the FIG. 1(*b*) embodiment in that the electrodes 7, 8 of the capacitor (e.g., C1, C2, C3 or C4) are provided on the major surface of the exterior glass substrate 2 that is closest to the vehicle interior. The capacitor electrodes 7, 8 may contact the polymer interlayer 3 in this embodiment, in certain example instances. The capacitor (e.g., C1, C2, C3 or C4) shown in FIG. 1(*e*) is designed such that it is affected by a rain droplet (or other material) on the exterior surface of the window because the electric field Es of the capacitor extends to or beyond the exterior surface of the window as shown in FIG. 1(*e*) and thus can interact with the rain droplet or other material on the window's exterior surface. Each of the capacitors C1-C4 of the sensor array is formed in a manner similar to that shown for the capacitor of FIG. 1(*e*). Opaque layer 9 may also be provided in the FIG. 1(*e*) embodiment if desired, over a portion of the window so as to shield the capacitor electrodes from the view of a vehicle passengers(s).

FIG. 1(*f*) is a cross sectional view of another example embodiment of this invention, which may use the system of FIG. 1(*a*) and one or more of the embodiments of FIGS. 2-12. In the FIG. 1(*f*) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(*f*) embodiment differs from the FIG. 1(*b*) embodiment in that the electrodes 7, 8 of the capacitor (e.g., C1, C2, C3 or C4) are provided on the major surface of the interior glass substrate 1 that is closest to the vehicle interior, via support member 12. The support member 12, located between the glass substrate 1 and the electrodes 7, 8, may be made of glass, silicon or the like. The capacitor (e.g., C1, C2, C3 or C4) shown in FIG. 1(*e*) is designed such that it is affected by a rain droplet (or other material) on the exterior surface of the window because the electric field Es of the capacitor extends to or beyond the exterior surface of the window as shown in FIG. 1(*f*) and thus can interact with the rain droplet or other material on the window's exterior surface. Each of the capacitors C1-C4 of the sensor array is formed in a manner similar to that shown for the capacitor of FIG. 1(*f*). Opaque layer 9 may also be provide in the FIG. 1(*f*) embodiment if desired, over a portion of the window so as to shield the capacitor electrodes 7, 8 from the view of a vehicle passengers(s).

FIG. 2B is a plan view of an example pattern for a quadrant capacitive array of fractal shaped capacitors C1-C4 for the capacitive sensor according to another example embodiment of this invention. The four capacitors shown in FIG. 2B are similar to those of FIG. 2A, except for the precise shapes thereof. The FIG. 2B capacitors may be used in any of the embodiments of FIGS. 1(*a*)-(*f*). The super-imposed dashed lines show the divisions into four distinct capacitors C1-C4. The outer line width may be about 2 mm, and the inner line width about 1 mm, in certain example embodiments.

FIG. 3 is an enlarged picture of another exemplary quadrant capacitive array of fractal shaped capacitors C1-C4 for the capacitive sensor according to another example embodiment of this invention. The four capacitors shown in FIG. 3 are similar to those of FIGS. 2A and 2B, except for the precise shapes thereof. The FIG. 3 fractal capacitors may be used in any of the embodiments of FIGS. 1(*a*)-(*f*). The superimposed lines show example division between capacitors C1-C4 in FIG. 3. It will be appreciated that some example embodiments may have capacitive arrays with as few as two capacitors. However, it is preferable to have at least four capacitors in certain example embodiments to pick up and derive nuances in perturbations.

The use of the fractal geometry for the sensing capacitors C1-C4 can be advantageous in reducing false readings due to EMI interference in certain example embodiments of this invention. In particular, fractals at high iterations help reduce EMI interference issues, because the Faraday cage or quasi-Faraday cage of the fractal at high iterations reduces EMI coupling thereby reducing adverse effects of EMI interference. Fractals at high iterations form quasi-Faraday cages.

In certain example embodiments of this invention, the readout electronics look at the interaction of rain and/or other perturbations on the window. In certain example embodiments, this process may be accomplished by sequentially charging capacitors, reading their data, quantizing that data, and/or erasing the charges.

Figure 4:
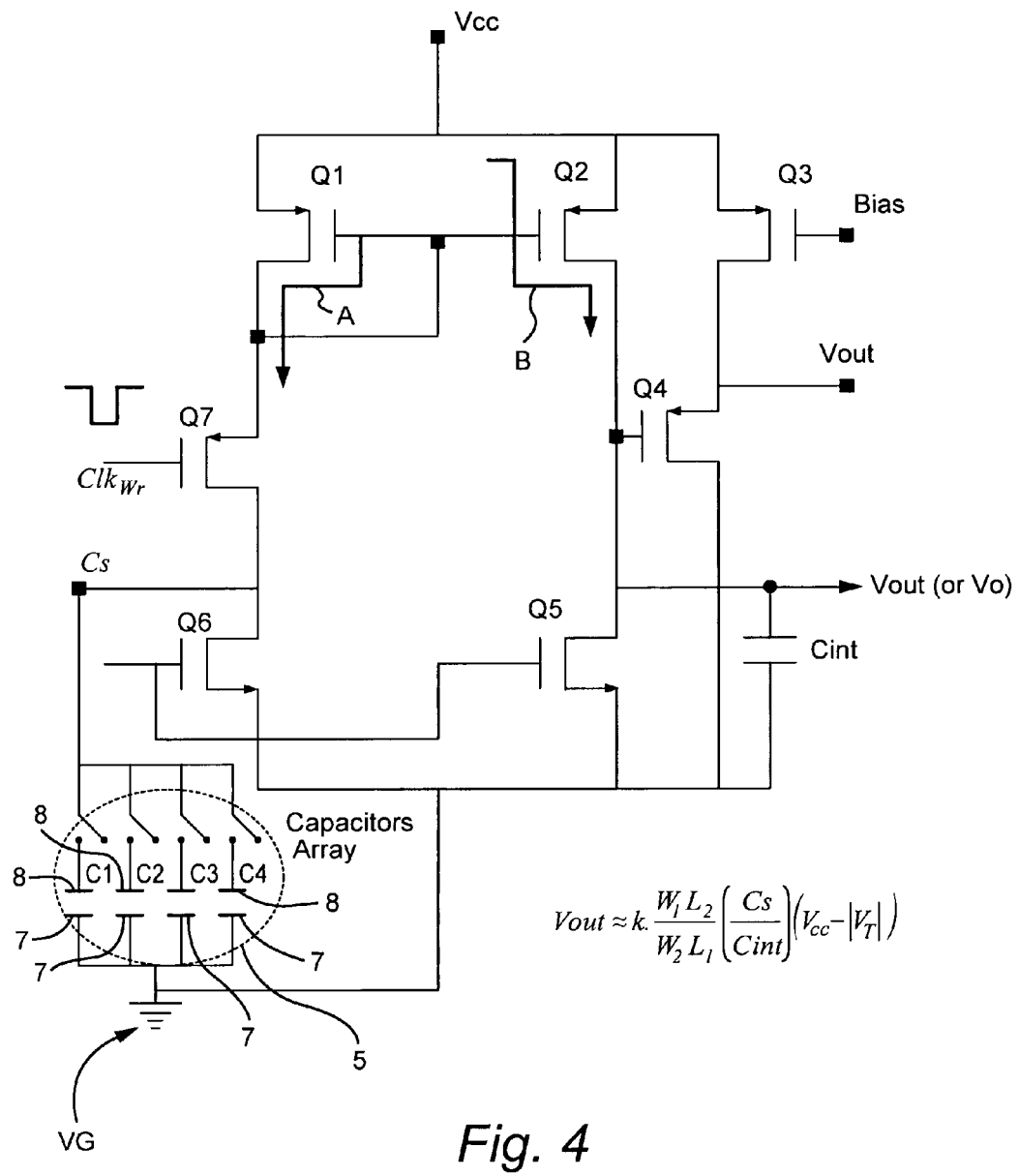
FIG. 4 is an example circuit diagram including exemplary circuitry used for a write clock pulse in readout electronics, for use in one or more of the embodiments of FIGS. 1(*a*)-1(*f*) and 5-12 for example.

FIG. 4 is a circuit diagram of a sensing or read-out circuit according to an example embodiment of this invention. The sensing circuit of FIG. 4 may be made up of the electronics unit 12 and the capacitive sensor array 5 of FIG. 1. Any of the capacitors of FIGS. 1(*b*)-1(*f*), 2A, 2B, and/or 3 may be used as the capacitors C1-C4 of the circuit in FIG. 4. The FIG. 4 circuitry is used for a write clock pulse in readout electronics, in certain example embodiments of this invention. Transistors Q1, Q2, and Q7 are p-channel MOSFETs, with transistors Q1 and Q2 primarily being responsible for a write phase. Transistors Q5 and Q6 are n-channel MOSFETs.

Figure 6:
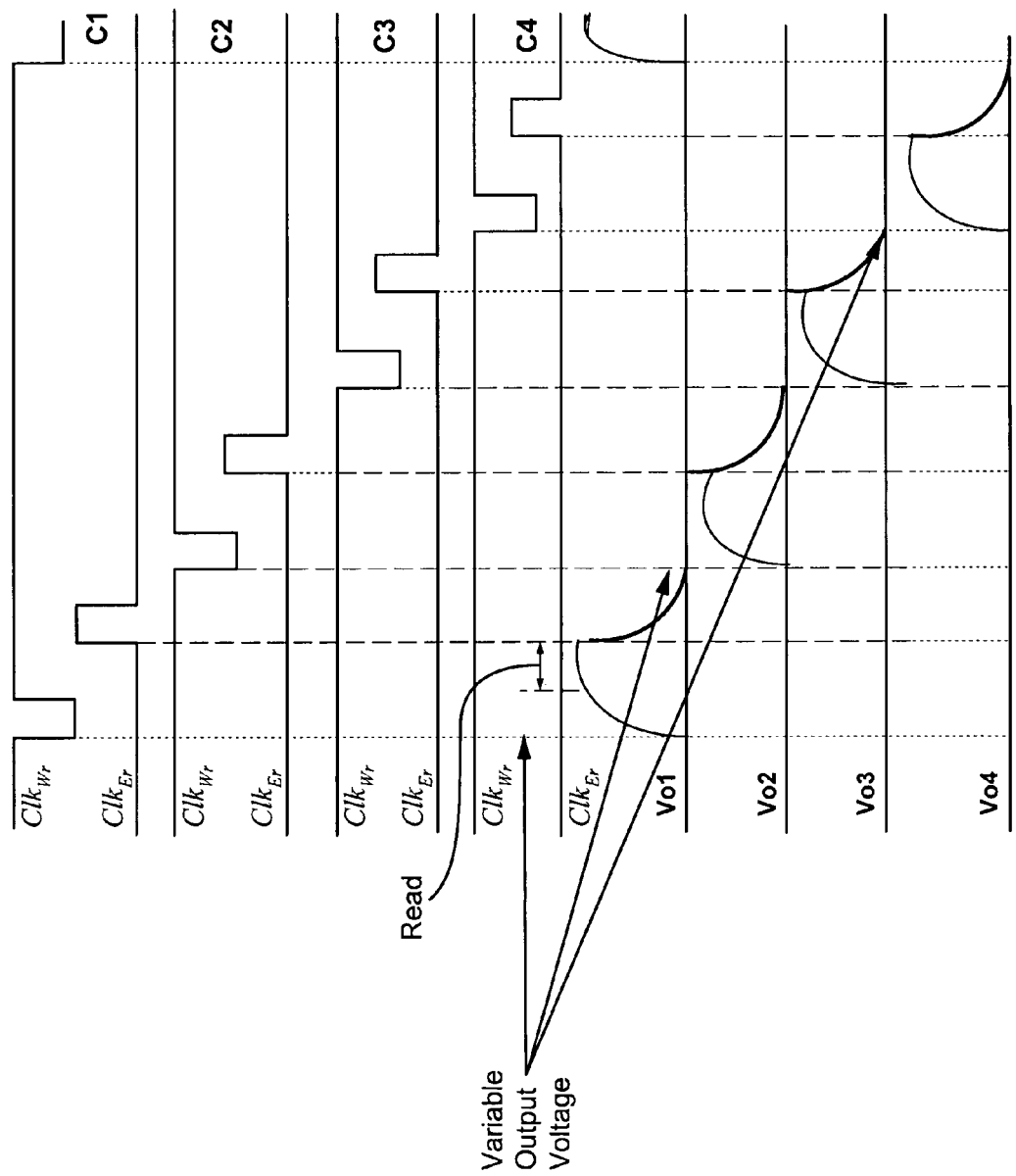
FIG. 6 is an exemplary timing diagram derived from readout circuitry of FIGS. 4-5.

Still referring to FIG. 4, during a write phase a write pulse $Clk_{Wr}$ is input to the gate of transistor Q7, which functions like a resistor or switch, charging one or more of the capacitors C1-C4 of the sensor capacitance $C_s$. FIG. 6 includes certain signals used in the FIG. 4 circuit in the write cycle. In the write cycle, Transistor Q1 is in a saturated mode, since its gate and drain are connected, so that Q1 is on. Q4, Q5 and Q6 are turned off, and Q2 is on during the write mode. Transistors Q3 and Q4 are optional. When Q7 is turned on by the write pulse, we have a write cycle, and Vcc appears at Cs via A and charges one or more of the capacitors C1-C4 of the sensor capacitance Cs. $V_{cc}$ may be a constant voltage, such as 5V, in certain example embodiments. One or more of the capacitors C1-C4 may be charged at a time during a write cycle. However, in certain example embodiments of this invention, the circuit charges and reads the capacitors C1, C2, C3 and C4, one at a time (e.g., see FIG. 6). Thus, during one write cycle, only one of the capacitors C1, C2, C3 or C4 is charged in certain example embodiments of this invention.

The above process described for the left side of the FIG. 4 sensing circuit is essentially mirrored on the opposite or right side of the FIG. 4 circuit. As current flows through the left-side branch, current also flows at B through the right-side branch, and changes to $C_s$ are mimicked, or substantially mimicked in internal mimicking capacitance $C_{int}$. When Q7 is turned on, current also flows through Q2 (which is on) and charges $C_{int}$ using Vcc. Thus, the charging of one of the capacitors C1-C4 is mimicked by the charging of capacitor $C_{int}$. In other words, $C_{int}$ is charged to the same degree, or substantially the same degree, as the capacitor (e.g., C1) being charged on the other side of the FIG. 4 circuit. The output voltage of the FIG. 4 circuit, Vout (or Vo), is based on $C_{int}$ and is taken at or proximate an electrode of the capacitor $C_{int}$ as shown in FIG. 4. An example formula reflecting Vout (or Vo) is shown at the bottom of FIG. 4. Accordingly, it will be appreciated that the output Vout (or Vo) of the FIG. 4-5 circuit is related to and based on the capacitors C1-C4 of the sensor Cs. More specifically, the output Vout of the FIG. 4-5 circuit is related to and indicative of the status of capacitors C1-C4 and the effects on those capacitors of moisture on the exterior window surface, even though Vout is not taken directly from capacitors C1-C4. In particular, Vout (or Vo) is read out during the write cycle, due to the write pulse shown in FIG. 4 (see also FIG. 6). In the formula at the bottom of FIG. 4 for Vout, W1 is for Q1, W2 is for Q2, L1 is for Q1, L2 is for Q2, where W is transistor channel width, and L is transistor channel length; and $V_T$ is a threshold voltage of each MOSFET. It is noted that in alternative embodiments of this invention, the output Vout of the circuit may be taken directly (instead of indirectly via $C_{int}$) from the sensing capacitors C1-C4.

Transistors Q3 and Q4 are optional. In certain example embodiments, these transistors may be at low voltages (e.g., off) during the write phase, and on during the erase phase.

The output signal Vout (or Vo) of the FIG. 4 (and FIG. 5) sensing circuit is sigma-delta modulated in certain example embodiments of this invention. Sigma-delta modulators, which can be used in a sigma-delta digital-to-analog converter (DAC), can provide a degree of shaping or filtering of quantization noise which may be present. Example sigma-delta modulators that may be used are described in U.S. Pat. Nos. 6,975,257, 6,972,704, 6,967,608, and 6,980,144, the disclosures of which are hereby incorporated herein by reference. In certain examples of sigma-delta conversion, over-sampling, noise shaping and/or decimation filtering may be brought to bear. Example advantages of sigma-delta modulation include one or more of: (i) analog anti-aliasing filter requirements are less complex and thus may be cheaper than certain example nyquist based systems; (ii) sample and hold circuitry may be used due to the high input sampling rate and low precision A/D conversion; (iii) since digital filtering stage (s) may reside behind the A/D conversion, noise injected during the conversion process such as power-supply ripple, voltage reference noise and noise in the A/D converter itself may be controlled; (iv) since the sigma-delta converter may be essentially linear it may not suffer from appreciable differential non-linearity and/or background noise level(s) may be independent of input signal level. Improved S/N ratios may be realized.

Figure 5:
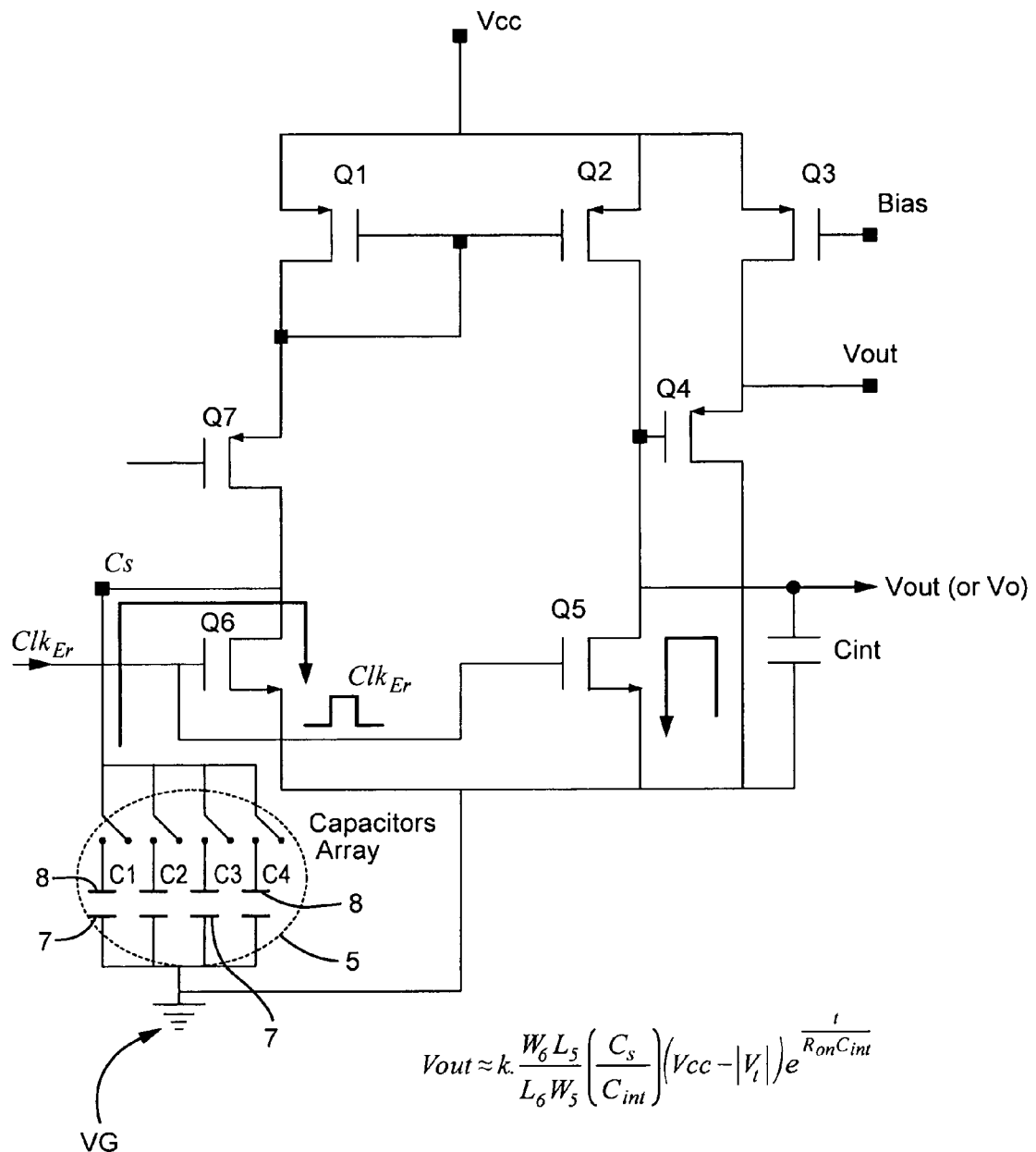
FIG. 5 is an example circuit diagram including exemplary circuitry used for an erase clock pulse in readout electronics, for use in one or more of the embodiments of FIGS. 1(*a*)-1(*f*), 4 and 6-12 for example.

FIG. 4-5 illustrate switches for selectively coupling the various capacitors C1-C4 to the rest of the circuit. The circuit may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time. An example non-limiting switching circuit for selective coupling the read-out electronics to one or more of capacitors C1-C4 as needed or as desired in discussed below in connection with FIG. 31.

Figure 25:
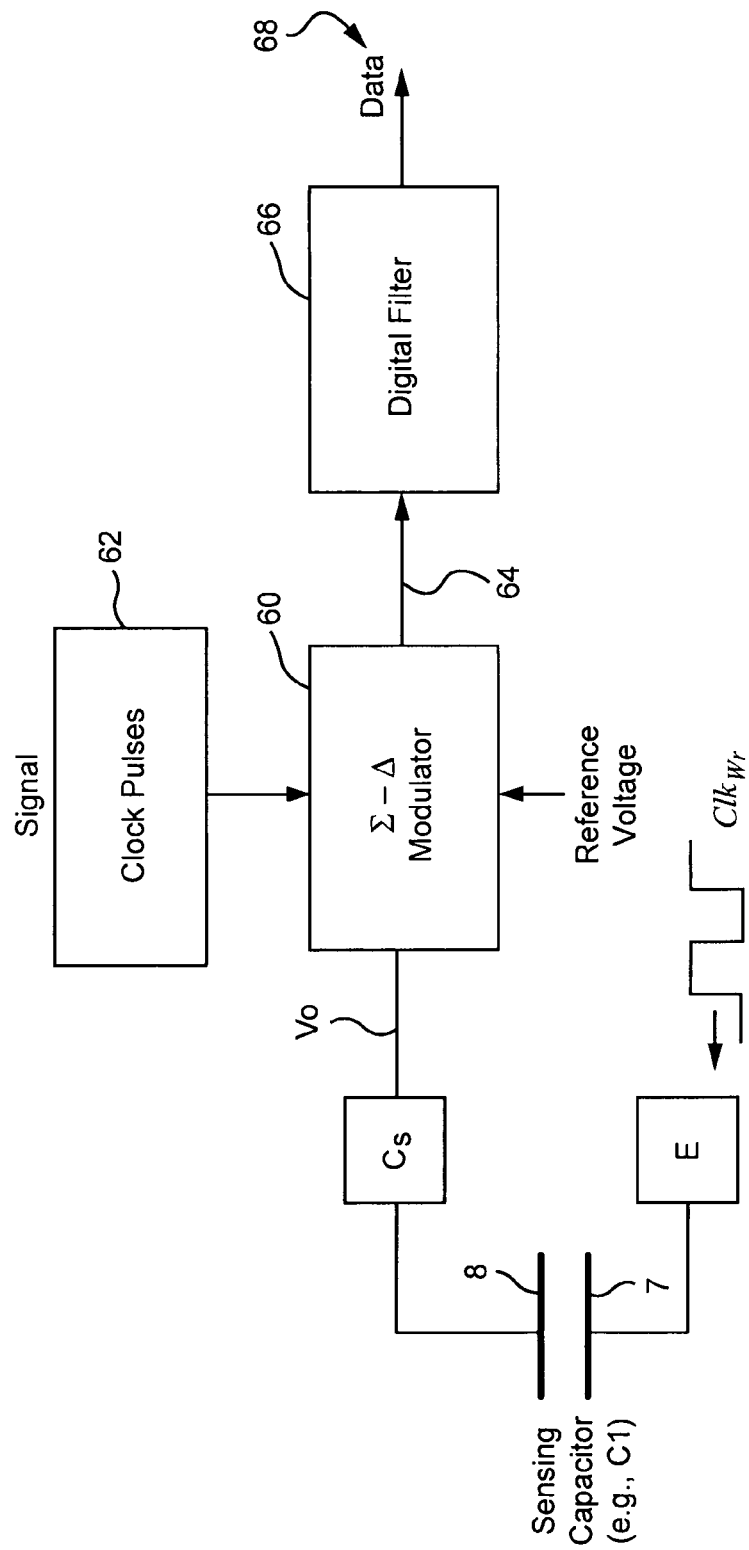
FIG. 25 is a block diagram illustrating circuitry and/or processing of signals according to an example embodiment of this invention where a sensing capacitor (e.g., C1) is present, including sigma-delta modulation.
Figure 26:
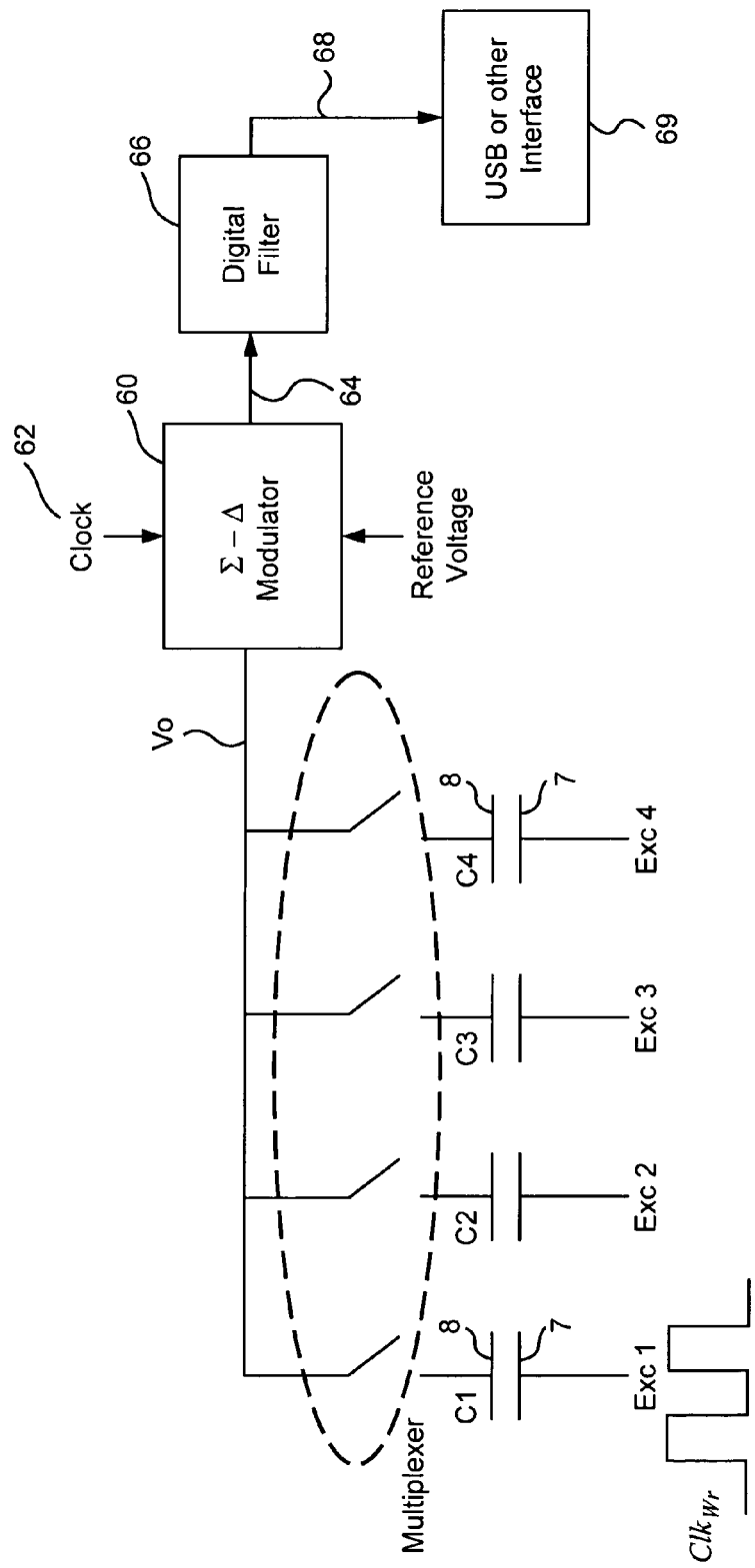
FIG. 26 is a block diagram illustrating circuitry and/or processing of signals according to an example embodiment of this invention where a plurality of capacitors (e.g., C1-C4) are present, including sigma-delta modulation.

FIG. 25 which is a simplified version of a sigma-delta modulator system according to an example embodiment of this invention, for modulating and/or converting the output signal Vout (or Vo) of the FIG. 4 (and FIG. 5) circuit. In FIG. 25, a write pulse (see pulse at the bottom of FIG. 25), is used to charge the sensing capacitor (C1, C2, C3 or C4) as explained above with respect to FIG. 5. The square wave excitation (e.g., for writing and/or erasing cycles) is used on the sensing capacitor to charge and discharge it. This process is mirrored or mimicked, for $C_{int}$ as explained herein. The output signal Vout (or Vo) of the FIG. 4 circuit is sigma-delta modulated by sigma-delta modulator 60. The modulator 60 make take the form of a hardware circuit, firmware, and/or software in different example embodiments of this invention. Clock pulses 62 from a clock are input to the modulator 60, which trigger the latch of a quantizer of the modulator 60. After the output signal Vout (or Vo) are sigma-delta modulated by modulator 60, the modulated signals 64 are forwarded to an optional digital filter 66 (e.g., lowpass filter or the like). Digital filter 66 processes the sigma-delta modulator digital output 64, which is a stream of 0s and 1s. The data is then scaled appropriately using calibration coefficient(s). The filtered data 68 is then read through a serial interface 69 or the like and sent to a computer which does the correlation calculations for chunks of data packets. Thus, the data from the interface 69 is then correlated (e.g., autocorrelated and/or cross-correlated) as explained herein. FIG. 26 is similar to FIG. 25, except that FIG. 26 illustrates an array of sensing capacitors C1-C4 which are multiplexed via a multiplexer. The multiplexer shown in FIG. 26 may be used for selectively coupling the various capacitors C1-C4 to the rest of the circuit including modulator 60. The circuit may read out signals from all of the capacitors C1-C4 simultaneously via multiplexer, or alternatively may only read out signals from one capacitor at a time selected from C1-C4, or as a further alternative may read out signals from a combination of some but not all of capacitors C1-C4 at a given point in time. An example non-limiting switching circuit for use in the position of the multiplexer shown in FIG. 26, for selectively coupling the read-out electronics to one or more of capacitors C1-C4 as needed or as desired, in discussed below in connection with FIG. 31.

Figure 27:
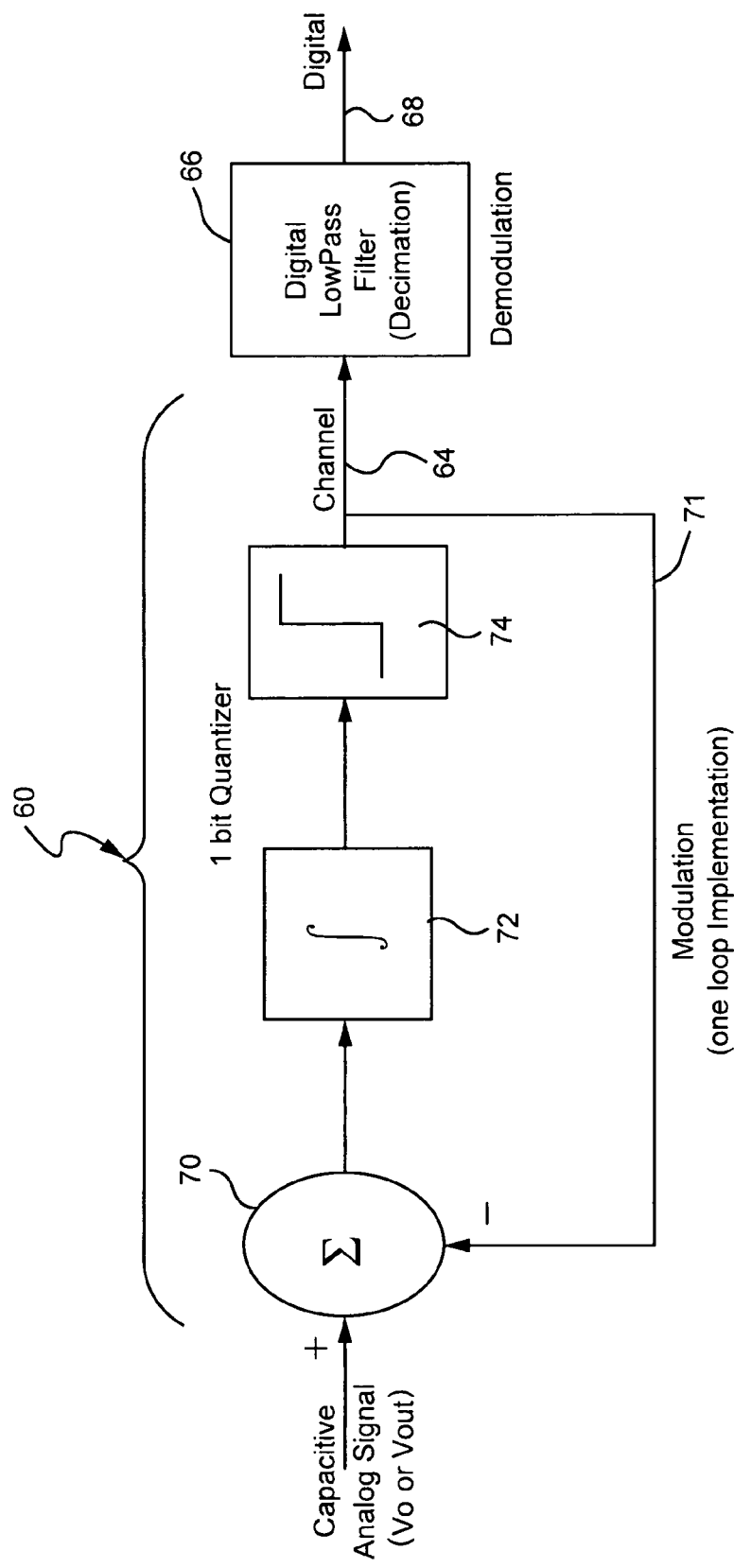
FIG. 27 is a block diagram illustrating sigma-delta modulation according to an example embodiment of this invention; this processing being performed in circuitry, firmware and/or software.

FIG. 27 is a block diagram illustrating an example of sigma-delta modulation which may be performed in the modulator 60 of FIGS. 25-26. Again, this modulation may be performed by circuitry, firmware and/or software in different example embodiments of this invention. The analog output signal Vout (or Vo) of the FIG. 4 (and FIG. 5) circuit is received by a summer 70 of the sigma-delta modulator 60. Adder or summer 70 receives the analog Vout (or Vo) signal as well as a feedback signal from a feedback loop 71 of the modulator 60. The output of adder or summer 70 is received by integrator 72 whose output is received by a quantizer 74 such as a one bit quantizer. The digital output 64 is then filtered 66 as explained above, and so forth. The sigma-delta modulation is advantageous in that it provides oversampling and allows noise such as EMI to be treated and its adverse effects reduced. In particular, the noise is spread by the sigma-delta modulation out over the frequency band so that the signal-to-noise (S/N) ratio can be improved.

Figure 29:
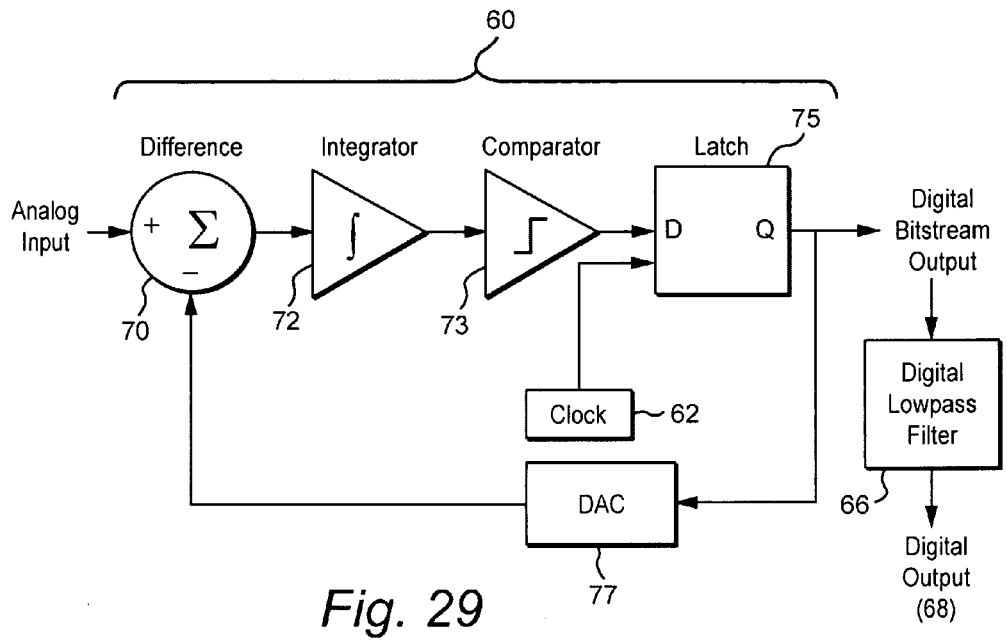
FIG. 29 is a block diagram illustrating sigma-delta modulation according to another example embodiment of this invention; this processing being performed in circuitry, firmware and/or software.

FIG. 29 illustrates another example of a sigma-delta modulation according to an example of this invention. The sigma-delta modulator of FIG. 29 receives an analog input from the FIG. 4, 5 sensing circuit that reaches adder or summer 70. Adder 70 determines the difference between a feedback signal and the input, and its output is forwarded to integrator 72. The output of the integrator 72 is sent to comparator 73. Comparator 73 decides whether its input is higher or lower than a predetermined threshold and can put out a single bit signal based on the same, a bitstream, to the latch 75 (note that quantizer 74 in FIG. 27 may include each of comparator 73 and latch 75). The comparator's output is received by latch 75 for sampling. A way to reduce noise is to increase clock rate from clock 62; e.g., a sampling rate of at least twice the maximum input frequency, with further increases referred to as oversampling rate. The digital bitstream output from the latch is received by the lowpass digital filter 66. The lowpass filter is used because it is sometimes desired to gain the average signal level out of the bitstream. The digital output may be a single-bit serial signal with a bit rate much higher than the data rate, and its average level may represent an average input signal level. The feedback loop, like the one in FIG. 27, includes a digital-to-analog (DAC) converter 77 that may be of the one-bit type or any other suitable type. The filtered data 68 is read through a serial interface 69 or the like and sent to a computer which does the correlation calculations for chunks of data packets.

Figure 30:
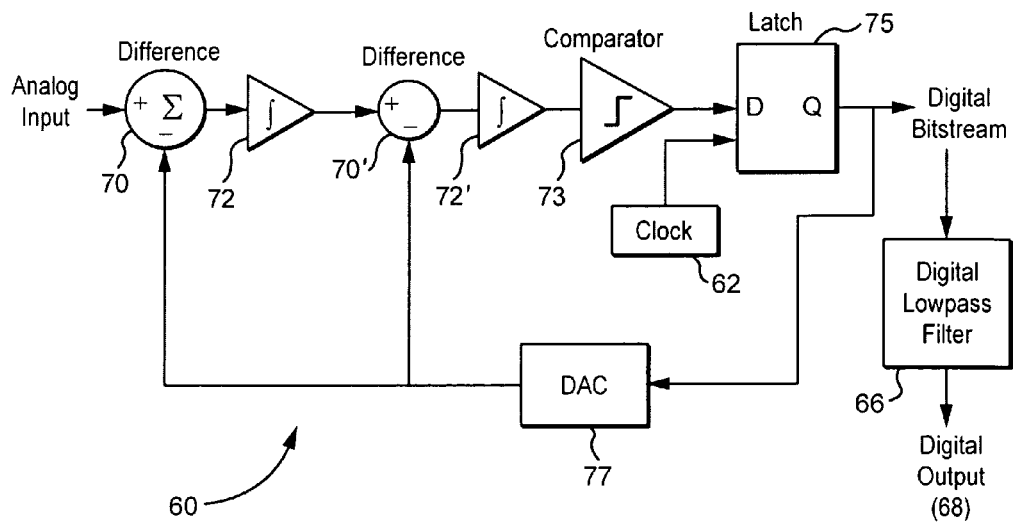
FIG. 30 is a block diagram illustrating sigma-delta modulation according to yet another example embodiment of this invention; this processing being performed in circuitry, firmware and/or software.

FIG. 30 illustrates another example of a sigma-delta modulation according to an example of this invention. The sigma-delta modulator of FIG. 30 receives an analog input from the FIG. 4, 5 sensing circuit that reaches first adder or summer 70. The FIG. 30 sigma-delta modulator scheme is the same as that of FIG. 29 discussed above, except that a second adder or summer 70' and a second integrator 72' are provided in the modulator of the FIG. 30 embodiment.

Referring back to FIG. 4, each capacitor (C1, C2, C3, C4) is discharged before charging the next, in certain example embodiments of this invention. The process of discharging each capacitor is described in connection with the erase pulse, with respect to FIG. 5-6.

FIG. 5 is a circuit diagram of the FIG. 4 sensing circuit, with respect to an erase cycle. During an erase cycle, a previously charged capacitor (C1, C2, C3 and/or C4) is discharged before the next write cycle. FIG. 6 includes example signals used during the erase cycle(s). No reading is performed during the erase phase, in certain example instances. During an erase cycle or phase, Q7 is turned off (the write pulse $Clk_{Wr}$ is not present), and transistors Q5 and Q6 are turned on by an erase pulse $Clk_{Er}$ (see also FIG. 6). Thus, the capacitor (C1, C2, C3 and/or C4) discharges to ground (e.g., V=0) or virtual ground (VG), as does $C_{int}$. Again, $C_{int}$ mimics the capacitance of the sensor Cs. Once the capacitances Cs and $C_{int}$ have been connected to ground and discharged, the erase pulse and cycle ends. Then, the next capacitor (C1, C2, C3 or C4) in the sequence can be prepared, charged, and read.

Thus, referring to FIGS. 4-6, it will be appreciated that according to certain example embodiments of this invention a rain sensor comprises: a sensing circuit comprising at least first and second sensing capacitors (e.g., C1 and C2) that are sensitive to moisture on an external surface of a window, and at least one mimicking capacitor ($C_{int}$) that mimics at least charging and/or discharging of at least one of the first and second sensing capacitors; wherein a writing pulse ($Clk_{Wr}$) causes at least the first sensing capacitor (e.g., C1) to be charged, and an erasing pulse ($Clk_{Er}$) causes each of the first sensing capacitor (e.g., C1) and the mimicking capacitor ($C_{int}$) to substantially discharge; wherein presence of rain on the external surface of the window in a sensing field of the first sensing capacitor (e.g., C1) causes a voltage (see Vo or Vout) at an output electrode of the mimicking capacitor ($C_{int}$) to fluctuate in a manner proportional to fluctuation of voltage at an output electrode (8) of the first sensing capacitor (e.g., C1), even though the rain is not present in a field of the mimicking capacitor ($C_{int}$); and wherein rain is detected based on an output signal (see Vo or Vout) from the output electrode of the mimicking capacitor ($C_{int}$), wherein the output signal is read at least between an end of the writing pulse ($Clk_{Wr}$) and a beginning of the erase pulse ($Clk_{Er}$) (see the "read" area in FIG. 6).

Still referring to FIG. 5, in certain example embodiments of this invention, during the erase cycle, the erase pulse $Clk_{Er}$ causes the capacitor (C1, C2, C3 and/or C4) and thus also the mimicking capacitance $C_{int}$ to discharge to ground (e.g., a fixed potential such as V=0) (see the conventional ground symbol in FIG. 5). However, in other example embodiments of this invention, it has been found that a fixed ground can lead to certain problems. Thus, in such other example embodiments of this invention, during the erase cycle the erase pulse $Clk_{Er}$ causes the capacitor (C1, C2, C3 and/or C4) and thus also the mimicking capacitance $C_{int}$ to discharge to a virtual ground VG that is floating (see VG and the ground symbol in FIG. 5). Stated another way, an electrode of each of capacitors C1-C4 is floating. It may be at a floating or reference potential/voltage. It has been found that a floating or virtual ground can be highly advantageous in certain example embodiments of this invention (e.g., a floating ground and/or capacitor electrode(s) can lead to a significant reduction in EMI interference problems). For example, such a floating or virtual ground may help reduce the chance of the sensor system being tricked by EMI interference. In this respect, reference is made to FIGS. 28(a) and 28(b) (along with FIG. 5).

In FIGS. 28(a)-(b), reference numerals 7 and 8 refer to the electrodes of a capacitor (e.g., C1, C2, C3 or C4). In these figures, "q" refers to charge and Φ refers to potential (Φ1 is different than Φ2). In FIG. 28(a) the capacitor (e.g., C1) is grounded at a fixed potential such as 0 volts (the charge at grounded electrode 7 is fixed at +q). In this respect, when the charge at grounded electrode 7 is fixed at +q, when one brings an external body $E_B$ (e.g., human finger with a higher dielectric constant) into a sensing area of the capacitor (e.g., touching the front surface of the windshield over the capacitor) this external body induces a change in charge −Δq and the other electrode 8 which is not fixed changes from a charge of −q to a charge of −q +Δq in an attempt to balance charge. Thus, if one were to ground the capacitor at a fixed potential such as 0 volts, and read an output voltage of the capacitor, one would read charge changes caused by Δq which is not needed, and this may lead to false readings. Comparing FIGS. 28(a) and 28(b), FIG. 28(b) illustrates an advantage of causing an electrode 7 of the sensing capacitor (e.g., any of C1-C4) to be floating (e.g., at a floating or virtual ground). In FIG. 28(b), the charge q at electrode 7 is not fixed. E.g., the charge at electrode 7 changes from +q' to +q" when the external body comes into contact with the windshield at a sensing area of the capacitor, thereby indicating the floating nature of the electrode. In FIG. 28(b), when the external body (e.g., human finger) is applied to the windshield over the capacitor sensing area the free charges on both electrodes 7 and 8 of the capacitor change. Thus, the adverse effect of Δq is eliminated or reduced by using the floating or virtual ground VG (electrode 7 is floating). In particular, when electrode 7 is floating as in FIG. 28(b), the external body ($E_B$) does not adversely affect summation of charge because adding the charges (+q" and −q") of the electrodes 7 and 8 when the external body is present gives zero or substantially zero. False readings due to EMI interference can also be reduced by using this floating feature. Thus, in certain example embodiments, the floating nature may allow the absolute values of the charges q at capacitor electrodes 7 and 8 to be the same or substantially the same even when the external body is present since the electrode 7 is floating and is not fixed at ground. This is one example reason why it may be advantageous to cause the electrodes 7 of the capacitors C1-C4 to be floating, or be at a virtual ground VG as shown in FIG. 5. Thus, referring to FIGS. 5 and 28, the sensing capacitors C1-C4 are floating and both electrodes thereof are isolated from ground. Accordingly, according to certain example embodiments of this invention, the rain sensor comprises at least one sensing capacitor (C1, C2, C3 and/or C4) that is sensitive to moisture on an external surface of a window, the sensing capacitor including a first capacitor electrode (8) that receives a charging signal and a second capacitor electrode (7) spaced apart from the first capacitor electrode (8); and wherein the second capacitor electrode (7) is floating so that the sensing capacitor is isolated from ground.

FIG. 6 is an exemplary timing diagram of signals applied to or read out from the FIG. 4-5 circuit during the write and erase modes/cycles. As noted above, the capacitors (C1-C4) are sequentially charged, read, quantized, and erased. FIG. 6 shows a clock write ($Clk_{Wr}$) and erase ($Clk_{Er}$) pulse for each capacitor C1-C4, in sequence. Then, voltages are quantized and output. Variable output voltage Vo1-Vo4 correspond to capacitors C1-C4 respectively, and thus $C_{int}$. It is noted that the output signals Vo1-Vo4 in FIG. 6 are taken at $V_{out}$ (or Vo) in FIGS. 4-5. Moreover, in FIG. 6, the output signals Vo are read or analyzed (e.g., for autocorrelation and/or cross-correlation) at the peak read areas (see "Read" in FIG. 6) of the output signals where the output signals are substantially stabilized and/or the capacitor saturated. In particular, the output signal $V_{out}$ (or Vo) in FIG. 6 for a particular capacitor (C1) is read in the "read area" after the end of the write pulse ($Clk_{Wr}$) for that capacitor, and before and/or up to the beginning of the erase pulse ($Clk_{Er}$) for that capacitor.

Still referring to FIG. 6, for example, a drop of water on the exterior surface of a windshield will affect the magnitude of the output signal(s) $V_{out}$ (or Vo). For instance, a water drop over the area of a given capacitor (e.g., C1) will cause the level of the output signal(s) $V_{out}$ (or Vo) for that capacitor in the "read" area of the signal to be higher compared to a situation where no such drop was present. The exact magnitude or level depends on the size of the water drop. With increasing water amounts, the magnitude of the signal at the "read" area gets higher because the dielectric constant of water is higher than that of glass and/or air and this causes the capacitance to increase. In a similar manner, if no water drop is present on the windshield over the area of a given capacitor (e.g., C1) then this will cause the level of the output signal(s) $V_{out}$ (or Vo) for that capacitor in the "read" area of the output signal to be lower compared to a situation where a drop was present.

The signals (e.g., from the capacitor(s)) may be converted from analog-to-digital via a sigma-delta modulation scheme or the like, which may be implemented at the software level or in any other suitable manner such as via hardware. The principle behind sigma-delta architecture is to make rough evaluations of the signal, to measure the error, integrate it, and then compensate for that error. Data may be oversampled at a given rate of at least 32 kHz, e.g., more preferably 64 kHz, though it will be appreciated that other sampling rates may be used. The course quantization can be recovered by the sigma-delta modulation scheme to produce a simple binary 0 or 1 output, corresponding to on and off, respectively. Thus, the sigma-delta modulation scheme may be used to reduce noise (e.g., at the tail of the signal) and produce a digital output stream (e.g., 1s and 0s).

Figure 7:
FIG. 7 is an exemplary flowchart or state diagram showing how autocorrelation and cross-correlation data may be used to control wipers according to an example embodiment of this invention, which may be used in conjunction with one of more of FIGS. 1-6 and 8-12.

Before discussing the detailed operation of and example mathematics behind an example sensor algorithm, an overview of the states in which the sensor and/or wipers can take will be given in connection with FIG. 7, which is an exemplary state diagram showing how autocorrelation and cross-correlation data may be used to control vehicle wipers. The system begins in Start/Initialization State S702. In this state, all buffers are cleared in certain example instances. Based on the inputs of capacitors $C_1, C_2, \ldots, C_n$, analog-to-digital conversion of the signals from the respective inputs is accomplished via sigma-delta modulation. Data is read for the plurality of channels over time period T. Operating Mode Selector State S704 functions as a switch to select between the manual or automatic wiper mode. If Operating Mode Selector State S704 indicates that manual mode is selected, then in Manual Mode State S706 an auto mode may be disabled and a pre-existing manual mode enabled. Then, the system returns to Start/Initialization State S702. However, if Operating Mode Selector State S704 indicates that auto mode is selected, the automatic wiper mode is enabled in Auto Mode State S708.

In Autocorrelator Engine State S710, at least three computations are performed. First, a normalized autocorrelation is calculated for each signal input of the capacitive array. Second, the gradient of the autocorrelation is calculated. Third, the difference between the signal input and a reference non-disturbed signal ($\Delta_1$) may be calculated. This information is passed to Is Raining? State S712, in which at least three conditions are checked to determine whether it is likely that it is raining, there is moisture on the windshield, etc. Likely indications of rain are that the gradient of the autocorrelation is greater than 1, all autocorrelation values are positive, and/or $\Delta_1$ is greater than some pre-defined threshold value t1. If these conditions are not met, the system moves to Park Wipers/Stop Motor State S714, where wipers are parked (if they are moving) or not actuated, and the motor is stopped (if it is engaged), and the system is returned to Start/Initialization State S702.

On the other hand, if all conditions are met (e.g., it is likely that there is an interaction of water, moisture or some other perturbation on the glass, etc.), the system moves to Lowest Speed State S716, in which the wiper motor is activated at the lowest speed available. In Cross-Correlator Engine State S718, the cross-correlation between the input signals from the capacitors is calculated. The cross-correlation curve shape is determined, and the symmetry of the two sides of the cross-correlation curve are checked for symmetry. As will be described below, these checks help, for example, to determine the type of perturbation (e.g., light rain, heavy rain, fog, snow, etc.) hitting the window (e.g., windshield). In Rain Degree Assessment State S720, the "degree of rain" (e.g., heavy, light, etc.) is determined. Based on this determination, the wiper motor is activated at the appropriate speed in Speed Selector State S722. Lastly, the system is returned to Start/Initialization State S702 to determine whether there is any change in conditions outside the car.

Figure 8:
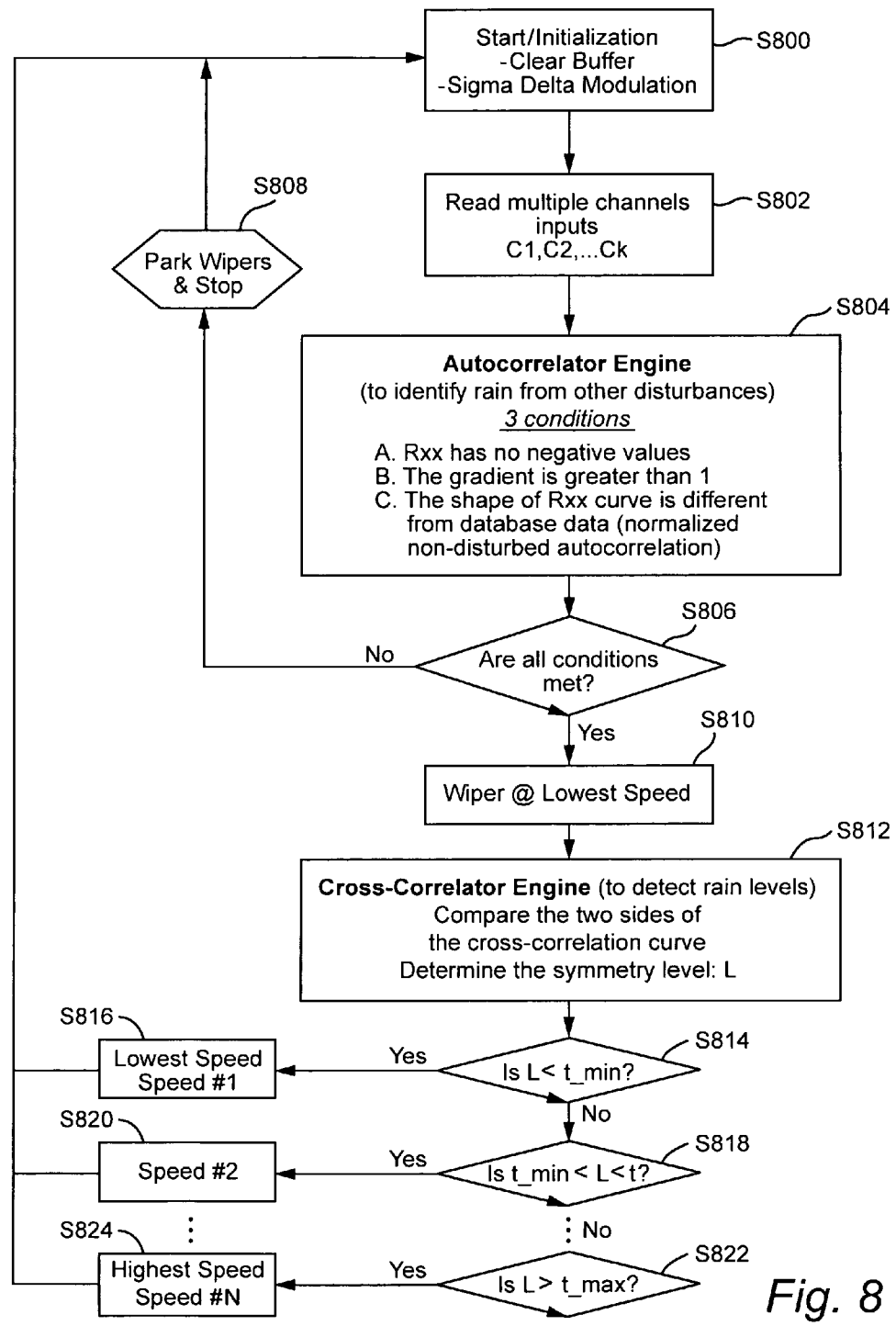
FIG. 8 is an exemplary flowchart showing how autocorrelation and cross-correlation data can be used to control wipers according to an example embodiment of this invention, which may be used in conjunction with one of more of FIGS. 1-7 and 9-12.

The steps performed by the rain sensor will be described in greater detail in connection with FIG. 8, which is an exemplary flowchart showing how autocorrelation and cross-correlation data can be used to control wipers in certain example embodiments of this invention. In FIG. 8, in step S800 buffers are cleared, and data outputted from the FIG. 4-5 circuit (e.g., from $C_{int}$, or from capacitors C1-C4) is sigma-delta modulated, and is read in S802.

The algorithm for determining whether to engage wipers and, if so, the speed at which to engage wipers begins by autocorrelating the sigma-delta modulated data in step S804. Autocorrelation may be used for analyzing functions or series of values, such as time domain signals. An autocorrelation is the cross-correlation of a signal with itself. Autocorrelation is used for finding repeating or substantially repeating patterns in a signal, such as, for example, determining the presence of a periodic signal buried under noise, identifying the fundamental frequency of a signal that does not actually contain that frequency component but implies within it with many harmonic frequencies, etc. Cross-correlation is a measure of the similarity of two signals, and it is used to find features in an unknown signal by comparing it to a known one; in other words it may be used to perform signal fingerprinting in certain instances. Cross-correlation is a function of the relative time between the signals. In certain example embodiments of this invention, digital signals from any two capacitors (e.g., C1 and C2) are cross-correlated, in close spatial proximity, and the system looks for any degree of correlation at time lags other than a time lag of zero. This spatio-temporal cross-correlation allows the system to extract patterns in how the falling rain is electrically projecting itself over the sensor array. As an example, the system may take the case of rain drops moving over one capacitor C1 at a time t0 and the same drop "ringing" another capacitor C4 (spatially separated by distance L from C1). If the drop moves at an average speed Vi, the time (t0+T), where T=L/Vi, the cross-correlation function will have another extremum or kink. The normalized magnitude of this extremum value may allow the system to determine the degree of rain falling on the sensor.

Each capacitor C1-C4 has an autocorrelation function associated with the digitized Vout resulting from the readout thereof (or the corresponding readout of $C_{int}$). In example embodiments, the autocorrelation function depends on time difference, rather than on actual time. Computing autocorrelations is beneficial because it allows, for example, the deduction of the fundamental frequency irrespective of phase. Autocorrelations are advantageous over other methods, such as Fourier transforms (which may also be used in certain example embodiments of this invention) which provide information about the underlying harmonics only. Thus, the use of autocorrelation of the readouts from capacitors C1-C4 (which as explained above, includes the corresponding readouts from mimicking $C_{int}$) can be used to detect and distinguish between beads of water, dirt, dust, droplets, downpour, etc.

It is noted that herein data from $C_{int}$ is considered to be data from the capacitors C1-C4 because the capacitance $C_{int}$ mimics or substantially mimics the capacitances C1-C4 as explained above. Thus, when we talk about receiving data from the capacitors (e.g., C1-C4), this covers and includes receiving data from capacitance $C_{int}$. In other words, the output from the FIG. 4-5 circuit is considered to be from the capacitors C1-C4, even though it is not taken directly therefrom.

Rain, as a function of time, may be represented by the following formula:

$$b(\vec{r}, t) = \begin{cases} 1 & \text{rain projects electrically} \\ 0 & \text{otherwise} \end{cases}$$

Essentially, b takes on a binary value indicating whether it is raining (1), or not (0). It will be appreciated that b is at least two bits, and that for sigma-delta modulation 24-bits may be used in certain example embodiments. It also will be appreciated that a scale could be introduced, potentially to capture more data related to the voltages in the capacitors C1-C4 (or $C_{int}$).

At the end of a sampling cycle L, for example, the output from the FIG. 4-5 circuit, e.g., from the array of four capacitors C1-C4 (or via $C_{int}$), ranges from 0000 to 1111 in certain example embodiments, using binary digital data. A single bit turned on can initiate a single wipe in certain example instances. In the case when all bits are off (0000) or all bits are on (1111), then no wipes may be initiated in certain example instances, because likely there is nothing on the windshield, the car is completely submerged, etc., since all capacitors in the array would be reading the same which is not consistent with rain falling on a window. Thus, the most probable events where wipers will be needed are those in the range of 0001 to 1110 (i.e., when the output from all capacitors in the array is not the same). When the data falls in this range, or even if it does not fall within this range, correlation functions (auto and/or cross correlation functions) may be performed using the following integral. It will be appreciated that the integral below can be rewritten in other forms, such as, for example, as a summation. The correlations between two drops over a large time period may be computed according to the following formula:

$$R_b(r_1, t; r_2, t_2) = \frac{1}{L}\int_0^L b(r_1, t_1+t)b(r_2, t_2+t)dt$$

$$R_b(r_1, t; r_2, t_2) = R_b(\Delta \vec{r}, \Delta t)$$

where $R_b$ is the correlation of a binary event, given as a function of the resistances $r_i$ at given times $t_i$; and L is a large sampling period during which a burst of data is captured. In certain example embodiments, the sampling period L may be from about 10 to 100 ms, and more preferably from about 20-30 ms, which corresponds approximately to the frequency an average human eye can discern. $R_b$ also is equal to a function of the correlation of the changes in resistances across capacitors $\Delta \vec{r}$ and the change in time. When $\Delta \vec{r} = 0$, the autocorrelation value is determined since data from the same capacitor is being analyzed, and when $\Delta \vec{r} \neq 0$, cross-correlations are computed since correlation is performed on data from different capacitors.

These functions are subject to several example constraints and underlying assumptions. First, $$\Delta \vec{r} = \vec{Vi} \Delta t.$$

This constraint essentially means that a drop of water or the like is moving at a given time scale. Second, $$b(\vec{r}+\vec{Vi}\Delta t, t+\Delta t) = b(\vec{r}, t).$$

This constraint mimics or substantially mimics what happens when drops of water or the like move from one capacitor to another. Thus, the correlation functions might be thought of as discrete steps p in space and T in time. This feature may be mathematically represented as the following equation:

$$R_b(m\vec{p}, nT) = R(\vec{Vi}\Delta t, \Delta t)$$

Figure 9:
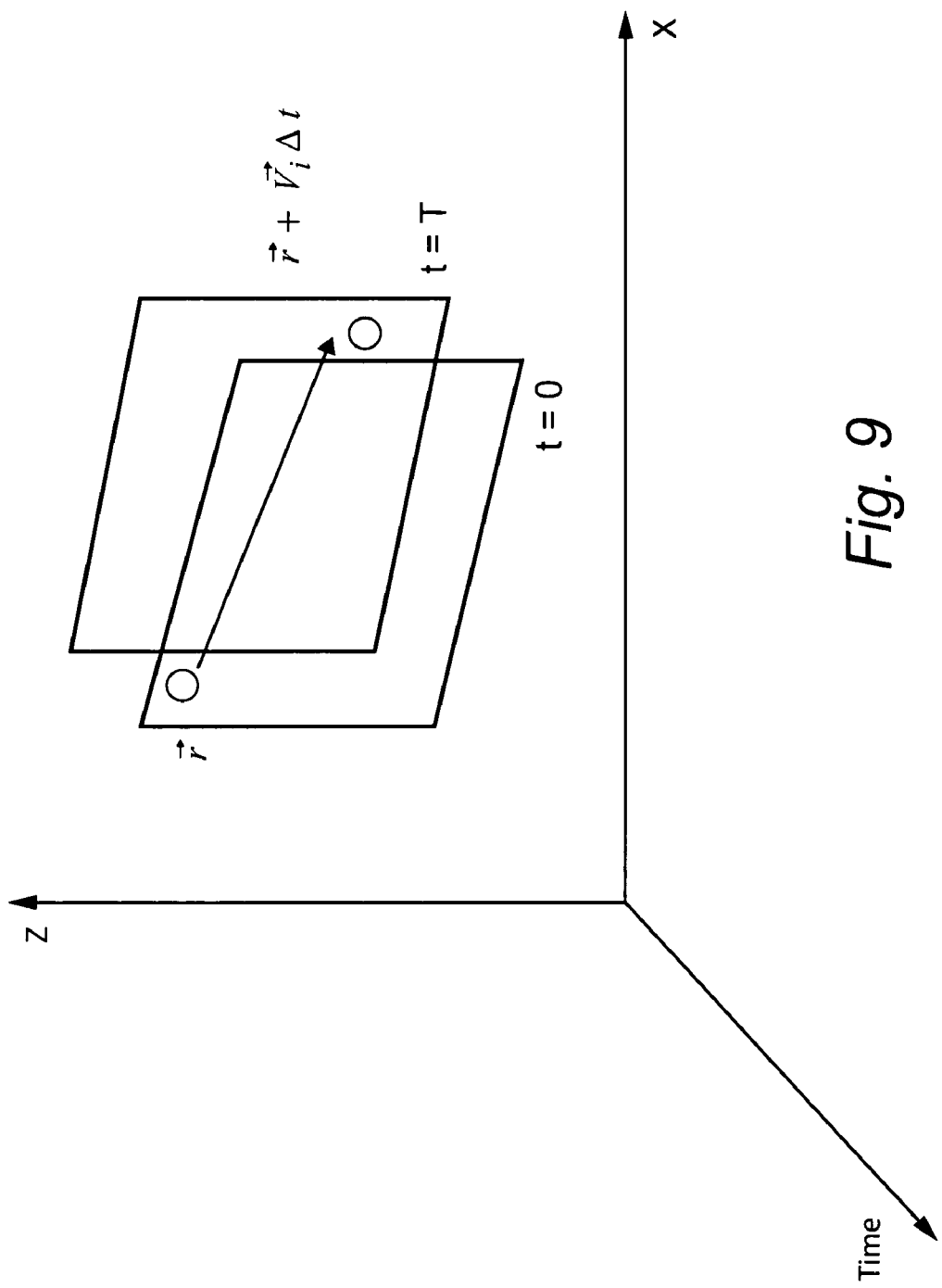
FIG. 9 is an exemplary stylized view of how a rain droplet might travel across a windshield.

Essentially, the left-hand side of the equation establishes a theoretical grid in space and time across which a drop of water or the like moves. For example, FIG. 9 is an exemplary stylized view of how a rain droplet might travel across a windshield. FIG. 9 shows a rain droplet moving across a windshield on the X-Z plane during an initial time period (t=0) and some late quantum of time (t=T). The assumption that drop distribution is uniform over space and time allows the creation of a binary field caused by rain that is in a wide sense stationary. The system also assumes that the temporal correlation between preferred pixels in the same neighborhood is high in the direction of rain. Lastly, the degree of autocorrelation and cross-correlation in time quantifies rain fall and other disturbances.

It will be appreciated that in certain example embodiments, computational time can be saved because of the nature of correlation matrices and the nature of rainfall. For example, correlation matrices may be symmetrical in certain example instances. Additionally, as another example, because rain tends to fall down from the sky and move up along a windshield, it may be sufficient to compare only capacitors that are disposed vertically relative to one another in cross-correlation, while ignoring horizontally adjacent capacitors.

It is noted that while binary data is used in certain example embodiments of this invention, this invention may also utilized grey scale data in certain example instances with respect to outputs from the circuit of FIG. 4-5, or from similar or other suitable circuit(s).

After the autocorrelation has been performed in step S804 (e.g., using the equation (s) discussed above, or some other suitable correlation equation (s)), one or more checks may be performed to enhance the accuracy of the system. Examples of such checks (e.g., if the autocorrelated data Rxx has negative values, if a gradient is greater than one, and/or if the shape of a Rxx curve is different or substantially different from a normalized non-disturbed autocorrelation data stored in memory) are listed in the bottom part of the box for step S804 in FIG. 8. One, two or all three of these checks may be performed.

Figure 10:
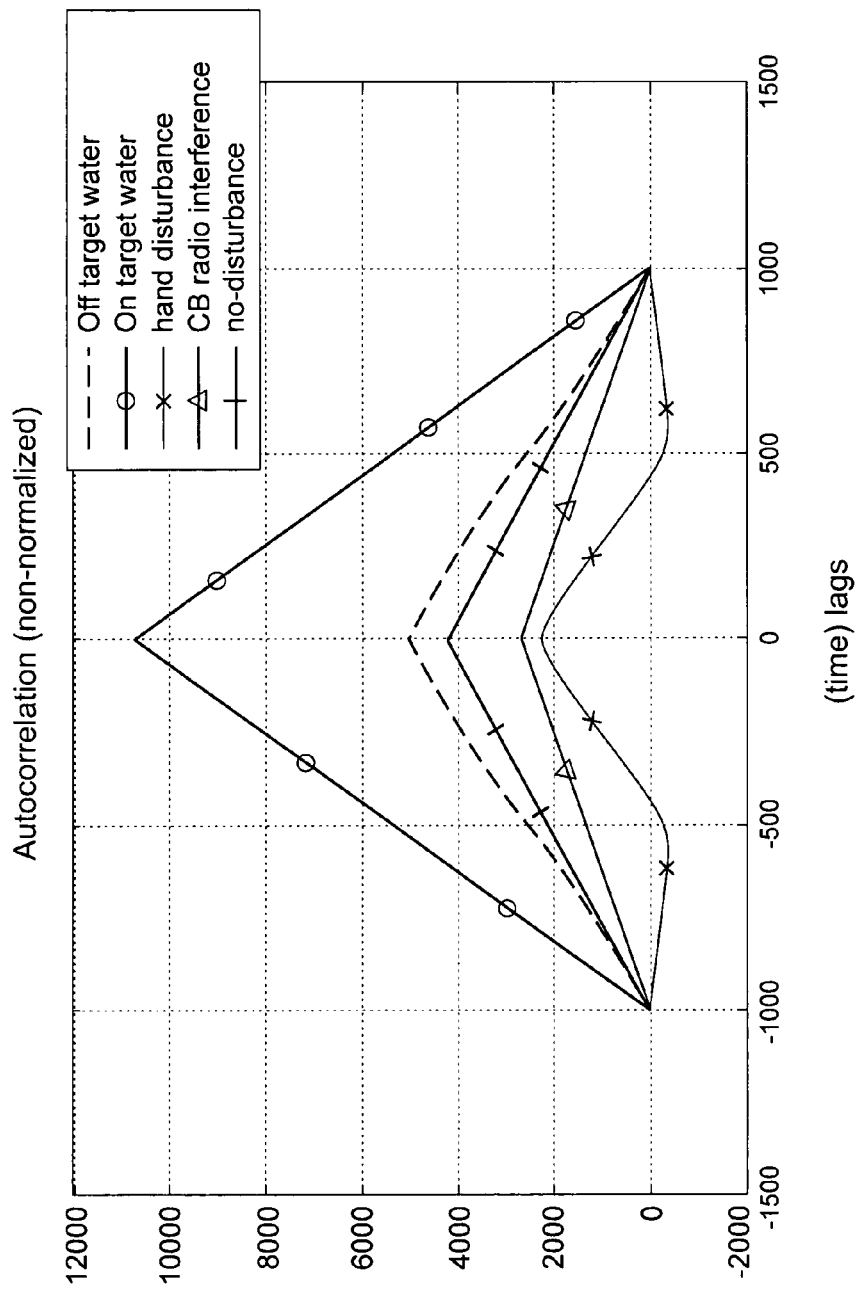
FIG. 10 is an graph plotting example experimentally-obtained maximum values of non-normalized autocorrelations for different disturbances.

For example, one check of the autocorrelation data in step S806 may be to determine whether the autocorrelated data from one or more of the capacitor(s) (C1, C2, C3 and/or C4; or via mimicking $C_{int}$) comprises negative values. For instance, when the autocorrelated data has negative value(s), then the system or method may indicate that it is not raining, may park the wipers, and/or may not actuate windshield wipers (see step S808). This check is for determining, for example, whether a detected disturbance is actually rain. In this respect, FIG. 10 is a graph plotting example experimentally-obtained maximum values of non-normalized autocorrelations for different disturbances. FIG. 10 illustrates that water signals are greater than non-disturbed signals and are positive, and that external interferences such as electromagnetic waves from CB radios and human hand touching of a window tend to be below the no-disturbance levels and may be negative. Thus, to eliminate or reduce false detections due to external disturbances such as, for example, a human hand touching the window, radio signal interference, etc., any signal with negative autocorrelation values is considered a "no-rain" event. It will be appreciated that some example embodiments may consider negative autocorrelation values. Other example embodiments may take other measures to eliminate or reduce false detections due to external interferences by, for example, comparing gradients (e.g., any curve lower or less than the no-disturbance curve/plot of FIG. 10 may be considered a "no-rain" event), shielding capacitors, etc.

A second example check of the autocorrelation data is to check whether a gradient of an autocorrelation curve associated with the autocorrelated data is greater than one; and if not then the system or method may indicate that it is not raining, park the wipers and/or not actuate wipers of the vehicle (see step S808). In this check, the gradient of the normalized autocorrelation of the disturbance is checked. The gradient of the normalized autocorrelation of a non-disturbed signal is close to 1. Measuring the gradient is beneficial because it is not affected by temperature change. Thus, the rain sensor may be substantially immune to false reads due to temperature changes in certain example embodiments of this invention. In certain example instances, gradients less than 1 (or some other predetermined value) may be considered no-rain events.

A third example check of the autocorrelation data is to determine whether there is a match or substantial match between an autocorrelation curve (e.g., signal footprint) associated with the autocorrelated data and one or more predetermined autocorrelation curve(s) (e.g., predetermined footprint) stored in a database and/or memory. When the shape of the autocorrelation curve associated with the autocorrelated data from the FIG. 4-5 circuit is different or substantially different from an autocorrelation curve relating to normalized non-disturbed autocorrelation data, this may be considered a no-rain event and it may be indicated that it is not raining, wipers may be parked, and/or wipers may be not actuated (see step S808). However, when there is a match dr substantial match between the autocorrelation curve associated with the autocorrelated data from the FIG. 4-5 circuit and a predetermined autocorrelation curve associated with moisture such as rain, then it may be indicated that it is raining, wipers may actuated, or kept moving.

In this regard, the shape of the autocorrelation curve may be used to reduce false wipes and/or false detections. In particular, the normalized autocorrelation of a non-disturbed signal is used as a reference. Then, the normalized autocorrelation of each signal captured from the FIG. 4-5 circuit is compared to the reference to identify the closest fingerprint in certain example instances. Generally, the more water present in the sensing area, the larger the difference between the reference signal and the observed signal. In this way, correlation snapshots can be compared to reference snapshots of well-known events such as the presence of rain, dirt, no-disturbance, ice, and so forth. In general, correlation snapshots may be normalized, though the invention is not so limited. Correlation snapshots preferably plot r-values versus quantums of time over a discrete time interval in certain example embodiments of this invention.

In certain example embodiments, when there is a match or substantial match between the autocorrelation curve associated with the autocorrelated data from the FIG. 4-5 circuit and a predetermined autocorrelation curve associated with a non-moisture substance such as dirt, then this may be considered a no-rain event and it may be indicated that it is not raining, wipers may parked and/or not actuated (see step S808).

Thus, it will be appreciated that the shape of the autocorrelation curve resulting from the data output from the FIG. 4-5 circuit (from the capacitors C1-C4, or via $C_{int}$) may be used to reduce false wipes as a third condition. For instance, a normalized autocorrelation curve of a non-disturbed signal may be used as a reference. Then, the normalized autocorrelation of each signal captured from the FIG. 4-5 circuit is compared to the reference to identify the closest fingerprint. Generally, the more water present in the sensing area, the larger the difference between the reference signal and the observed/detected signal. In this way, correlation snapshots can be compared to reference snapshots of well-known events. In general, correlation snapshots preferably are normalized, though the invention is not so limited. Correlation snapshots preferably plot r-values versus quantums of time over a discrete time interval.

A potential problem with capacitive rain sensors is that rapid temperature changes (e.g., due to the radiation absorbing black frit used to cosmetically hide the sensor pattern) change the dielectric "constant" (permittivity) of the glass. This is then registered as a capacitance change and may erroneously be interpreted as a rain signal. However, according to certain example embodiments of this invention, a normalized autocorrelation function is unchanged, or substantially unchanged, for different temperatures even though there may be differences for the non-normalized autocorrelation functions for the different temperatures. Thus, in certain example embodiments of this invention, the sensing system is unaffected or substantially unaffected by temperature changes.

In addition, extremely slow accumulation of water like ultra-fine mist can slowly build up to a level that triggers sensors based on Nyquist rate converters. In the time of observation that concerns human vision (e.g., 30-60 Hz), the autocorrelation function in certain example embodiments of this invention is able to discriminate between the ultra-slow accumulation of dew or condensation and normal mist and rain.

Figure 11A:
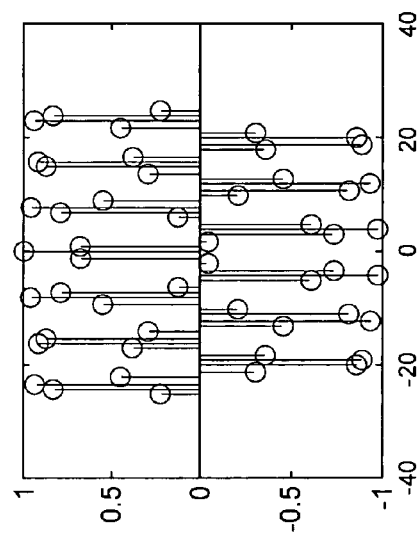
FIG. 11A is an example experimentally-obtained autocorrelation snapshot indicative of heavy rain.
Figure 11C:
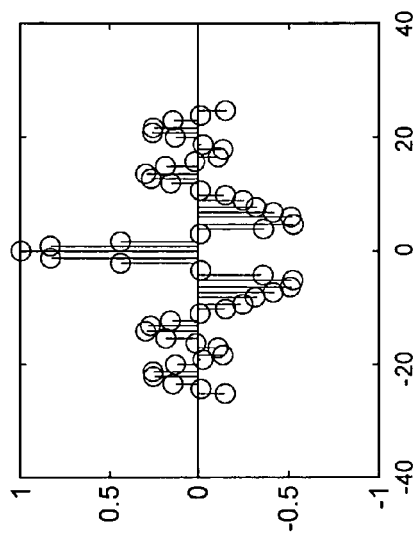
FIG. 11C is an example experimentally-obtained autocorrelation snapshot indicative of CB radio interference.
Figure 11B:
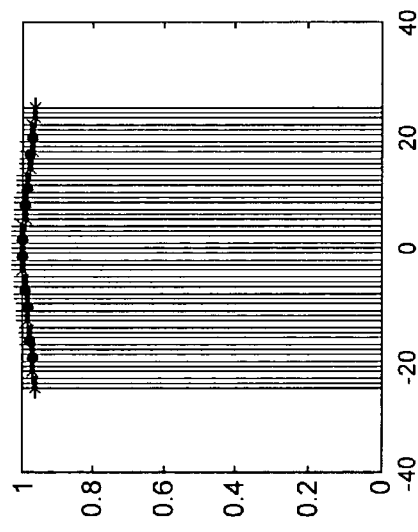
FIG. 11B is an example experimentally-obtained autocorrelation snapshot indicative of a light mist.
Figure 11D:
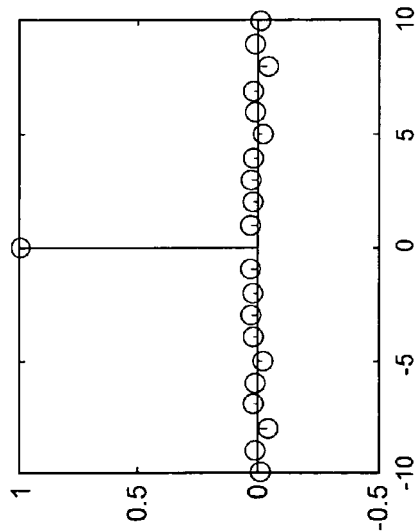
FIG. 11D is an example experimentally-obtained autocorrelation snapshot indicative of a grounded body with a voltage.

FIGS. 11A-11D provide sample experimentally-obtained correlation snapshots. These correlation snapshots, or fingerprints/footprints of an event, can be stored as reference footprints/fingerprints or correlation curves. Observed/detected correlation snapshots (e.g., autocorrelation curves) can be compared to these reference footprints or fingerprints to determine the type of event occurring. For instance, FIG. 11A is an experimentally-obtained autocorrelation snapshot indicative of heavy rain. FIG. 11B is an experimentally-obtained autocorrelation snapshot indicative of a light mist. FIG. 11C is an experimentally-obtained autocorrelation snapshot indicative of CB radio interference. FIG. 11D is an experimentally-obtained autocorrelation snapshot indicative of a grounded body with a voltage. The patterns or data of FIGS. 11A-11D may be called predetermined footprints or fingerprints in certain instances, and it will be appreciated that other types and shapes of predetermined footprints may also be used in different embodiments of this invention. It will be appreciated that these fingerprints/footprints are provided as non-limiting examples and reflect experimentally-obtained data. Actual events may differ in various characteristics. Thus, in certain example embodiments of this invention, when it is determined that there is a match or substantial match between the autocorrelation curve associated with the autocorrelated data from the FIG. 4-5 circuit and a predetermined non-moisture autocorrelation curve such as that of FIG. 11C or FIG. 11D, then this may be considered a no-rain event and it may be indicated that it is not raining, wipers may parked and/or not actuated (see step S808). However, in certain example embodiments of this invention, when it is determined that there is a match or substantial match between the autocorrelation curve associated with the autocorrelated data from the FIG. 4-5 circuit and a predetermined moisture-related autocorrelation curve such as that of FIG. 11A or FIG. 11B, then this may be considered a rain event and it may be indicated that it is raining, wipers may actuated and/or kept moving. In addition to the predetermined autocorrelation curves of FIGS. 11A-11D, other reference fingerprints may be stored and/or compared with observed correlation snapshots in other example embodiments of this invention.

Turning back to FIG. 8, in step S806 it is determined whether each of the three conditions set forth in the bottom portion of the S804 box is met. In particular, it is determined in S806 whether each of the following is met: (a) the autocorrelated data has no negative values; (b) a gradient of an autocorrelation curve associated with said autocorrelated data is greater than a predetermined value such as one; and (c) the shape of the autocorrelation curve associated with the autocorrelated data from the FIG. 4-5 circuit is different than a predetermined autocorrelation curve associated with non-disturbed autocorrelation data. If they are not all met, this is an indication of a non-rain event and the process moves to step S808 where the vehicle wiper(s) are parked (if they were moving) or are kept off, and begins initialization S800 again. However, if all of these requirements are met in S806, then the process moves to S810 and the vehicle's wipers (e.g., windshield wipers) are activated at their lowest speed.

Figure 13:
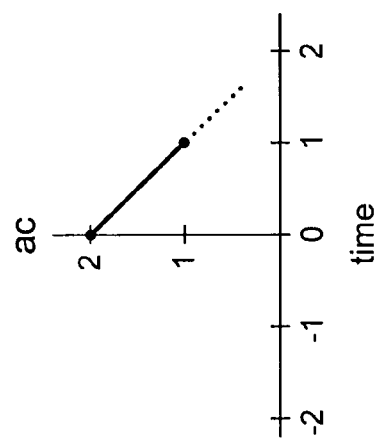
FIG. 13 is an example of autocorrelation according to an example embodiment of this invention.
Figure 15:
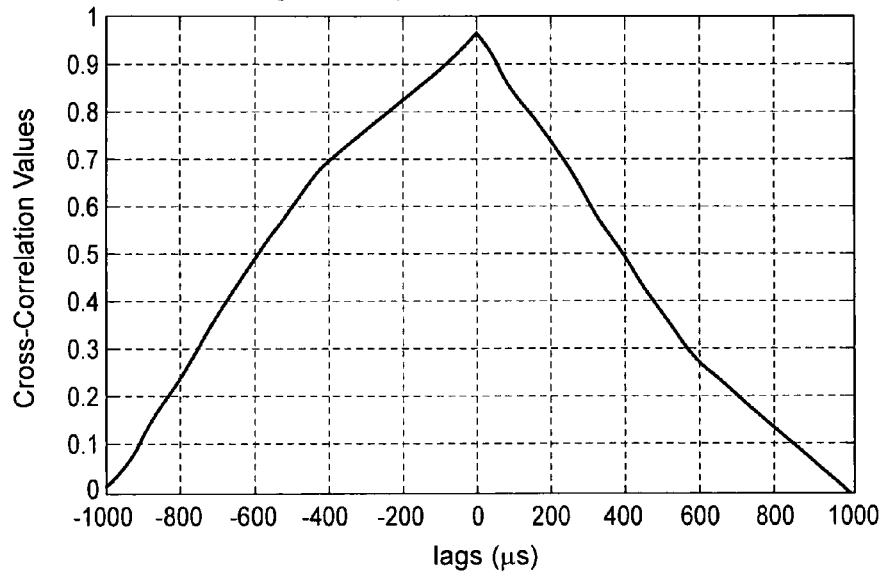
FIG. 15 is a crosscorrelation graph, plotting crosscorrelation values versus time lags (the time lags are in terms of microseconds in the time domain) according to an example of this invention, using certain signals from FIG. 14.
Figure 16:
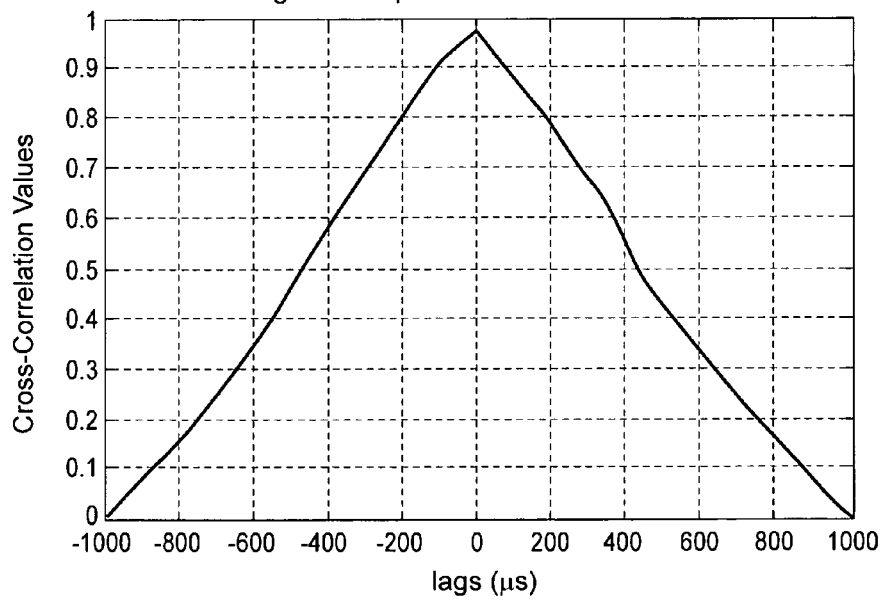
FIG. 16 is a crosscorrelation graph, plotting crosscorrelation values versus time lags (the time lags are in terms of microseconds in the time domain) according to an example of this invention, using certain signals from FIG. 14.
Figure 17:
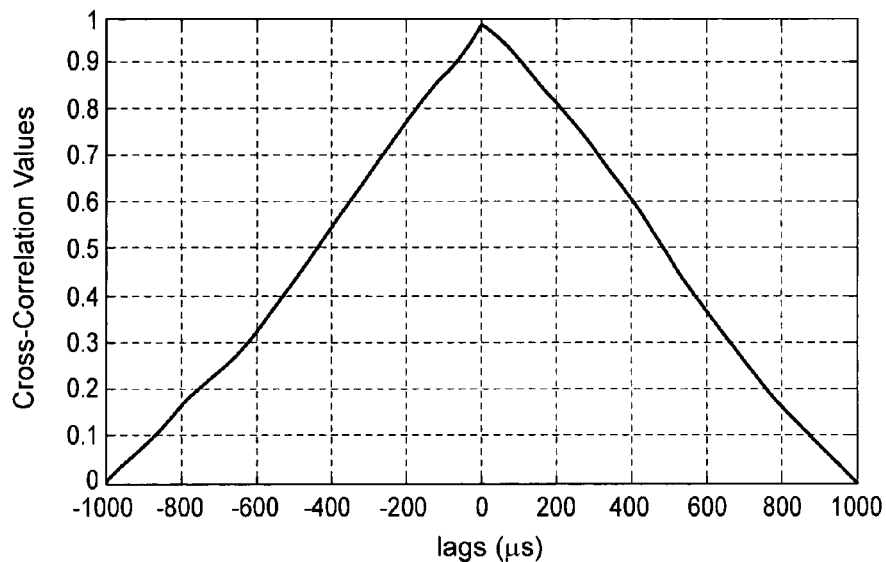
FIG. 17 is a crosscorrelation graph, plotting crosscorrelation values versus time lags (the time lags are in terms of microseconds in the time domain) according to an example of this invention, using certain signals from FIG. 14.
Figure 18:
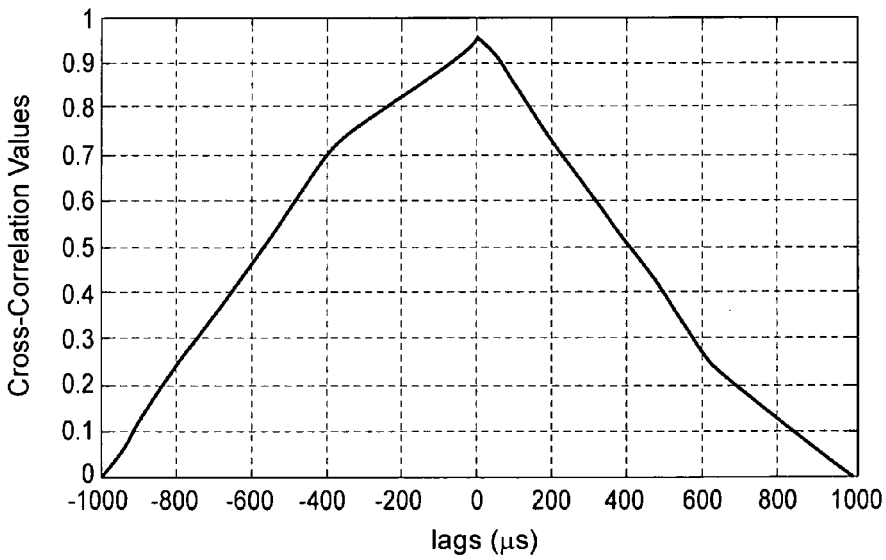
FIG. 18 is a crosscorrelation graph, plotting crosscorrelation values versus time lags (the time lags are in terms of microseconds in the time domain) according to an example of this invention, using certain signals from FIG. 14.
Figure 19:
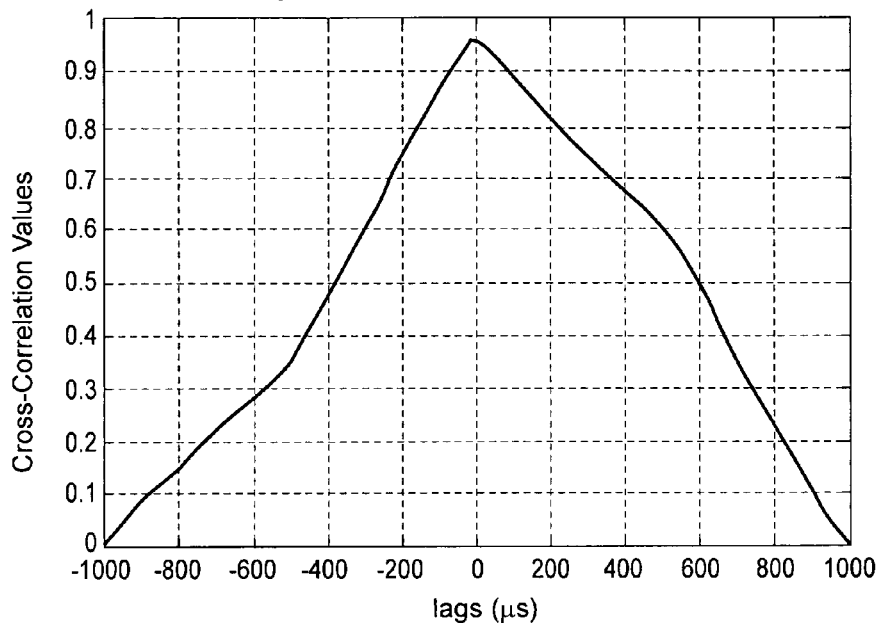
FIG. 19 is a crosscorrelation graph, plotting crosscorrelation values versus time lags (the time lags are in terms of microseconds in the time domain) according to an example of this invention, using certain signals from FIG. 14.
Figure 20:
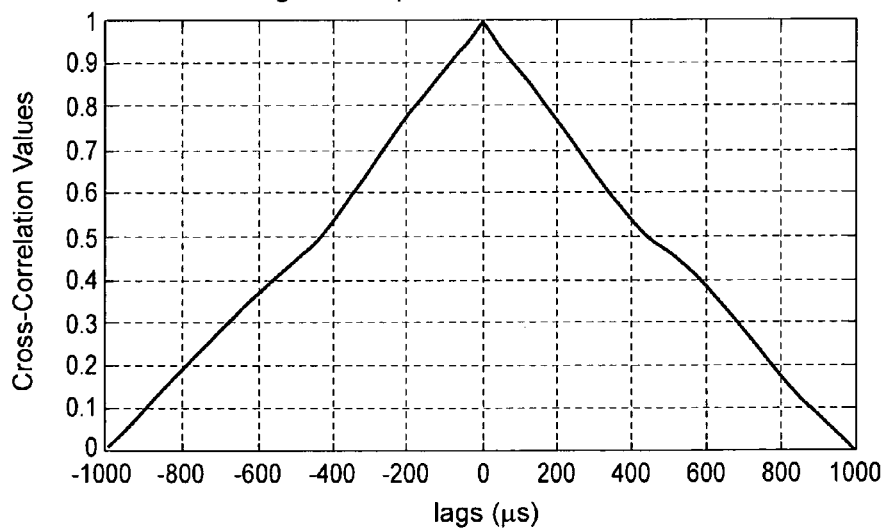
FIG. 20 is a crosscorrelation graph, plotting crosscorrelation values versus time lags (the time lags are in terms of microseconds in the time domain) according to an example of this invention, using certain signals from FIG. 14.
Figure 21:
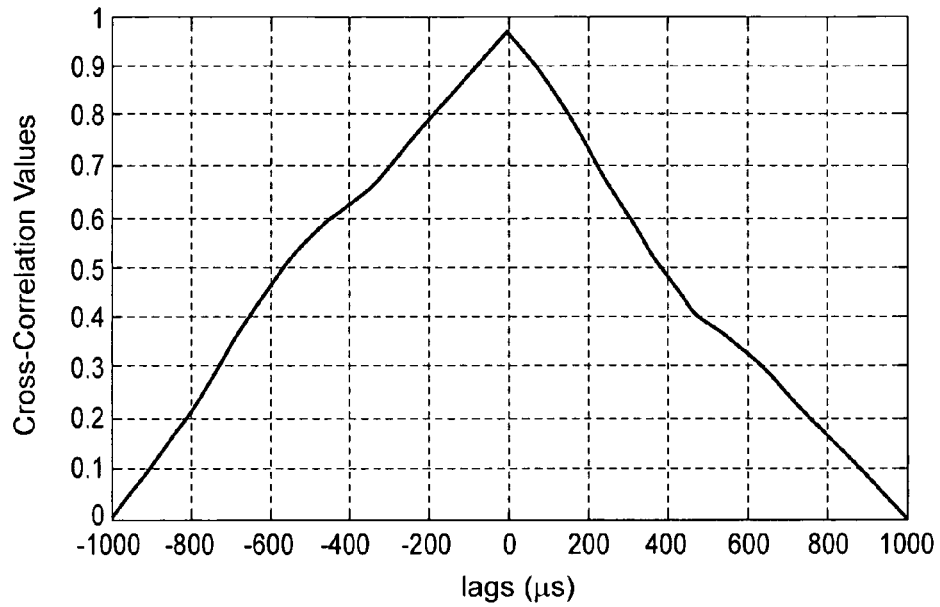
FIG. 21 is a crosscorrelation graph, plotting crosscorrelation values versus time lags (the time lags are in terms of microseconds in the time domain) according to an example of this invention, using certain signals from FIG. 14.
Figure 22:
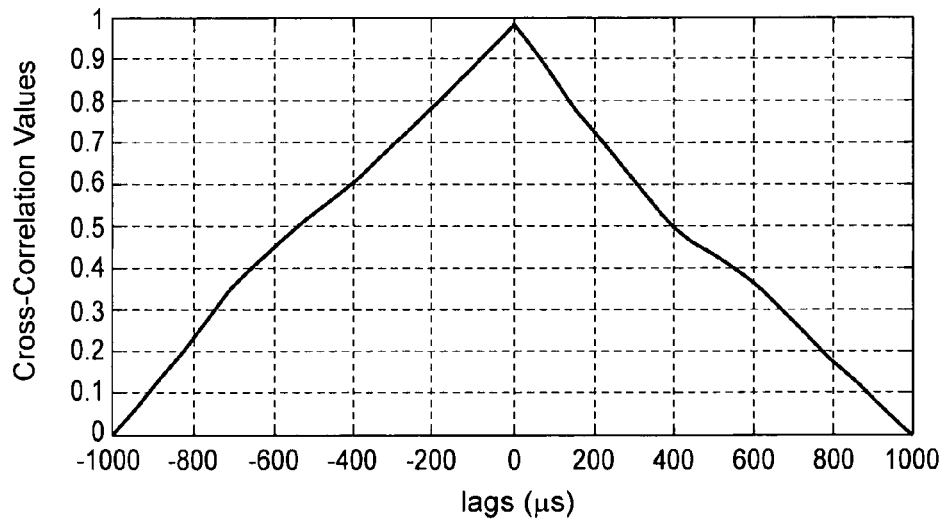
FIG. 22 is a crosscorrelation graph, plotting crosscorrelation values versus time lags (the time lags are in terms of microseconds in the time domain) according to an example of this invention, using certain signals from FIG. 14.
Figure 23:
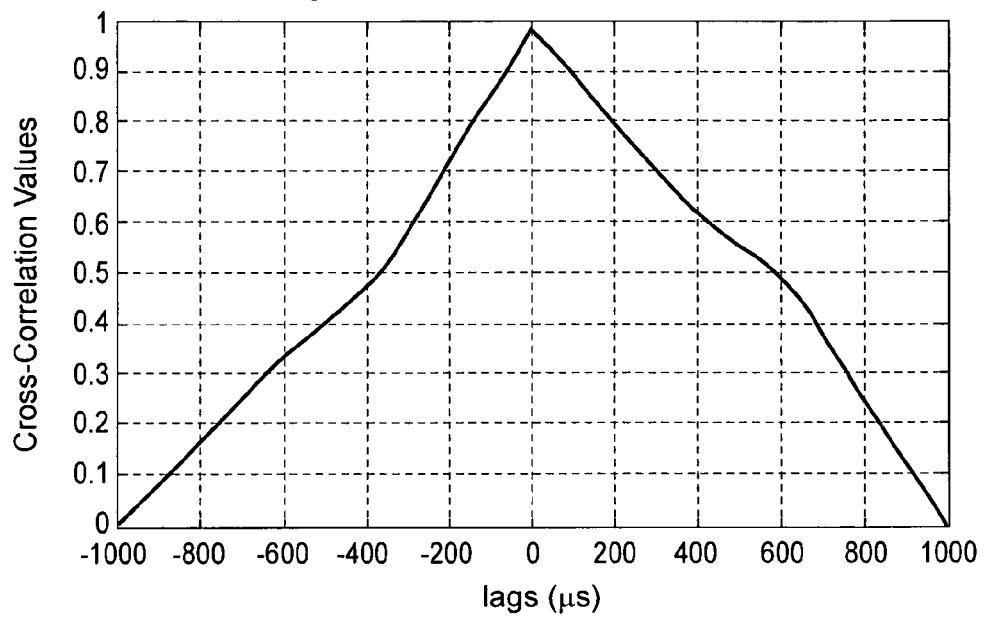
FIG. 23 is a crosscorrelation graph, plotting crosscorrelation values versus time lags (the time lags are in terms of microseconds in the time domain) according to an example of this invention, using certain signals from FIG. 14.
Figure 24:
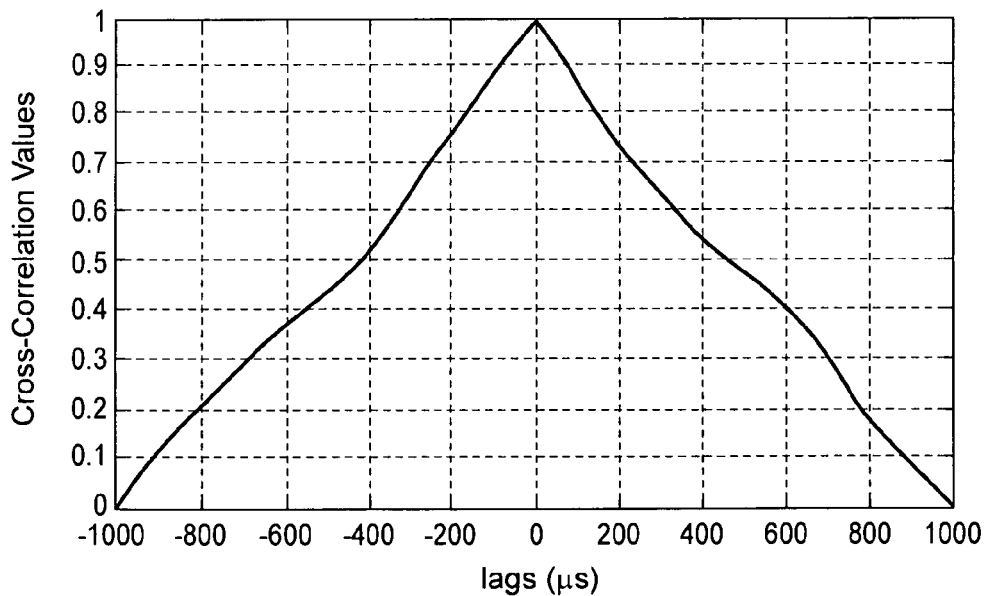
FIG. 24 is a crosscorrelation graph, plotting crosscorrelation values versus time lags (the time lags are in terms of microseconds in the time domain) according to an example of this invention, using certain signals from FIG. 14.

For purposes of example only, and understanding, FIG. 13 illustrates an example of autocorrelation. In FIG. 13, the values from (or relating to) sensing capacitor C1 are, at sequential times —t2, −t1, t0, t1, t2 and t3 are 0, 0, 1, 1, 0 and 0, respectively. Autocorrelation for time 0 (aco) is determined by multiplying the values relating to C1 in a non-offset manner, and then adding or summing the results. It can be seen in FIG. 13 that aco is equal to 2 in this instance. Thus, on the autocorrelation graph at the bottom of FIG. 13, an entry in the graph at time 0 is made for an autocorrelation value of 2. Note that the autocorrelation graph at the bottom of FIG. 13 is similar, but simpler, that the autocorrelation graph in FIG. 10 and the autocorrelation values may be obtained for FIG. 10 in a like manner. Next, still referring to FIG. 13, autocorrelation is performed using the capacitance values relating to C1 for the next point in time to obtain autocorrelation value ac1. This next autocorrelation value (ac1) is obtained by shifting the bottom row sequence of values for C1 relative to the top row as shown in FIG. 13, and then multiplying the values in the rows which line up with each other and summing the results. FIG. 13 illustrates that ac1 is equal to 1 for time 1. Thus, this autocorrelation value of 1 for time t1 may be entered in the graph at the bottom of FIG. 13 and a line is drawn between the two entered data points for purposes of example and understanding. The, for the next time value (or lag), the bottom row is again shifted another segment over relative to the top row and the process repeated, and so forth. It can be seen that the autocorrelation plots in FIG. 10 may be obtained in a similar manner. In FIG. 13, it will be appreciated that cross-correlation may be performed by replacing the C1-related values in the bottom row with values from or related to another capacitor such as C2 (or C3 or C4).

Examining autocorrelation and/or cross-correlation also can help distinguish between, for example, light rain and heavy rain. For example, if only the autocorrelation in time is high (and crosscorrelation is low), then there probably is only light rain. FIG. 12A is an exemplary correlation matrix showing light rain. Of note in FIG. 12A is that the correlations between C1 and C1, C2 and C2, C3 and C3, and C4 and C4 (these are autocorrelations) over a given time period are high, while the rest of the correlations (the cross-correlations) are low. By hypothesis and confirmed experimental data, a matrix of this sort would indicate a light rain.

On the other hand, if both autocorrelation and cross-correlation in time between capacitor signals are high, there is probably fast rain. FIG. 12B is an exemplary correlation matrix showing heavy rain. In FIG. 12B, not only are the autocorrelations of individual capacitors high (i.e., the autocorrelations are the correlations between C1 and C1, C2 and C2, C3 and C3, and C4 and C4), cross-correlations between different capacitors also are generally high (the correlations in FIG. 12B going diagonally from the upper-left to the bottom-right are the autocorrelations, and the rest are the cross-correlations). By hypothesis and confirmed experimental data, a matrix of this sort would indicate a fast rain. The degree of cross-correlation can be quantized to determine the relative speed of the rain. This data can, in turn, be used to trigger various wiper speeds, as appropriate for the speed of the rain. For instance, the more cross correlations that are high, the higher the wiper speed to be used.

More systematically, in step S812, cross-correlations are computed (correlations between data relating to different capacitors), and the two sides of the cross-correlation curve are used to determine a symmetry level L. If the symmetry level is lower than a predefined threshold $t_{min}$, step S814 directs the system to step S816 where wipers are activated at the lowest speed, and the system is returned to initialization step S800. If the symmetry level is greater than $t_{min}$ but less than an arbitrary value t, step S818 directs the system to step S820 where wipers are activated at a faster or medium speed, and the system is returned to initialization step S800. It will be appreciated that a plurality of arbitrary values $t_i$ may be specified, and a symmetry level falling between $t_i$ and $t_{i+1}$ will activate an appropriate corresponding wiper speed and then return the system to initialization step S800. Finally, in step S822, if the symmetry level is above a predefined level $t_{max}$, step S822 directs the system to step S824 where wipers are activated at the highest speed, and the system is returned to initialization step S800. Thus, correlations from the data output from the FIG. 4-5 circuit can be used to adjust wiper speed. In certain example embodiments, the more cross correlations that are high, the higher the wiper speed to be used due to the likelihood of heavier rain.

For purposes of example and understanding, FIGS. 14-24 illustrate examples of cross-correlation performed according to certain example embodiments of this invention. FIG. 14 sets forth cross-correlation data in certain example instances, whereas FIGS. 15-24 illustrate cross-correlation graphs of certain of the data from FIG. 14 where rain is detected. In FIGS. 15-24, each lag on the horizontal axis is one microsecond (1 μs) for purposes of example, and sampling was performed every one microsecond. As explained above with respect to FIG. 13, in FIGS. 15-24 at time=0 (lag 0), there is no shift in time of the values from the different capacitors being correlated. FIG. 14 illustrates that when rain was present (see signals S1-S5 and W1-W5), the delta signals relating to autocorrelation were high. FIGS. 15-24 are cross-correlation plots relating to these signals. It is helpful to look for symmetry between the plots on the left and right hand sides of each of FIGS. 15-24 (one side of zero is compared to the other side of zero). Generally speaking, if there is symmetry about the zero lag axis, there is not much cross-correlation which indicates that the detected rain is not very hard. However, if there is asymmetry about the zero lag axis, then this means more cross-correlation and indicates that the rain is hard or harder. For example, note the asymmetry in FIGS. 18, 19 and 23 about the zero lag axis due to the bumps or valleys on one or both sides. More cross-correlation indicates that the rain drops are moving from one capacitor's sensing area to another capacitor's sensing area. In this respect, each interaction of a rain drop and the surface of a windshield has its own correlation signature in the time domain. High cross-correlation indicates that the same drop is being detected at different capacitors, at different points in time (e.g., see FIG. 9 also). It is noted that the lower case "t" in FIG. 9 is the same as the lags axis in FIGS. 15-24.

Thus, it will be appreciated that certain example embodiments of this invention provide a moisture sensor (e.g., rain sensor) that can detect rain or other material on a vehicle window or other type of window or sheet/surface, without the need for a reference capacitor. Spatial temporal correlation may be used. All capacitors, or a plurality of capacitors, in the sensing array may be identical or substantially identical in shape in certain example embodiments. For purposes of example, at a given point in time (e.g., t1), the system may compare C1-relates values with C2 related values, and/or other capacitor related values. For this time t1, the system may also compare C1-related values with itself (autocorrelation), and may also compare autocorrelation for C1 with autocorrelation for C2 and/or other sensing capacitor(s).

FIGS. 4-5 illustrate switches for selectively coupling the various capacitors C1-C4 to the rest of the circuit, and FIG. 26 illustrates a multiplexer in this respect. The circuits shown in FIGS. 4-5 and/or 26 may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time. An example non-limiting switching circuit for selective coupling the read-out electronics to one or more of capacitors C1-C4 as needed or as desired in discussed below in connection with FIG. 31. The FIG. 31 switching circuit, or the like, may or may not be used instead of the switches shown in FIGS. 4-5 and/or the multiplexer shown in FIG. 26.

Figure 31:
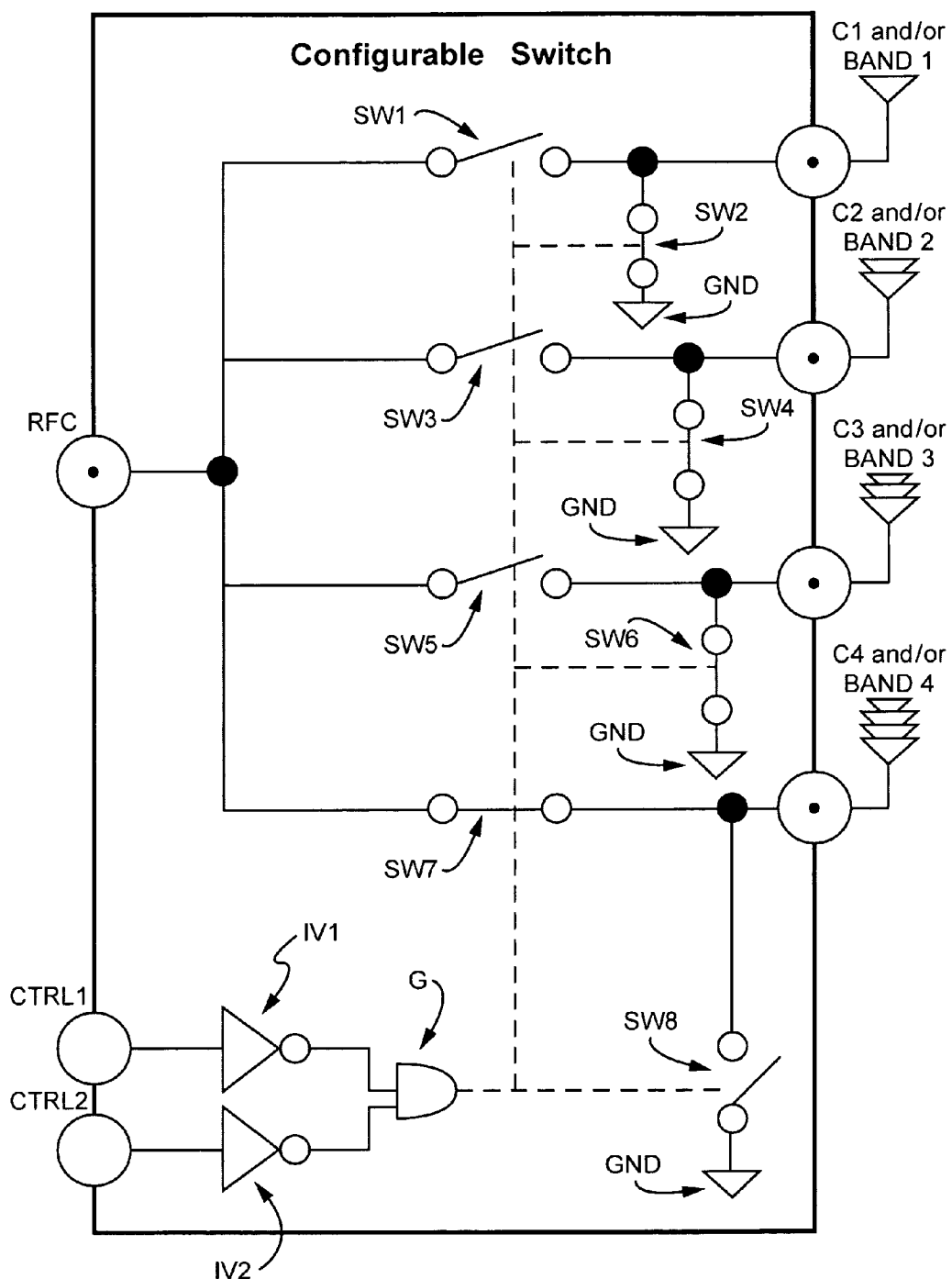

FIG. 31 illustrates an example switching circuit for selectively coupling or switching between different sensing capacitors C1-C4 or different combinations thereof, in order to change the sensing field being analyzed and/or change the feature being searched for. Thus, the FIG. 31 switching circuit allows the sensing field(s) and/or system to be selectively reconfigurable in certain example embodiments of this invention. For example, in certain example embodiments, the switching circuit may selectively switch between: (a) capacitor(s) (e.g., C1) for detecting rain on an exterior surface of the window, and (b) capacitor(s) (e.g., one or more of C2, C3 and/or C4) for detecting one or more of ice on an exterior surface of the window, mist on an exterior surface of the window, and/or moisture on an interior surface of the window. The read-out circuit(s) may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time; the switching circuit of FIG. 31 permits each of these possibilities to be realized and selectively caused as desired. Thus, the switching circuit of FIG. 31 may be advantageous in that it may permit the system to be selectively adjusted, via the sensing field, in order to focus on different types of elements (e.g., rain, ice, mist, etc.) at different points in time. Capacitors C1-C4 may or may not have the same fractal pattern or geometry, and may or may not be of different shapes and/or sizes in different instances.

The switching circuit of FIG. 31 includes a power source connection at RFC, control connections at CTRL1 and CTRL2, inverters IV1 and IV2, AND gate G, and switches SW1, SW2, SW3, SW4, SW5, SW6, SW7 and SW8. The switches SW1-SW8 may be microelectromechanical (MEM) switches where application of voltage to the MEM causes the switch to be actuated, or any other sort of suitable switch in different instances. In this example embodiment, each capacitor has two switches associated therewith. For example, sensing capacitor C1 (and/or Band 1 if the sensing device is an antenna instead of a capacitor) has switches SW1 and SW2 associated therewith, sensing capacitor C2 (and/or Band 4 if the sensing device is an antenna instead of a capacitor) has switches SW3 and SW4 associated therewith, sensing capacitor C3 (and/or Band 4 if the sensing device is an antenna instead of a capacitor) has switches SW5 and SW6 associated therewith, and sensing capacitor C4 (and/or Band 4 if the sensing device is an antenna instead of a capacitor) has switches SW7 and SW8 associated therewith. In FIG. 31, for purposes of example, switches SW2, SW4, SW6 and SW7 are illustrated in the closed position, where switches SW1, SW3, SW5 and SW8 are illustrated in the open position.

Switches SW2, SW4, SW6 and SW8 are provided for selectively coupling the capacitors C1-C4 (and/or Bands 1-4) to ground GND. In certain example embodiments, when a given capacitor is coupled to the read-out circuitry (e.g., C4 is coupled to the read-out circuitry in FIG. 31 because switch SW7 is closed), that capacitor is decoupled from ground GND by opening its ground switch (e.g., ground switch SW8 is open in FIG. 31). However, when a given capacitor(s) is not coupled to read-out circuitry (e.g., capacitors C1, C2 and C3 are not coupled to read-out circuitry in FIG. 31 because read-out switches SW1, SW3 and SW5 associated therewith are open), that capacitor is grounded by closing its ground switch (e.g., ground switches SW2, SW4 and SW6 are closed in order to ground C1, C2 and C3, respectively, in FIG. 31). Grounding of capacitors not currently being read out is advantageous in that it permits noise and/or other problematic signals from interfering with the read-out circuitry or the overall switching circuit.

Still referring to FIG. 31, for purposes of example and without limitation, let us consider an example situation where capacitor C1 designed (e.g., shaped) and positioned for sensing rain on an exterior surface of the window (e.g., windshield), capacitor C2 is designed and positioned for sensing ice on an exterior surface of the window, capacitor C3 is designed and positioned for sensing mist or fog on an exterior surface of the window, and capacitor C4 is designed and positioned for sensing condensation/moisture on an interior surface of the window (e.g., if C4 detects such condensation and/or moisture on the interior surface, then a defroster may be turned on automatically or otherwise in order to remedy the same). In certain example such instances, each of the fractal capacitive sensors C1-C4 may have a different fractal pattern and/or shape, and/or a different orientation/direction. The switching circuit, in order to focus the read-out circuitry on detecting rain on an exterior surface of the window, can couple capacitor C1 to the read-out circuitry and isolate capacitors C2-C4 from the read-out circuitry; this can be done by sending control signals CTRL1 and CTRL2 which cause switches SW1, SW4, SW6 and SW8 to close and switches SW2, SW3, SW5 and SW7 to open. As another example, the switching circuit, in order to focus the read-out circuitry on detecting condensation and/or moisture on an interior surface of the window, can couple capacitor C4 to the read-out circuitry and isolate capacitors C1-C3 from the read-out circuitry; this can be done by sending control signals CTRL1 and CTRL2 which cause switches SW2, SW4, SW6 and SW7 to close and switches SW1, SW3, SW5 and SW8 to open as shown in FIG. 31. As another example, the switching circuit, in order to focus the read-out circuitry on detecting mist and/or fog on an exterior surface of the window, can couple capacitor C3 to the read-out circuitry and isolate capacitors C1-C2 and C4 from the read-out circuitry; this can be done by sending control signals CTRL1 and CTRL2 which cause switches SW2, SW4, SW5 and SW8 to close and switches SW1, SW3, SW6 and SW7 to open. As yet another example, the switching circuit of FIG. 31, in order to focus the read-out circuitry on both detecting ice and rain on an exterior surface of the window, can couple capacitors C1-C2 to the read-out circuitry and isolate capacitors C3-C4 from the read-out circuitry; this can be done by sending control signals CTRL1 and CTRL2 which cause switches SW1, SW3, SW6 and SW8 to close and switches SW2, SW4, SW5 and SW7 to open. It is also possible in certain example instances to couple all capacitors C1-C4 to the read-out circuitry, in which case switches SW1, SW3, SW5 and SW7 would be closed and switches SW2, SW4, SW6 and SW8 would be opened.

It will be appreciated that the switching circuit of FIG. 31 may or may not be used in combination with any other example embodiment discussed herein.

Moreover, it is possible that capacitors C1-C4 in connection with the FIG. 31 embodiment may be replaced with antennas such as fractal based antennas having respective Bands (see Bands 1-4 in FIG. 31). Thus, in this situation, the circuit of FIG. 31 would be able to selectively reconfigure fractal-based antennas of different bands in order to selectively change the band(s) being read out by the read-out circuitry. In such example instances, the read-out circuitry may be used to detect and/or process incoming waves such as AM, FM, Bluetooth, GPS, VHF, and/or UHF signals.

As is clear from the description provided above, certain example embodiments disclosed above relate to a fractal capacitor based rain sensor. Such capacitors allow for higher capacitance per unit area by using lateral fringing fields. As described in detail above, the fringing fields emanating at the surface of the glass may be used to detect moisture, debris, and/or the like. The amount of lateral fringing is proportional to the periphery, and thus the perimeter, of the structure. As noted above, such a fractal capacitor based rain sensor may be printed on glass using, for example, silver frit, which may be located on any one of surfaces 2, 3, and 4 of the windshield. Such arrangements are shown in, and described in connection with, FIGS. 1(b)-1(f).

Placing the pattern on surface 4 is practical and fairly easy to implement using conventional windshield manufacturing techniques. However, in practice, positioning the pattern here typically requires that springy contacts be used to connect the capacitors to the read-out electronics and computing circuitry. This design approach has proven to be effective despite several challenges. For example, first, a hermetic seal sometimes is required to decouple the condensation effects on surface 4 inside the vehicle. Second, there often may be inherent mechanical vibrations at the contact pads. Third, the contacts may be subject to corrosion.

The autocorrelation techniques described above help to overcome the first challenge, e.g., without the use of a hermetic seal. The second and third challenges may be overcome by using gold-coated spring loaded pins. However, this solution implies that such systems, if not properly mechanically designed, could be affected by vibrations at the contacts, e.g., creating minute changes in capacitance values while the vehicle is moving, for example. More generally, though, mechanically induced vibrations may, in turn, translate into capacitive noise that can affect the ultimate sensitivity of the rain sensor.

As such, although the example arrangements and design approaches described above have been successful, further improvements are still possible. For example, the above-noted potential challenges may be addressed in certain example embodiments by providing an integrated capacitive-based moisture and/or debris sensor having embedded electronics located on a flexible printed circuit board (PCB). In brief, the sensor may comprise an array of fringe effect capacitors, which may be screen printed, etched directly, or otherwise located, on a flexible PCB in accordance with certain example embodiments. The flexible PCB, in turn, may include the read electronics components. Once the sensor array is formed on the flexible PCB, the assembly may be glued, laminated directly, or otherwise located onto the windshield. In certain example embodiments, the flexible PCB and sensor array assembly may be located on surface 4, whereas in certain example embodiments, the flexible PCB and sensor array assembly may be located between surfaces 2 and 3.

In certain example embodiments, the flexible PCB and sensor array assembly may comprise a multi-layer, distributed array of capacitors, stacked on top of each other, and electrically isolated and shielded from each other. In certain example embodiments, such an arrangement advantageously may be made compactly, as the length of the excitation and return lines to the capacitors may be reduced while all electronics required, in turn, may be embedded on the sensor.

As alluded to above, in certain example embodiments, the flexible PCB may be used to mechanically support and/or electronically connect electronic components using conductive pathways and/or traces, which may be etched from copper sheets laminated onto a non-conductive substrate. A flexible PCB generally comprises a flexible polymer film laminated to a thin sheet of copper that is etched to produce a circuit pattern. Patterns may be created on one or both sides of the film, and interconnections may be achieved, e.g., via plated through-holes, providing enhanced adaptability between component parts. A polymer overcoat may be added to insulate and/or environmentally seal the circuit.

One example of a flexible polymer film that may be used in connection with the flexible PCBs of certain example embodiments is Kapton®. Kapton® has a high heat resistance, is dimensionally stable, and has good dielectric strength and flexural capabilities. In general, these characteristics of the raw material help the flexible circuit maintain a high degree of durability and also help it to survive hostile environments. Of course, the flexible PCBs of certain example embodiments may include any suitable polymer film.

The flexible PCBs of certain example embodiments also may combine several single and/or double-sided circuits with complex interconnections, shielding surface mounted devices in a multi-layer design. Such multi-layer designs optionally may be combined with rigid circuit boards in certain example embodiments, e.g., to create a rigid/flexible circuit capable of supporting devices as, and when, needed.

Certain example embodiments may lead to one or more of the following and/or other advantages. First, it may be possible to more precisely place the complete sensor assembly on the windshield. That is, the flexural capacity of the polymer may allow the sensor pattern to conform to curvatures of the windshield, with reduced (e.g., free from) moving parts. Second, laminating, gluing, or otherwise connecting the flexible PCB to the windshield may reduce the influence of interior water condensation (and/or other moisture or debris) on the "wet" capacitors.

Third, placing the "wet" and "dry" capacitors on separate layers and each facing away from each other allows the sensor to discriminate between outside and inside conditions. This may be used to take more appropriate actions, e.g., to cause wipes when water is detected on the exterior windshield by the "wet" capacitors whereas defogging may be caused when the "dry" capacitors read a threshold value.

Fourth, having both sets of capacitors next to each other may allow for the effects of rapid temperature changes or exposure to EMI to be identified. Random EMI, for example, will simultaneously have very similar signatures on both the "dry" and "wet" capacitors. Such signatures may be differentiated with either external rain events or interior fogging, for example, Fifth, and as above, the sensor may comprise a plurality of modules, including a sigma-delta analog-to-digital channel converter, a microprocessor unit with a memory (e.g., SRAM and/or Flash), and a LIN transceiver. Such components may function using a lower power and may be fitted with an independent battery and/or wireless transceiver. In such cases, the system may include a cradle or other suitable recharging means to allow recharging, e.g., from the car battery or other source.

Figure 32:
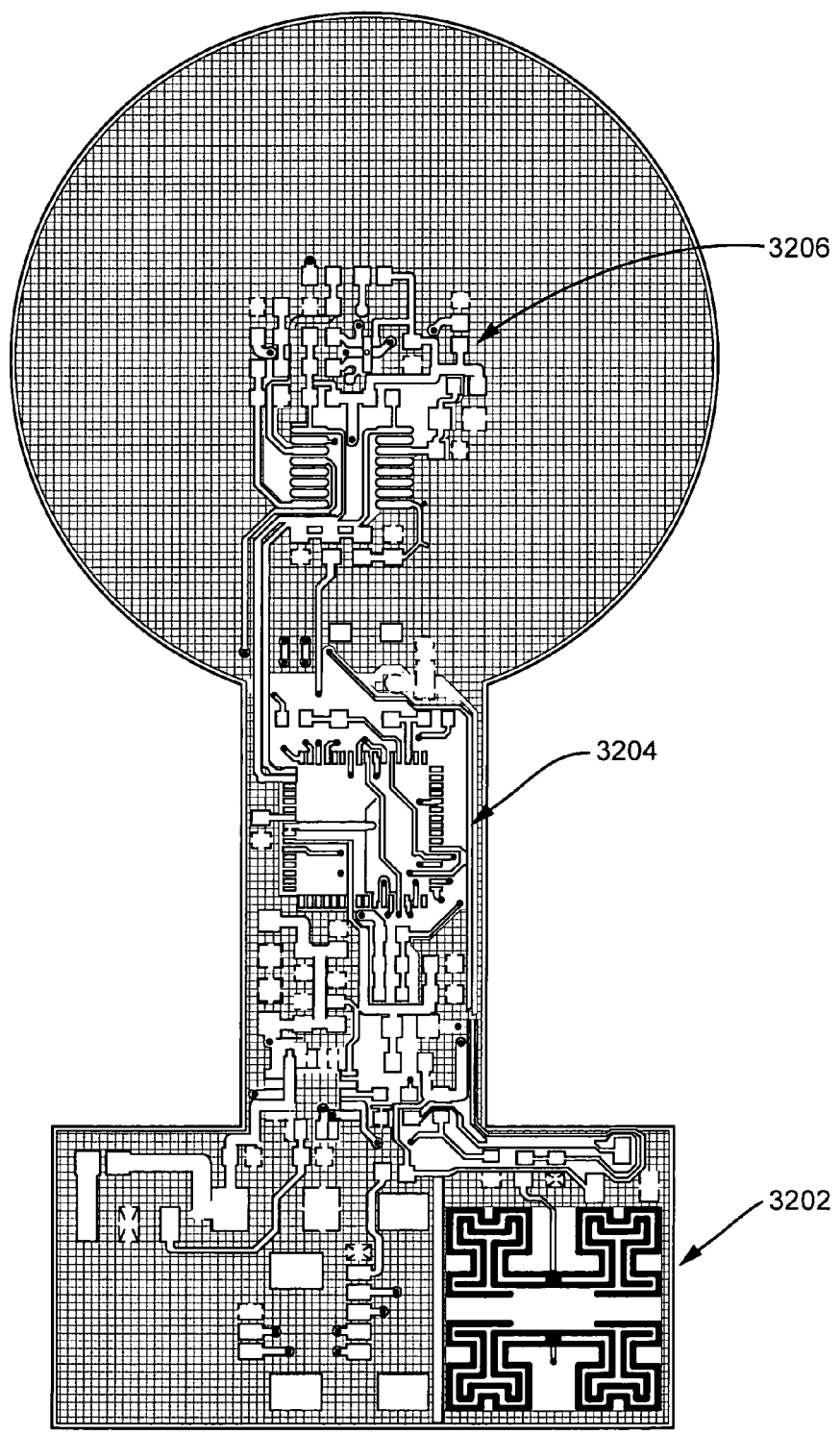
FIG. 32 shows an example first outer layer of a sensor according to an example embodiment.

FIGS. 32-35 show example layers comprising a PCB in accordance with an example embodiment. The PCB, as a whole, may be constructed from flex FR-4 or any suitable plastic, polyimide, polymer, etc., in certain non-limiting implementations. FIG. 32 shows an example first outer layer of a sensor according to an example embodiment. The first outer layer of FIG. 32 is designed to be located inside the car, on the side of the PCB closest to the driver. Thus, FIG. 32 includes an inside or "dry" capacitor array 3202, which may be formed in accordance with a fractal pattern in certain example embodiments. In certain example embodiments, multiple dry capacitor arrays 3202 may be formed on the first outer layer of FIG. 32, and/or the PCB of FIG. 32 may be connected to one or more "slave" PCBs in certain example embodiments. In the latter case, the slave boards may be tethered or wirelessly connected to the mater board. When slave boards are used, they may be attached to surface 4 of the glass directly or indirectly, e.g., to measure the humidity within the vehicle's cabin and/or moisture on the glass.

In either arrangement, the dry capacitor array(s) 3202 may be used to determine the presence of EMI and/or humidity (e.g., within the unit and/or car). EMI may be detected, for example, when the same or similar patterns are detected by both the wet and dry capacitor arrays at the same time or within a short predetermined time interval (e.g., within a few milliseconds or seconds or, more particularly, within about 20-40 ms), the wet and dry capacitor arrays being located on differing layers, and opposing sides, of the PCB. Connections 3204 are provided for a microprocessor (described in greater detail below). Connections 3206 also are provided for a sigma-delta converter/filter as described above.

One or more inner layers may be provided in certain example embodiments so as to provide shielding between the wet and dry capacitor arrays. This arrangement advantageously reduces the problems associated with some fields emanating outwardly and some fields emanating inwardly, which might cause spurious detections, measure the humidity within the vehicle when attempting to detect moisture outside the vehicle, etc. Thus, the one or more inner layers of certain example embodiments may help decouple the wet and dry capacitor arrays.

Figure 33:
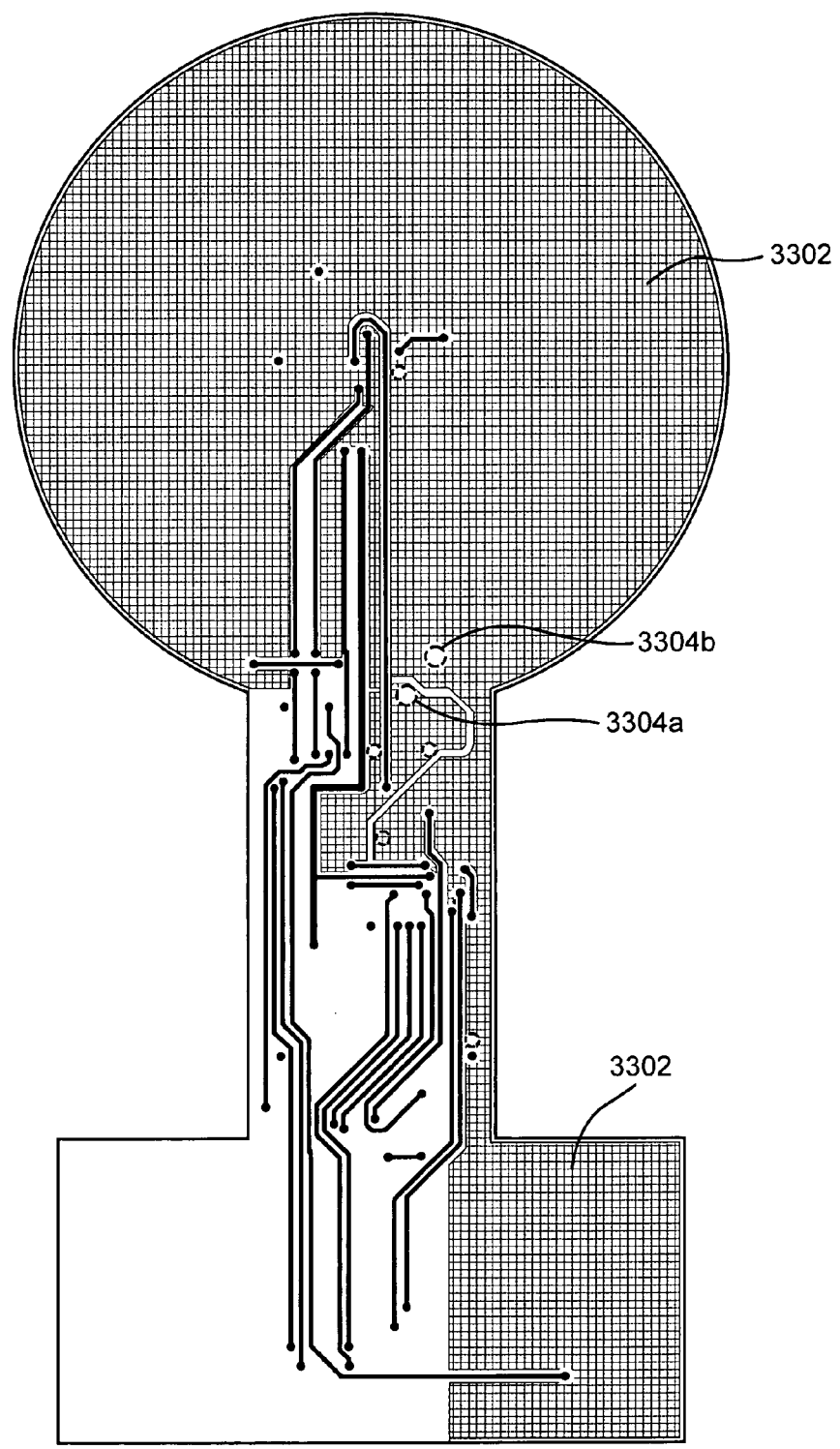
FIG. 33 shows an example first inner layer of a sensor according to an example embodiment.
Figure 34:
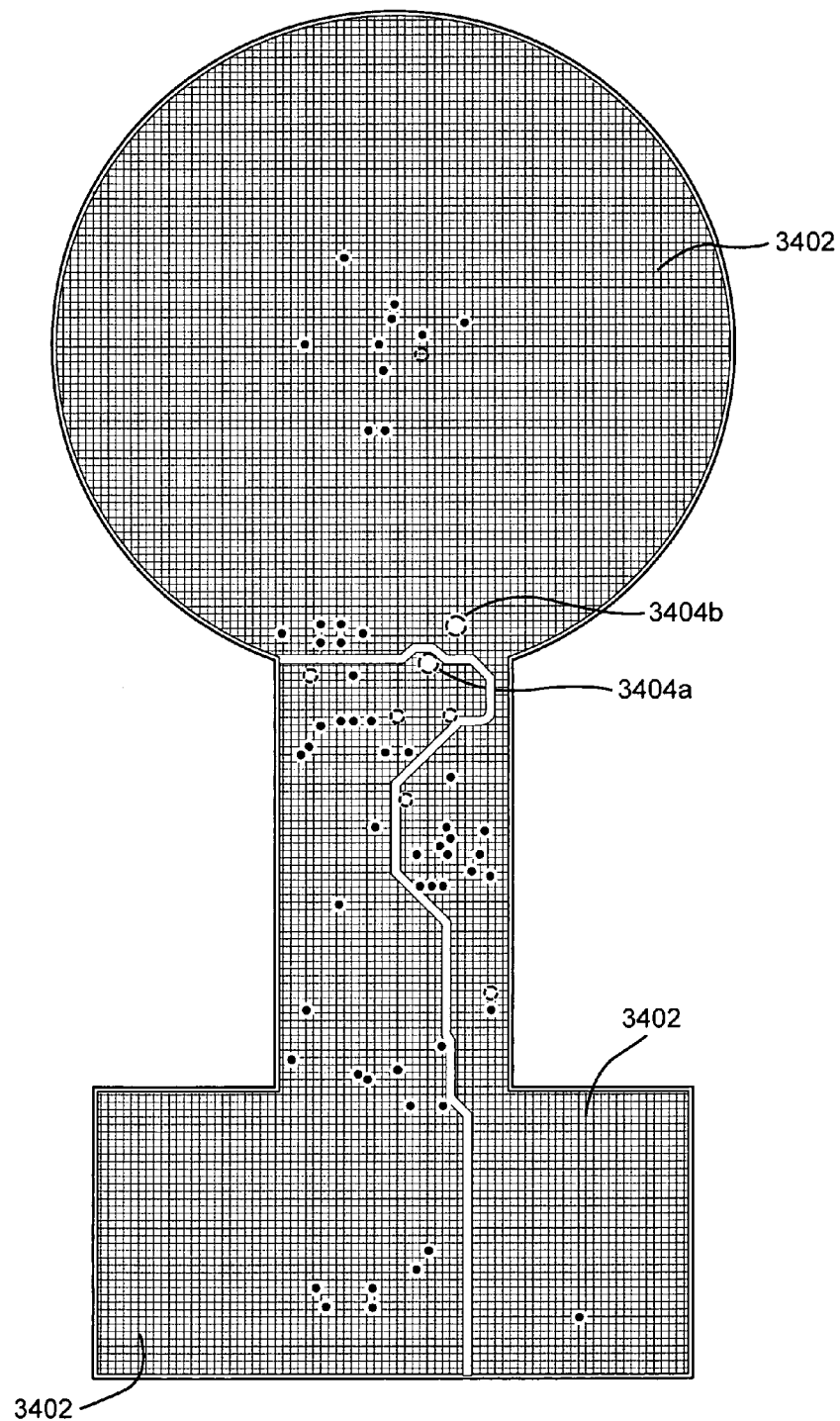
FIG. 34 shows an example second inner layer of a sensor according to an example embodiment.

As examples of the inner layers, FIG. 33 shows an example first inner layer of a sensor according to an example embodiment, and FIG. 34 shows an example second inner layer of a sensor according to an example embodiment. In FIG. 33, the majority of the layer is metallic 3302 (e.g., copper) and is at voltage potential. In addition to providing shielding, the metallic layer 3302 also makes it difficult for fields of the wet capacitor array to be coupled to the fields of the dry capacitor array, and vice versa. A number of conduits or lines connect between layers and also provide power to the chips. Digital and analog grounds 3304a, 3304b also are provided.

Figure 35:
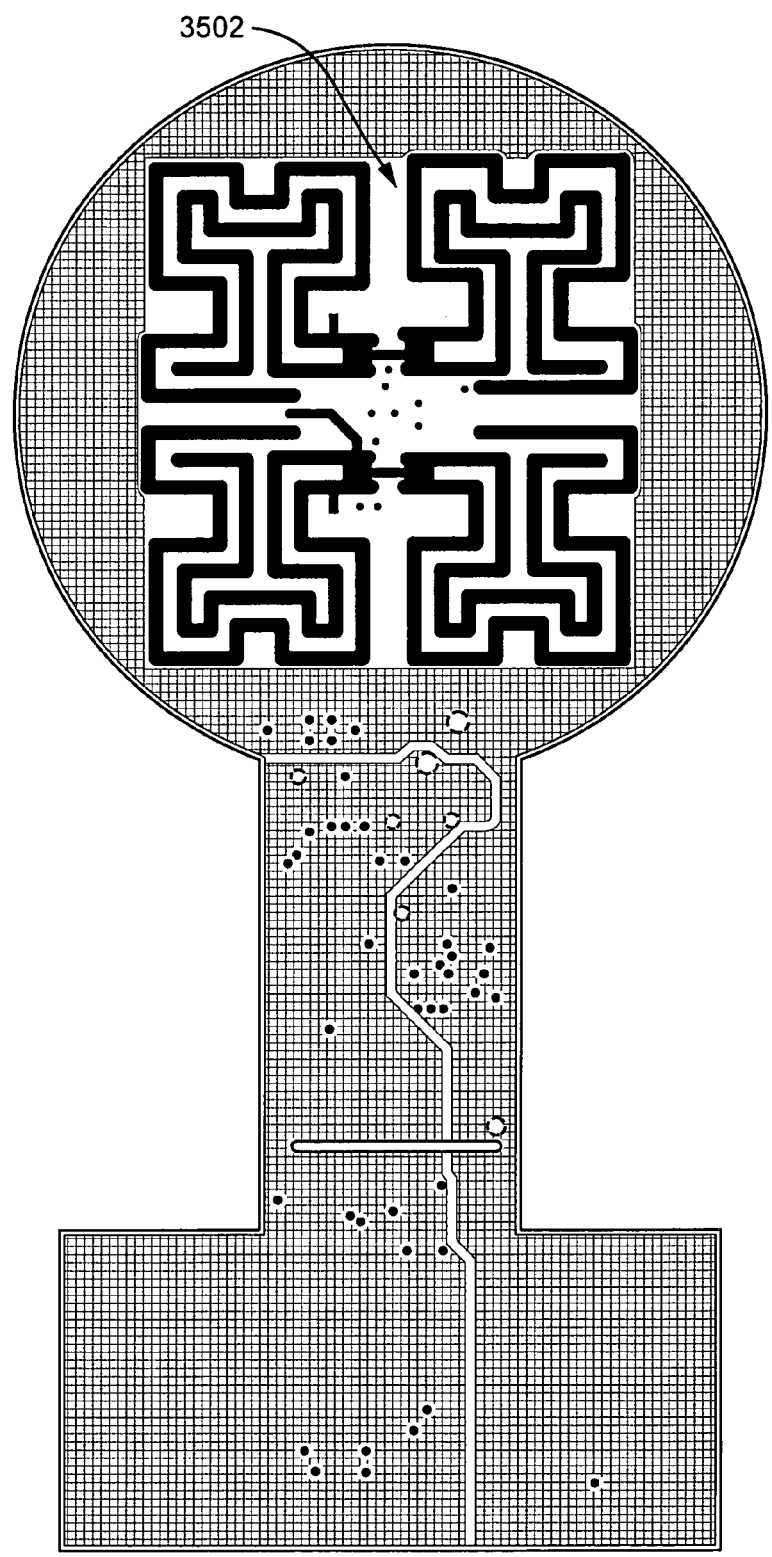
FIG. 35 shows an example second outer layer of a sensor according to an example embodiment.

The first inner layer shown in FIG. 33 is closer to the first outer layer shown in FIG. 32, whereas the second inner layer shown in FIG. 34 is closer to the second outer layer shown in FIG. 35. As above, the majority of the layer is metallic 3402 (e.g., copper), and digital and analog grounds 3404a, 3404b also are provided. As can be seen from FIGS. 33 and 34, the metallic, shielding portions are positioned on their respective layers so as to be at least adjacent to the wet and dry capacitor arrays, where the fields likely will be strongest.

FIG. 35 shows an example second outer layer of a sensor according to an example embodiment. The second outer layer of FIG. 35 is designed to be located inside the car, on the side of the PCB furthest from the driver and closest to the glass. Thus, FIG. 35 includes an outside or "wet" capacitor array 3502, which may be formed in accordance with a fractal pattern in certain example embodiments. The outside capacitance can be measured in a differential mode using Cin+ and Cin−, as well as in a single-ended mode in certain example embodiments. This may help reduce the signal to noise ratio considerably. Also, an RMS resolution of the system is above 16 bits in certain example implementations.

As noted above, one problem associated with current sensor technologies is a slight delamination or stress, or even improper installation, between the glass and sensor puts the optical system out of alignment. The bonding of certain example embodiments, however, helps reduce these and/or other precision alignment issues. In certain example embodiments, the PCB is attached to surface 4 of the windshield using an adhesive. For example, a double-sided adhesive tape may be used to secure the second outer layer to surface 4 of the windshield. In certain example embodiments, the PCB may be located behind the black frit printed on the glass. A double-sided adhesive tape advantageously may provide increased stability for the sensor (especially as compared to the pin design, which may allow for movement of the sensor and/or the individual pins directly and/or corrosion) while also substantially sealing it, reducing the chances of debris, moisture, and/or the like from coming into direct contact with the sensor and/or components thereof. In certain example embodiments, the glass and/or glass frit may be treated proximate to where the sensor is to be adhered, e.g., to facilitate the bonding process. For example, a silane-based precursor may be used to prepare the surface for adhesion. In certain example implementations, an adhesive tape commercially available from 3M such as VHB™ Adhesive Transfer Tapes with Adhesive 100MP (including F9460PC, F9469PC, and F9473PC) may be used to secure the PCB to the windshield. Of course, any suitable adhesive tape may be used in connection with certain example embodiments. An example of this arrangement is shown in FIG. 37(*a*).

In view of the above, it will be appreciated that the EM field lines for the outside capacitors in certain example embodiments probe only the outside of the car on the windshield surface and, on the inside, the outside capacitors' field lines are shunted via a "buried ground plane." Accordingly, its field lines do not probe inside the car or measure humidity from inside. The same rationale applies to the inside facing capacitors, as its field lines "see" the inside of the car. Free propagating EM waves (like EMI) can affect both sets of capacitors, and the occurrence of this event is indicative of an EMI event like a lightning strike. The inside array of capacitors also is able to pick up subtle changes in capacitance that relate to humidity level. It will be appreciated that the inclusion of a temperature sensor on the PCB set next to the inside capacitors enables the dew point to be accurately deduced.

Figure 36:
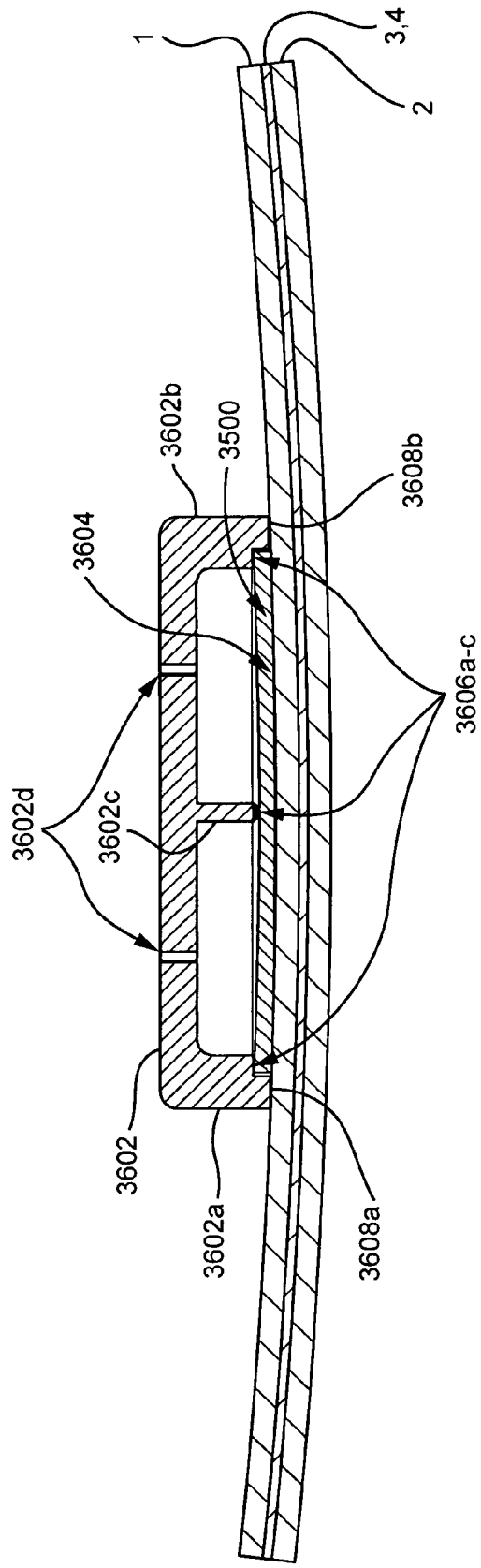
FIG. 36 is a cross-sectional view of an example PCB cover according to an example embodiment.
Figure 37A:
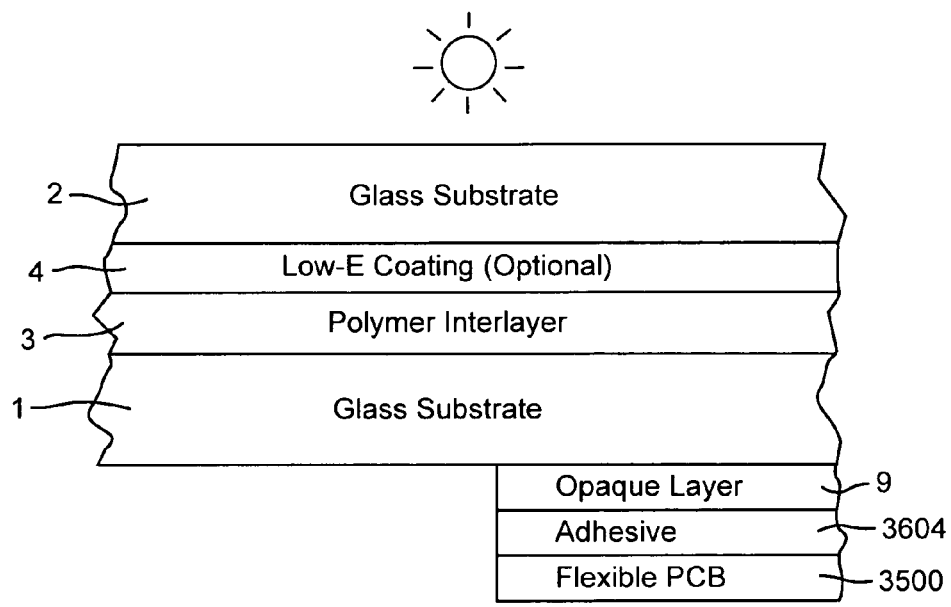
FIG. 37(a) is a cross-sectional view of a rain sensor supported by an interior surface of an inner glass substrate according to an example embodiment of this invention.
Figure 37B:
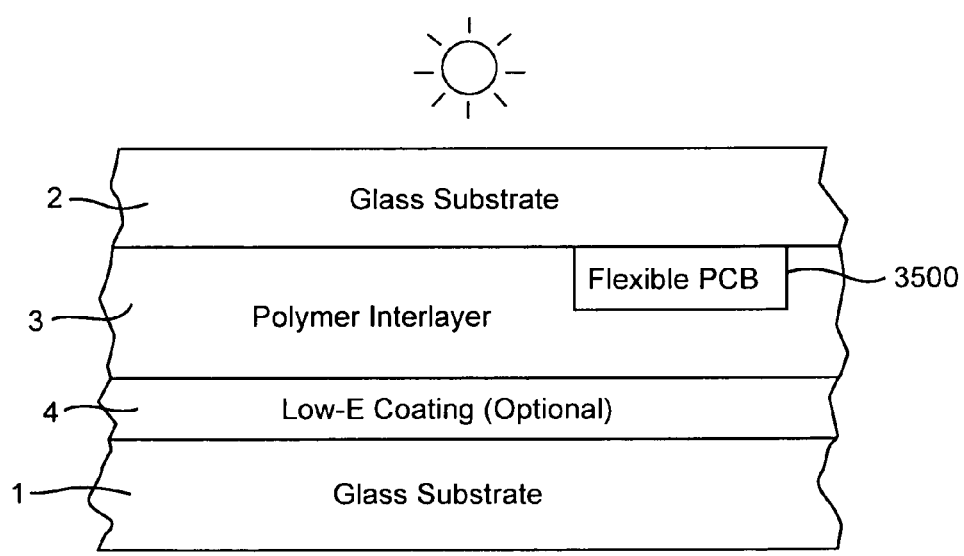
FIG. 37(b) is a cross-sectional view of a rain sensor supported by an interior surface of an outer glass substrate according to an example embodiment of this invention.
Figure 37C:
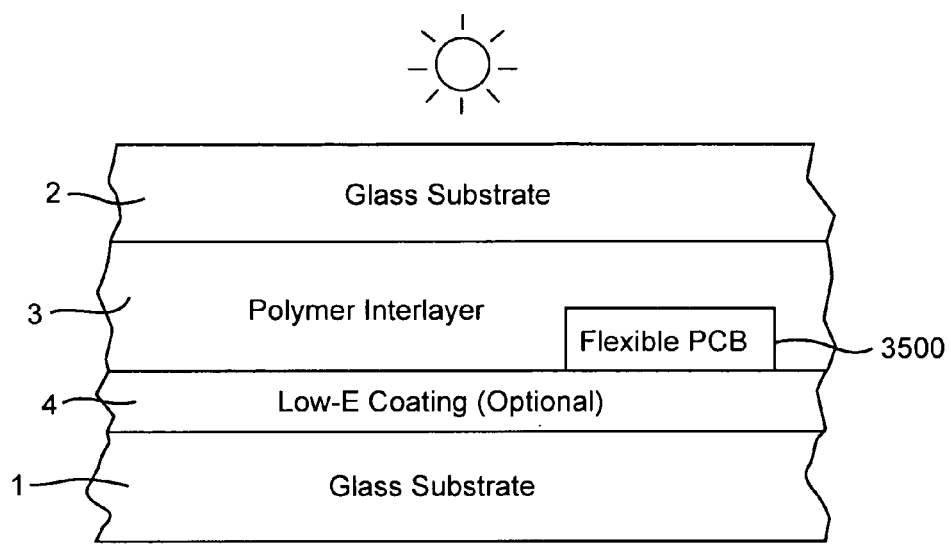
FIG. 37(c) is a cross-sectional view of a rain sensor supported by an outer surface of an inner glass substrate according to an example embodiment of this invention.
Figure 37D:
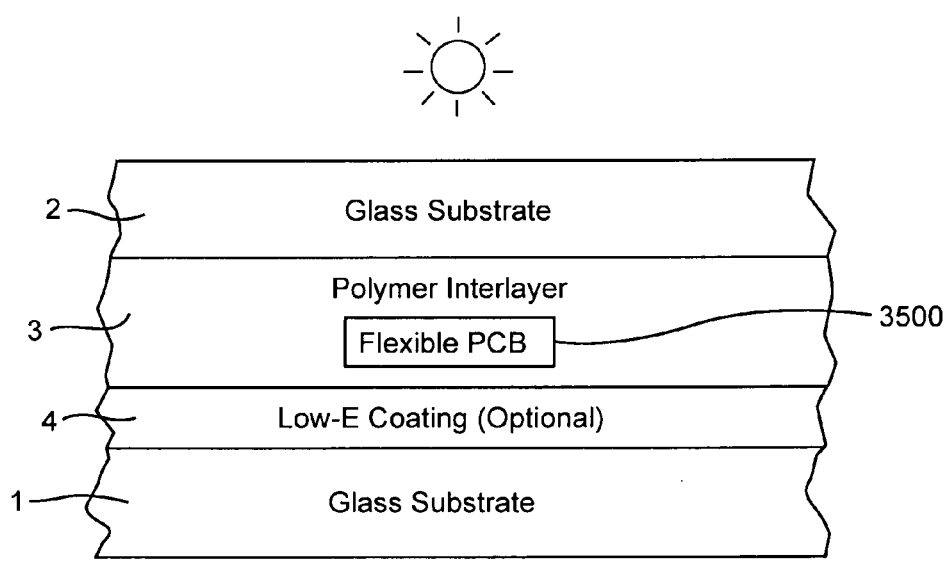
FIG. 37(d) is a cross-sectional view of a rain sensor embedded in a polymer interlayer according to an example embodiment of this invention.

FIG. 36 is a cross-sectional view of an example PCB cover 3602 according to an example embodiment. The cover 3602 protects the PCB 3500, which is adhered to surface 4 of the inner glass substrate 1 of the windshield. The cover 3602 is substantially M-shaped when viewed in cross-section. As such, the cover 3602 includes a plurality of legs. In the example shown in FIG. 36, three such legs 3602*a-c* are shown, with left and right legs 3602*a*, 3602*b*, and a center leg 3602*c*. The left and right legs 3602*a*, 3602*b* are notched out so as to contact both surface 4 of the windshield and the PCB 1500. Soft plastic pieces 3606*a-c* may be added to the cover 3602 at the notched out portions of the left and right legs 3602*a*, 3602*b*, as well as at surface of the center leg 3602*c* that comes into contact with the PCB 1500, so as to hold the PCB in place while reducing the chances of damaging it. The portions of the left and right legs 3602*a*, 3602*b* that are not notched out may be adhered to surface 4 of the windshield using the adhesive tape 3604 that also serves to bond the PCB 1500 to surface 4 of the windshield. Alternatively or in addition, beads 3608*a-b* or other suitable fastening mechanisms may be used to bond the portions of the left and right legs 3602*a*, 3602*b* that are not notched out to surface 4 of the windshield. Because the PCB 1500 and/or components thereon may produce heat, one or more ventilation slots 3602*d* or through-holes may be provided to the cover 3602 so as to allow the heat to dissipate. Although not shown in FIG. 36, the cover 3602 may substantially fully enclose the PCB 1500.

In certain example embodiments, the rain sensor also may be supported by surface 2 as the example in FIG. 37(*b*) shows, surface 3 as the example in FIG. 37(*c*) shows, or in the polymer-inclusive layer between surfaces 2 and 3 as the example in FIG. 37(*d*) shows. In such example implementations, a flexible PCB may be assembled in accordance with the above-described techniques. The flexible PCB or layers of the flexible PCB may be embedded in or formed from a polymer or acrylic (including, for example, PET). In certain example embodiments, connecting wires (e.g., for power, transmission of data, etc.) may extend from the PCB in a mesh, which is also flexible. Alternatively, in certain example embodiments, the wires may be replaced by ITO or other suitable leads printed on the glass, thereby possibly providing a more transparent or cleaner arrangement. In either case, the "leads" may be connected to a bus.

The PCB may be located in an area generally not visible from the interior or exterior of the car. Thus, in certain example embodiments, the PCB may be located, for example, proximate to the rear view mirror. Optionally, the PCB may be further obscured from sight via a black protective coating, which may be printed on or formed around the PCB in the case that the windshield is not protected, or may be a black frit of the windshield itself. In addition to concealing the PCB from ordinary view, such a protective cover also may help to protect the PCB and/or its components from UV radiation. Furthermore, in certain example embodiments, the rain sensor and PCB may be sandwiched between surfaces 2 and 3 during lamination. Locating the rain sensor and PCB here also may help protect the rain sensor components from UV radiation by virtue of the material comprising the laminating layer (e.g., the PVB). An IR reflecting layer may still be coated on surface 3 of the windshield.

The rain sensor, flexible PCB, and leads all may be flexible. As above, this configuration advantageously may enable the rain sensor to conform to the shape of the windshield and also increase resiliency. Although slight deformation of the rain sensor, flexible PCB, leads, and/or components thereof may occur, e.g., by forces generated during lamination, heat, etc., baseline data may be collected after such processes (e.g., after lamination, etc.) so that the rain sensor algorithms are calibrated to take into account such changes. Also advantageous is the fact that the location and structure of the rain sensor, flexible PCB, and leads are unitized, thereby reducing the impact of shocks, vibrations, moisture, debris, etc.

Figure 38:
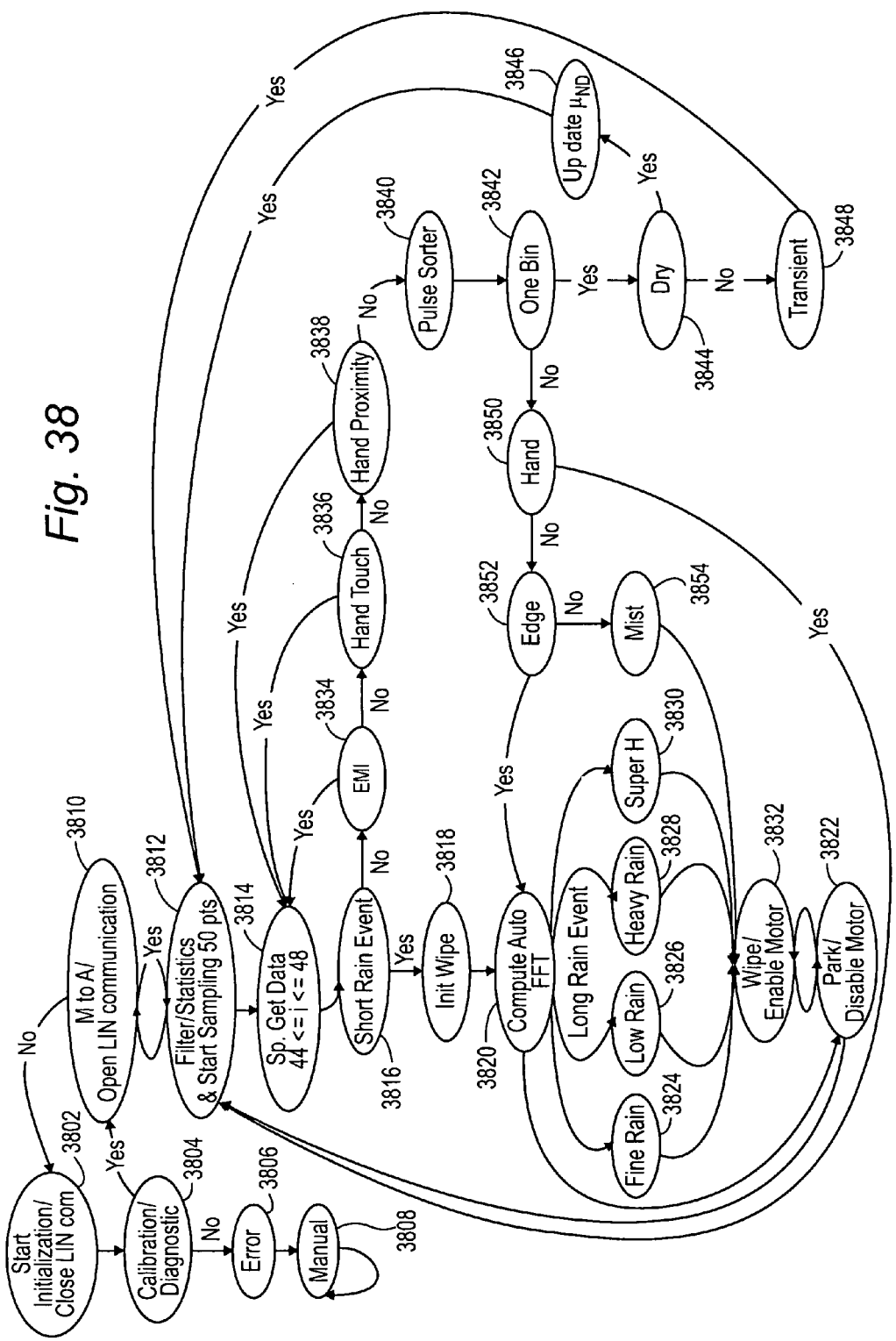
FIG. 38 is an exemplary flowchart or state diagram showing how windshield wipers may be actuated in accordance with an example embodiment.

FIG. 38 is an exemplary flowchart or state diagram showing how windshield wipers may be actuated in accordance with an example embodiment. In 3802, the system is started or initialized. If a communication to the LIN bus is already open, it is closed and/or reset. In 3804, the rain sensor including its capacitive arrays are calibrated or put into a diagnostic mode. This may enable baseline data to be gathered. If the calibration or diagnostic step fails in 3804, an error is generated in 3806 and the system is put into manual mode 3808. Alternatively, a user may initially put the system into manual mode 3808.

After calibrations are complete in 3804, LIN communication is opened in 3810. Filtering and/or statistics are applied in 3812 to a first buffer, which is filled over a first sampling interval. For example, 50 data points may be gathered over a predetermined time interval. A second buffer is filled with data from the first buffer in 3814. The second buffer may take only a subset of the data in the first buffer for analysis. For example, it may draw only the 44th through 48th data points.

Using the data in the first and/or second buffers, the system determines if there has been a short rain event in 3816. Here, as below, the determination of the existence of a perturbation (e.g., moisture, debris, etc.) may be determined using the techniques set forth above, including the matching of the signals from the capacitive arrays to predefined waveforms, performing auto- and/or cross-correlations, etc.

If a short rain event is detected in 3816, then a wipe is performed in 3818. The system may further classify the type of rain or moisture on the windshield and take further action appropriate for the type of rain. Thus, in 3820, a transform (e.g., a Fast Fourier Transform or FFT) is performed on the data. Then using the transformed data, the rain is classified as being one of a fine rain (e.g., something more than a fine mist) 3824, a low amount of rain 382, a heavy rain 3828, or super-hydrophylic rain 3830 (e.g., which tends to overwhelm the windshield). The wipers may be actuated or enabled in 3832 at a speed appropriate for the type of rain. They optionally may be temporarily parked or disabled in 3822 (which also may performed if the data cannot be transformed in 3820, or if the transformed data does not match a known rain pattern. The system may then return to 3812 to re-populate the first buffer, etc.

If a short rain event is not detected in 3816, the system determines whether EMI has affected the capacitive array(s) in 3834. If not, the system determines whether a hand touching the windshield has affected the capacitive array(s) in 3836. If not, the system similarly determines whether a hand (or other living or non-living article) coming into proximity with the windshield has affected the capacitive array(s) in 3838. If so in any of 3834, 3836, and 3836, the system returns to 3814 to re-populate the second buffer.

If no effects are attributable to EMI, a hand touch, or a hand coming into proximity with the windshield, a pulse sorter arranges the data from the first buffer in 3840. If the pulse-sorted data from 3840 fits into one bin as determined in step 3842 (e.g., there are no "edges" detected and thus the data is differentiable at all points), then the system determines whether the window is dry in 3844. If it is not, then there has been a transient change in capacitance 3848, which may be caused by, for example, a change in exposure to sun, wind, etc. In such a case, the system returns to 3812. If, however, the result of 3844 is different, the average baseline values for the capacitive arrays are updated in 3846, and the system returns to 3812. In this latter case, the system effectively may "learn" about the conditions and improve the accuracy of wipes.

If there is not one bin detected in 3842, the existence of a hand on the windshield is again determined in 3850. If a hand touch has been detected, the system returns to 3812. In 3852, the presence of any edges at all is determined. If there are any edges, then the system proceeds to 3820 to indicate that there is some kind of rain event other than a short rain event. If there are not any edges, then there is a mist 3854, and the motor is enabled and/or wipes commence in 3832.

As such, a feature of certain example embodiments is that the rain sensing code may perform an automatic normalization of the capacitance values. Over the course of day (even without water), the capacitance can change from about 0.6 pF to about 1 pF. This may be attributed to glass temperature changes. Certain prior art techniques simply try to subtract two signals, making the assumption that the difference does not vary with temperature. In fact, it has been determined that this is not correct. The normalization procedure of certain example embodiments helps ensure that sensing parameters do not have to change. There is nothing to calibrate, as the value is normalized by the mean. Accordingly, each time the rain sensing code goes through the "dry mode" on the state diagram, the normalization process occurs.

Certain example embodiments relate to light sensors. The light sensors may be mounted to the flexible PCBs described above. The connection of the light sensor to the flexible PCB may be accomplished using a flip-chip, wherein the light sensor is mounted to the back surface of the PCB (e.g., the surface of the PCB that faces away from the vehicle exterior). In general, flip-chip mounting is one type of mounting used for semiconductor devices, such as integrated circuit (IC) chips, which reduces the need for wire bonds. The final wafer processing step deposits solder bumps on chip pads, which connect directly to the associated external circuitry. The processing of a flip-chip is similar to conventional IC fabrication. Near the end of the process of manufacturing a flip-chip, attachment pads are metalized to make them more suitable for soldering. This metalizing typically includes several treatments. A small solder dot is deposited on each of the pads. The chips are cut out of the wafer, as conventional. Additional processing generally is not required, and generally there is no mechanical carrier at all. When a flip-chip is attached to a circuit, it is inverted to bring the solder dots down onto connectors on the underlying electronics or circuit board. The solder is then re-melted to produce an electrical connection. This leaves a small space between the chip's circuitry and the underlying mounting. In most cases an electrically-insulating adhesive is then used to provide a stronger mechanical connection, provide a heat bridge, and to ensure the solder joints are not stressed due to differential heating of the chip and the rest of the system. The resulting completed assembly is much smaller than a traditional carrier-based system. The chip sits on the circuit board, and is much smaller than the carrier both in area and height.

The light sensor of certain example embodiments "sees" through a small hole (e.g., a pinhole) or slit. The small hole extends through a black frit or opaque layer (when such a layer is provided) and through the PCB. A pinhole design allows the light sensor of certain example embodiments to "see" what is in the line of view. It also acts as a form of lens in and of itself. Thus, in certain example embodiments, the need for a lens may be reduced and sometimes even completely eliminated. This is a change from conventional light sensor designs, which typically require such lenses. When an opaque layer is implemented, including only a small pinhole therein advantageously may shield and/or protect the non-light sensing components of the PCB, e.g., from UV, and/or effectively hide such components from a driver's field of vision.

Although certain example embodiments do not require a lens, in certain other example embodiments, a lens may be used in connection with the light sensor. In such a case, the lens may be a substantially flat, defractive lens. Such a substantially flat, defractive lens may be located over the light sensor (or light sensing arrays of the light sensor described in greater detail below).

The light sensor of certain example embodiments may be able to detect the presence of light and/or the amount of lux. This may be possible over the UV, IR, and visible light spectra. As such, the light sensor of certain example embodiments may detect the presence and amount of lux UV, IR, and visible light within a line of sight from the vehicle. Optionally, the same and/or similar measurements may be taken from within the vehicle. The internally oriented arrays of the light sensor of certain example embodiments may be used for baseline comparisons of changes in ambient light. For example, in certain example embodiments, the internally oriented arrays of the light sensor may be compared with the externally oriented arrays so as to determine when the vehicle is within a tunnel, for example. Similarly, at least some of the externally oriented arrays may be pointed towards the sky for baseline purposes (e.g., to determine whether the vehicle is under cloud cover).

Figure 39:
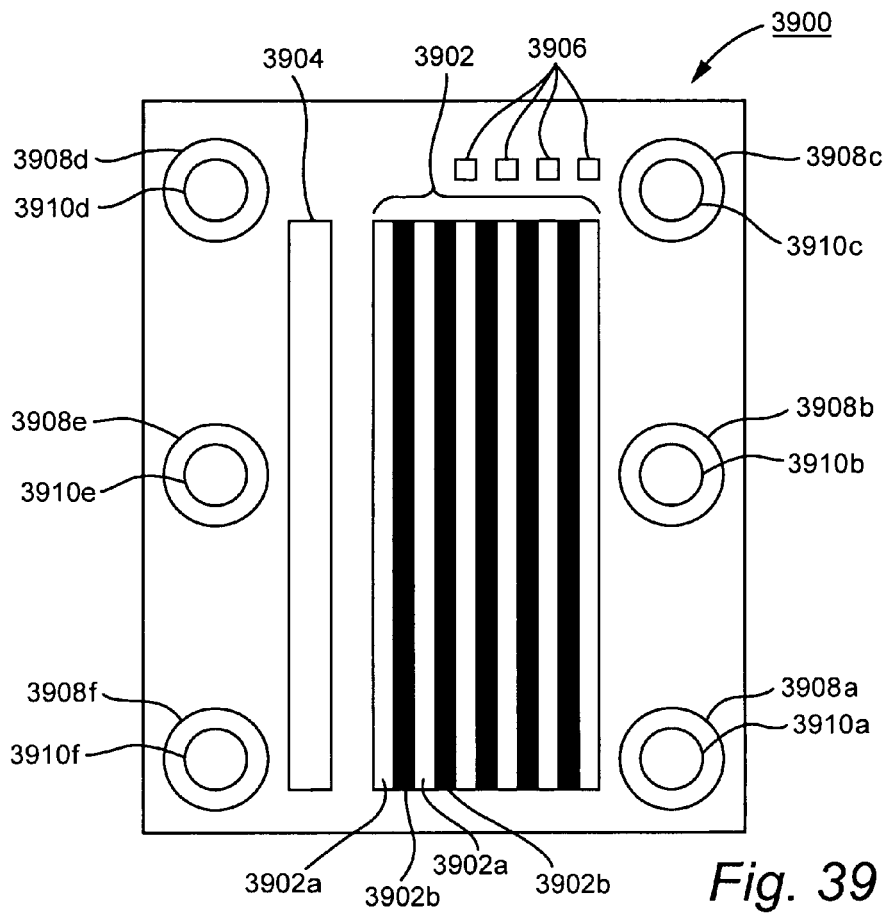
FIG. 39 is an illustrative view of a light sensor flip-chip design in accordance with an example embodiment.
Figure 43:
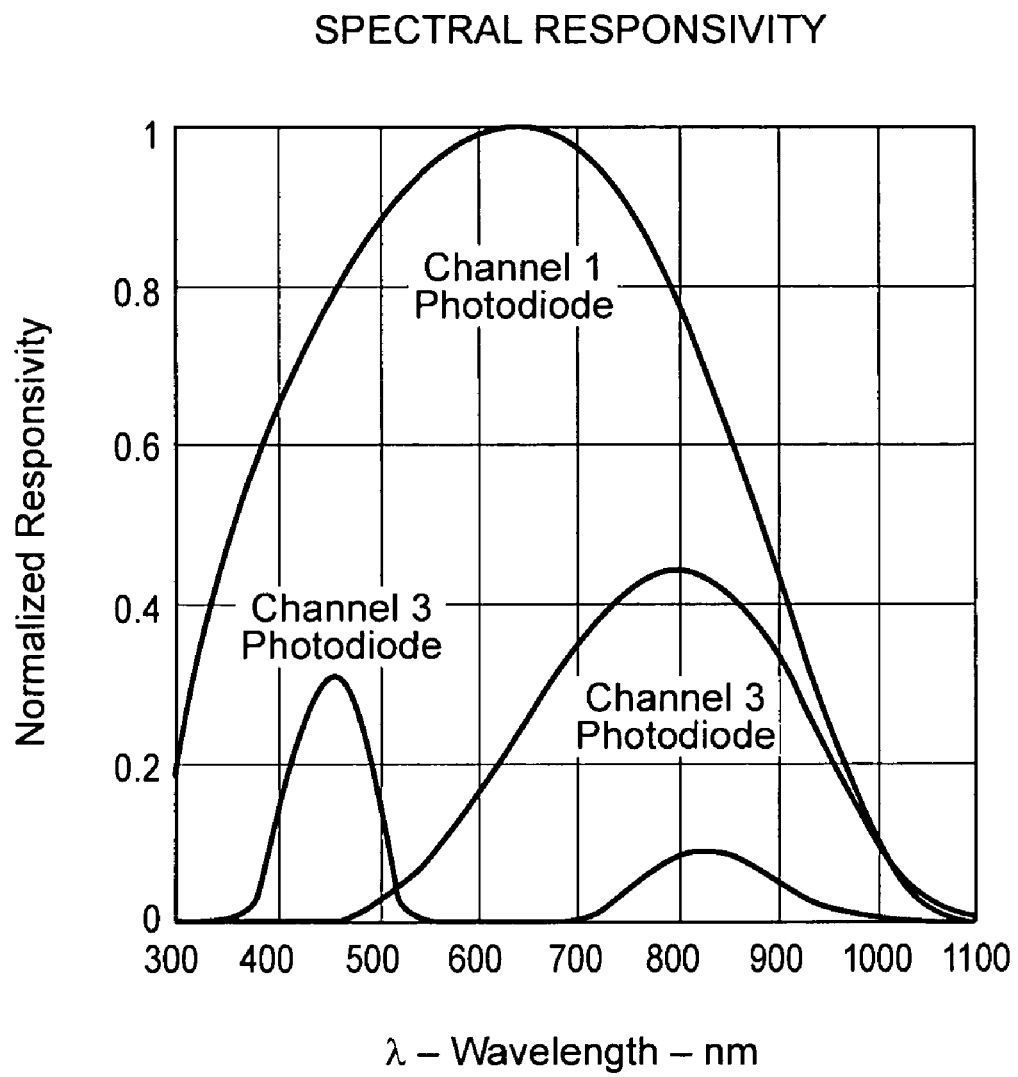
FIG. 43 is a graph showing the spectral responsivity of the photodiodes of the three channels of an illustrative light sensor according to an example embodiment.

FIG. 39 is an illustrative view of a light sensor flip-chip design 3900 in accordance with an example embodiment. A first array 3902 is provided. The first array 3902 includes bare silicon die 3902a in this photo-diode, and each silicon die is surrounded or covered by metal 3902b. In certain example embodiments, the metal 3902b may be used to generate baseline data in certain example embodiments. This first array 3902 may be multiplexed so as to "see" light in a broadband of from about 300 nm to about 1100 nm (and therefore including UV, visible and IR light), with responsivity peaking at about 650 nm, on a first channel, as well as on a third channel "seeing" light from about 400 nm to about 550 nm and peaking at about 500 nm (and thus "seeing" visible light). A second array 3904 may "see" light on a second channel, ranging from about 500 nm to about 1100 nm and peaking at about 800 nm (and thus "seeing" IR light). FIG. 43 is a graph showing the spectral responsivity of the photodiodes of the three channels of an illustrative light sensor according to an example embodiment. The channels may be digital or analog channels in certain example embodiments, and in certain example embodiments, one or more processing registers 3906 or other memory locations may be used to help buffer, convert, or otherwise process light-related data. One or more separate analog-to-digital converters also may be provided.

No lens is shown in FIG. 39. This is because, as noted above, a pinhole and proximity of the sensor to the pinhole may render a lens optional. Of course, in certain example embodiments, a lens may be provided. As noted above, the lens may be a defractive index lens. The light sensor of certain example embodiments may have a frontal field of view of from about 50-70°, more preferably from about 55-65°, and still more preferably of about 60°, the angles being on either side of normal or being total visible angles.

A plurality of legs 3908a-f are provided. Each of the legs 3908a-f has a solder connection pin 3910a-f respectively associated therewith. In certain example embodiments, the legs 3908a-f may be made of ceramic or glass, and the solder connection pins 3910a-f may include metal. In certain example implementations, the pins 3910a-f may correspond to voltage or power supply, address, ground supply, clock, interrupt, and data pins. Of course, it is possible to use other pins alone or in combination with such arrangements. An interrupt function optionally may facilitate the capture of only large changes so as to help reduce the wasting of memory.

The light sensor may be convert light intensity to a digital signal output, which may be sent to an I²C link of a vehicle for processing by suitable programmed logic circuitry (which may be any suitable combination of hardware, software, firmware, and/or the like). Channels 1 and 2 described above optionally may be "muxed" together to derive UV channel data. Upon completion of the conversion from analog to digital signals, the conversion results may be sent across their respective channels. The transfers may be double-buffered to maintain data integrity.

Light sensors may be obtained and modified from commercial sources so as to function with certain example embodiments. For example, light sensors commercially available from TAOS (e.g., modified ALS FlipChip models TSL2560FC and TSL2561FC), Micron, and/or other sources, may be used.

Figure 40:
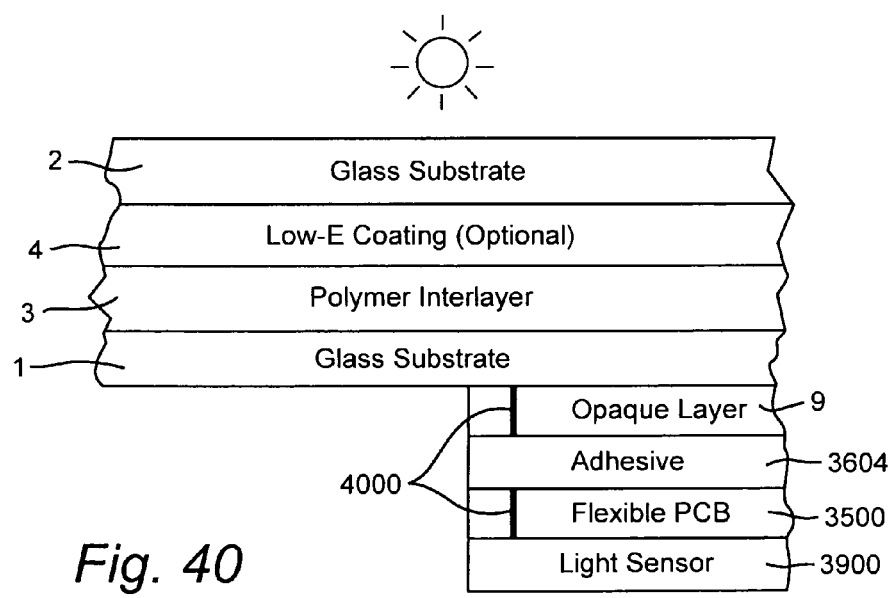
FIG. 40 is a cross-sectional view of a light sensor supported by an inner surface of an inner glass substrate according to an example embodiment of this invention.

FIG. 40 is a cross-sectional view of a light sensor supported by an inner surface of an inner glass substrate according to an example embodiment of this invention. Similar to the example embodiment shown in FIG. 37(a), in FIG. 40, a flexible PCB 3500 is connected to an opaque layer 9 via an adhesive 3604. The opaque layer is formed on an interior surface (e.g., a surface closest to the vehicle interior) of an inner glass substrate 1. The inner glass substrate 1 and the outer glass substrate 2 are laminated together via a polymer interlayer 3 (e.g., of PVB, EVA, etc.). A low-E coating 4 optionally may be applied to one or more of the interior surfaces of the substrates 1, 2. A hole 4000 is formed in the opaque layer 9 and the flexible PCB 3500. This hole 4000 may function as a lens, as described above. The light sensor 3900 is connected to the flexible PCB 3500 on a surface thereof that is closest to the vehicle interior using flip-chip mounting. Similar to above, the light sensor 3900 and flexible PCB 3500 may be mounted elsewhere in the windshield assembly (e.g., supported by surface 2 or 3, or floating within the polymer interlayer 3). An IR reflecting layer may or may not be deleted in certain example embodiments, e.g., depending on where the light sensor is located, the total effect of the IR reflecting layer, etc.

This example arrangement is advantageous for a number of reasons. For example, conventional light sensors typically include a plastic casing to protect the chips. Typical automotive testing requires functionality from about –40° C. to 105° C. The plastic casings protecting the chips in conventional design arrangements, however, have been found to melt at only about 85° C. This is troublesome, in that the glass substrates often reach temperatures of up to about 120° C. In contrast to typical designs, the design arrangement of certain example embodiments is stable up to at least about 120° C. This is true for several reasons. First, there is no plastic encasement to melt. Second, the chips and sensor itself are not in direct contact with the glass. That is, the ceramic legs and solder help insulate the chips from the heat. Additionally, the flexible circuit board (which may contain FR-4 and metal inner layers) may help deflect heat away from the light sensor.

The design arrangement of certain example embodiments also is advantageous, as water tends not to condense in front of or infiltrate the pinhole. This is because the arrangement of certain example embodiments may be protected by a substantially transparent adhesive (e.g., a tape and/or optional additional glue). Additionally, there is little movement because of the secure seal. Moreover, when there is movement, the entire PCB moves and thus baseline data may be maintained or recalculated.

Figure 41:
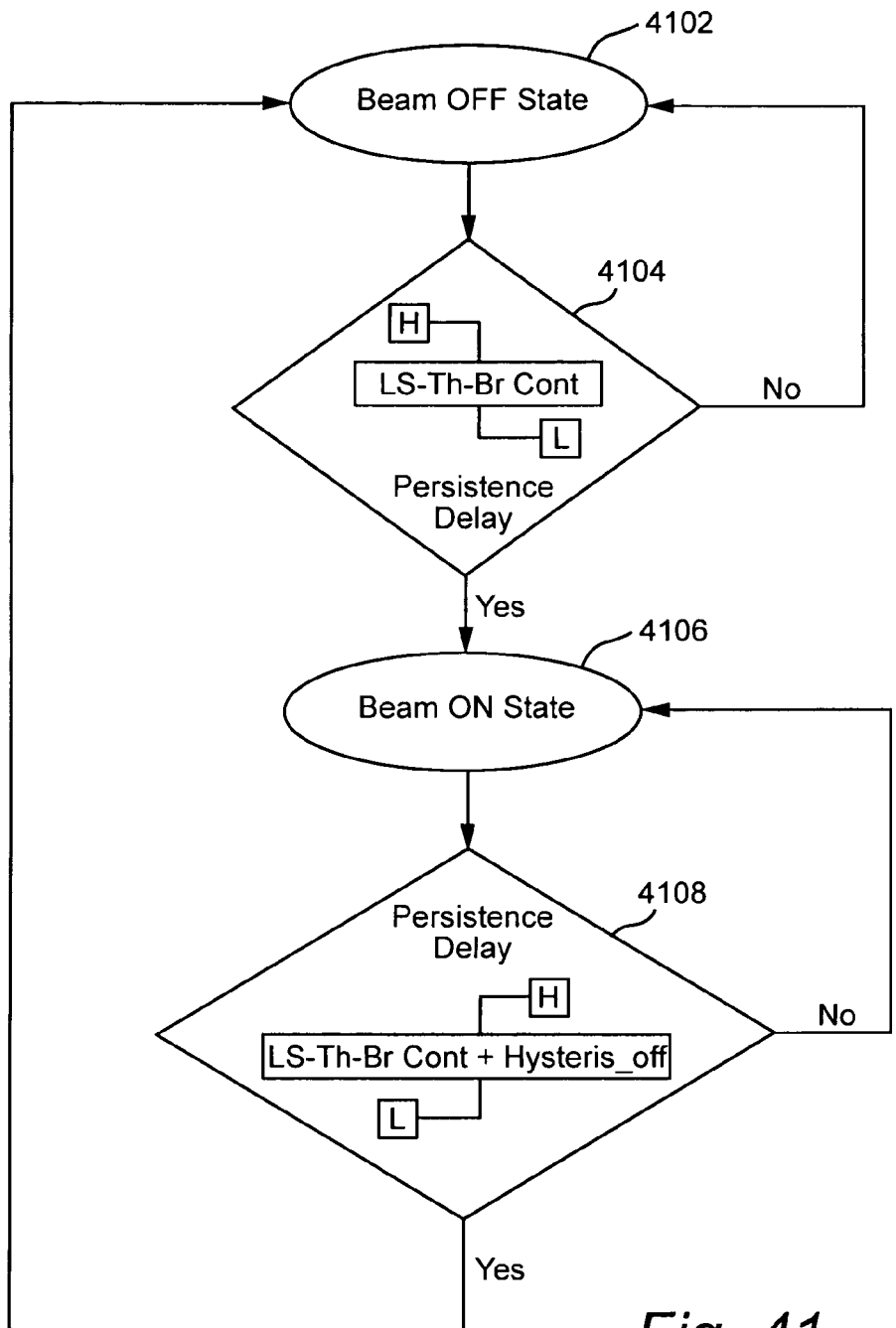
FIG. 41 is an illustrative flowchart or state diagram illustrating how lights may be turned on or off in dependence on data from the light sensor in accordance with an example embodiment.

Channel data from the light sensor may be compared to determine when and how to turn on/off the lights of a vehicle. The comparisons may be based on absolute values, ratios of channel outputs, etc. FIG. 41 is an illustrative flowchart or state diagram illustrating how lights may be turned on or off in dependence on data from the light sensor in accordance with an example embodiment. In FIG. 41, state 4102 represents a beam off state, and state 4106 represents a beam on state.

A FIFO buffer is built in certain example embodiments. In certain example embodiments, data for the buffer may be taken at a frequency of about 25 Hz, which generally is what is considered the rate at which the human eye sees. Of course, data may be sampled at other rates, which may be higher or lower than 25 Hz. A frame will comprise a predetermined number of points gathered at a predetermined interval. For example, frames may be captured at 25 Hz, with each frame including 50 points gathered at about every 40 ms. In certain example embodiments, the values from the buffer may or may not be filtered.

In essence, the light sensor may look for a stable edge change in the data in the buffer. If the edge change passes through a predefined threshold, the state should be switched. If the data is flat or substantially flat, there is no change in ambient light, and if the data does change but does not pass through a threshold, the states should not be switched.

Referring once again to FIG. 41, it is determined in decision 4104 whether the beams should be turned on, and it is determined in decision 4108 whether the beams should be turned off. LS-Th-Br-Cont is a light sensor threshold brightness control, which may be expressed in lux. A typical value for LS-Th-Br-Cont has been determined to be about 2,500 lux. H denotes a high level lux value, which has been determined to be about 4,000 lux or higher. L denotes a low level lux value, which has been determined to be about 1,000 lux or lower. Thus, if the signals pulled from the light sensor (e.g., in the buffer) pass from H to L through LS-Th-Br-Cont, the lights may be changed. The change to low may be required to persist for a predetermined time. This time may be the equivalent of one frame, a half frame, etc. Here, and below, the persistence delay may prevent flashes of light or transient changes in ambient light from erroneously triggering a change in state.

In decision 4108, a hysteresis factor is introduced. As such, Hysteris_Off has been determined to be about 5,000 lux. It is added to LS-Th-Br-Cont to determine when to toggle to another state. Thus, if the signals pulled from the light sensor (e.g., in the buffer) pass from L to H through the sum of Hysteris_Off and LS-Th-Br-Cont, and the persistence delay condition is met, then the state may be changed.

The above-described methodology has been determined to work particularly well when a vehicle is stationary or traveling below a certain critical speed. If, however, the vehicle meets or exceeds a certain speed threshold, denoted V-speed-th, then the LS-Th-Br-Cont may need to be incremented in certain example embodiments. For example, if the vehicle is traveling at a speed of about 100 km per hour or higher, the a delta of about 1,000 lux may be added to the LS-Th-Br-Cont. This delta will be added to the LS-Th-Br-Cont until the car falls below V-speed-th less a V-speed-hysteresis. In such a case, the delta may be returned to 0. A typical value for V-speed-hysteresis is about 30 km per hour.

This example technique may be used with a single channel. Alternatively, or in addition, this example technique may be further refined by comparing the data over the three channels listed above. In the simplest case, the threshold may be set using channel 1 (e.g., the broadband channel). Decisions about when to turn on light may be based on 2 or more of the channels. In a more complicated case, edges may be detected across all three channels. Thus, certain example embodiments involve edge detecting in space and time, as well as wavelength.

Indeed, changes in the channels may be correlated. Channels 1 and 2 vary linearly. Thus, if channels 1 and 2 change, then the light state should also be changed. This kind of change would suggest a big change in the visible, ambient light. If channel 1 changes but channel 2 does not change, there should be no change in state. This result is indicative of a change in the IR spectrum only. This may occur, for example, when clouds block the sun. If there is a change in channel 3 and not channel 2, there should be a change in state. This may occur, for example, when a car enters into a tunnel.

Figure 42:
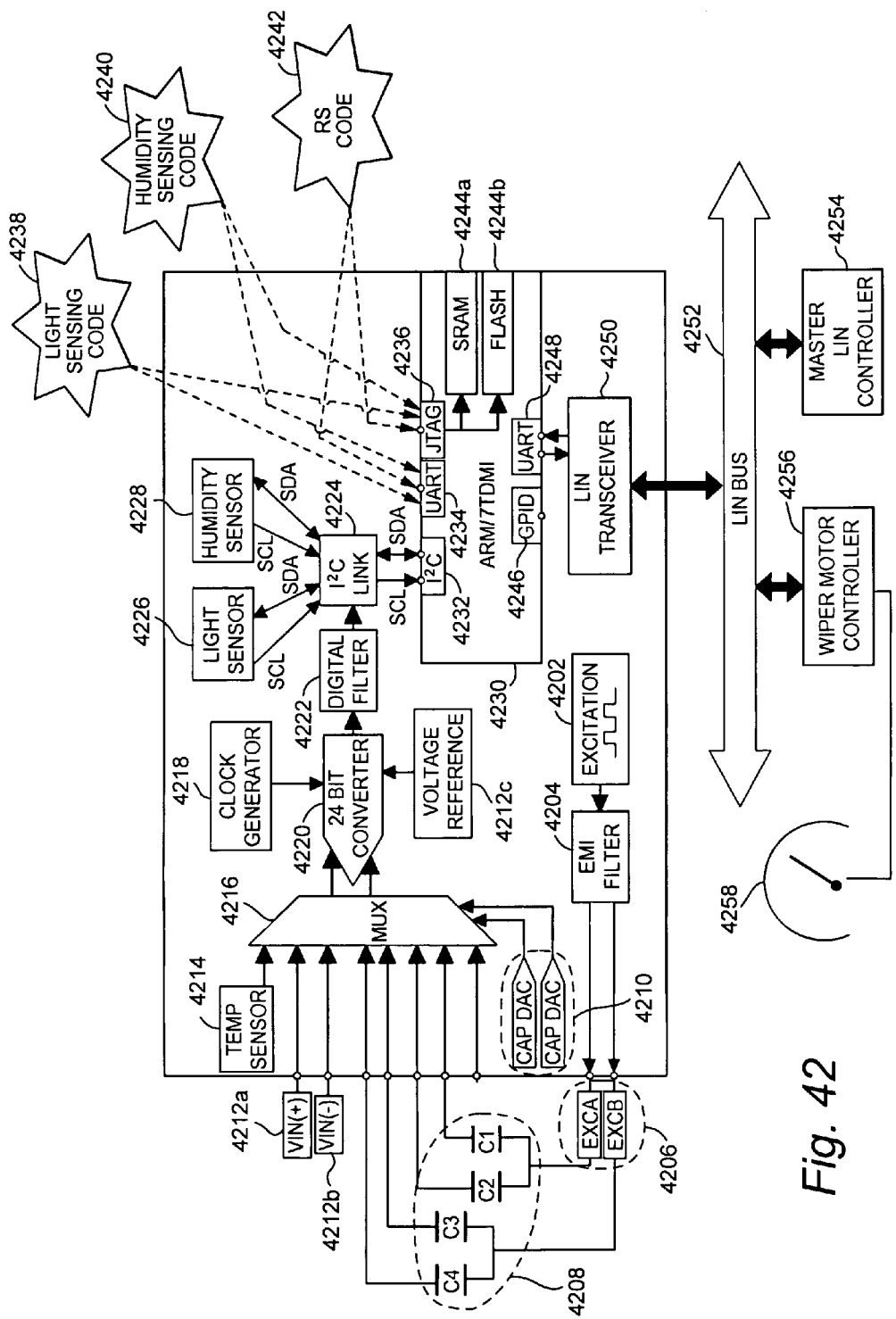
FIG. 42 shows example capacitive array circuitry according to an example embodiment.

FIG. 42 shows example capacitive array circuitry according to an example embodiment. In FIG. 42, excitations 4202 are filtered by an EMI filter 4204. Excitations signals EXC A and EXC B are processed by the capacitors in the capacitive array 4208. A multiplexer 4216 multiplexes the signals from the capacitive array 4208, capacitive digital-to-analog converters 4210, positive and negative voltage ins 4212a-b, and temperature sensor 4214. The multiplexed signal from multiplexer 4216 is fed into a 24-bit converter 4220, along with a clock signal generated by clock generator 4218 and a reference voltage 4212c. This signal is digitally filtered using a digital filter 4222 and fed into an I²C link 4224. Output from the light sensor 4226 and humidity sensor 4228 also are fed into the I²C link 4224.

The I²C link 4224 is connected to an I²C port 4232 of the processor 4230. Each of the light sensing code 4238, humidity sensing code 4240, and the rain sensor code 4242 are connected to first UART and JTAG ports 4234 and 4236 of the processor 4230. The codes may be implemented as programmed logic circuitry (e.g., any suitable combination of hardware, software, firmware, and/or the like), and/or may be tangibly stored as instructions on a computer-readable storage medium. The first JTAG port 4236 also is connected to one or more memory locations. The memory locations shown in the FIG. 42 example are SRAM and flash memory locations 4244a and 4244b. The processor 4230 also includes a GPID port 4246 and a second UART port 4248.

The second UART port 4248 is connected to a LIN transceiver 4250 which is ultimately connected to a central LIN bus 4252 of the vehicle. The LIN bus 4252 is connected to a master LIN controller 4254, as well as a wiper motor controller 4256. The wiper motor controller 4256 ultimately controls the wipers 4258 in dependence on the excitations 4202.

By way of example and without limitation, the AD7745 and AD7746 are a high resolution, $\Sigma$-$\Delta$ capacitance-to-digital converters that may be used in connection with certain example embodiments. Of course, it will be appreciated that other $\Sigma$-$\Delta$ capacitance-to-digital converters may be used in connection with certain example embodiments. Also by way of example and without limitation, the microprocessor may be an ADuC7128 microcontroller, which may be used in connection with an ARM7TDMI core. Of course, it will be appreciated that other microprocessors and/or microcontrollers may be used in connection with certain example embodiments.

It is noted that herein the use of the word "fractal" is not limited to a perfect fractal pattern, and instead also covers quasi-fractals such as the polygonal elements and geometric patterns having self-affinity such as those discussed for example in U.S. Pat. Nos. 6,809,692, 6,937,191, and/or 7,015,868 which are all incorporated herein by reference.

It is noted that while capacitors C1-Cn (where n is two, four, ten or any other suitable number) are preferred as the sensing devices in certain example embodiments of this invention, it is possible to use other types of sensing devices instead of or in addition to the capacitors in certain example instances.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A light sensor for a vehicle, comprising:
   a printed circuit board (PCB) to be supported by a vehicle window, the PCB comprising first and second outer layers and at least one inner layer, the first outer layer adapted to be closest to an interior of the vehicle and the second outer layer adapted to be closest to an exterior of the vehicle;
   a light sensor flip-chip mounted to an inner surface of the first outer layer of the PCB, the light sensor flip-chip including at least two light sensor arrays, each said sensor array being configured to sense light of a predetermined wavelength;
   programmed logic circuitry configured to set a state of the vehicle lights in dependence on the light sensor; and
   wherein the at least two light sensor arrays are arranged so as to receive radiation through at least one hole formed in the PCB, the hole in the PCB acting as a lens.

2. The light sensor of claim 1, further comprising first and second inner layers, the first and second inner layers being substantially metallic.

3. The light sensor of claim 1, wherein the first and second outer layers are formed from a flexible polymer.

4. The light sensor of claim 1, wherein the light sensor is bonded to the vehicle window via an adhesive tape, and wherein the light sensor is supported by an interior surface of the vehicle window.

5. The light sensor of claim 1, wherein an opaque layer is provided on the window so as to shield the PCB from a view of a passenger inside the vehicle.

6. The light sensor of claim 1, wherein the opaque layer is a black frit and wherein a hole is formed in the black frit so as to correspond with the hole formed in the PCB.

7. The light sensor of claim 1, wherein the window is one of a vehicle windshield, a vehicle backlite, and/or a vehicle sunroof.

8. The light sensor of claim 1, further comprising a plurality of ceramic legs formed on the light sensor flip-chip that include solder connection pins for connecting the flip to the PCB.

9. The light sensor of claim 1, wherein light sensor operates free from any lenses apart from the hole in the PCB.

10. The light sensor of claim 1, wherein each said light sensor array is configured to sense a presence and intensity of light in a wavelength and to output the presence and intensity of light via a respective channel.

11. The light sensor of claim 10, wherein a first channel is a broadband channel, a second channel is an IR light channel, and a third channel is a visible light channel.

12. The light sensor of claim 10, further comprising channel analyzing means for determining whether to switch an on/off state of the vehicle lights.

13. The light sensor of claim 10, wherein the first array includes bare silicon covered by metal, the first array being configured to sense a presence and intensity of light in a broadband wavelength and in a visible light wavelength, and wherein the second array is configured to sense a presence and intensity of light in an IR wavelength.

14. The light sensor of claim 11, wherein the first channel operates over a wavelength range of about 300-1100 nm with a peak responsivity at about 650 nm, wherein the second channel operates over a wavelength range of about 500-1100 nm with a peak responsivity at about 800 nm, and wherein the third channel operates over a wavelength range of about 400-550 nm with a peak responsivity at about 500 nm.

15. The light sensor of claim 1, further comprising a refractive index lens.

16. A flexible printed circuit board (PCB) supported by a vehicle window, comprising:

a first outer layer, the first outer layer being closest to an interior of the vehicle and being formed from a flexible polymer;

a second outer layer, the second outer layer being closest to an exterior of the vehicle and being formed from a flexible polymer;

at least one substantially metallic inner layer;

a light sensor comprising a light sensor mounted to an inner surface of the first outer layer of the PCB, the light sensor including at least two light sensor arrays, each said sensor array being configured to sense light of a predetermined wavelength; and programmed logic circuitry configured to set a state of the vehicle lights in dependence on the light sensor, wherein the at least two light sensor arrays are arranged so as to see through a hole formed in the PCB, the hole in the PCB acting as a lens.

17. The PCB of claim 16, further comprising a plurality of ceramic legs formed on the light sensor flip-chip that include solder connection pins for connecting the flip to the PCB.

18. The PCB of claim 16, wherein light sensor operates free from any lenses apart from the hole in the PCB.

19. The PCB of claim 16, further comprising a plurality of light sensor arrays provided to the light sensor flip-chip, wherein each said light sensor array is configured to sense a presence and intensity of light in a wavelength and to output the presence and intensity of light via a respective channel.

20. A vehicle window, comprising:

first and second substantially parallel spaced-apart glass substrates laminated together via a polymer-inclusive layer;

an opaque layer;

a printed circuit board (PCB) including a light sensor comprising a light sensor flip-chip, the light sensor flip-chip including at least two light sensor arrays, each said sensor array being configured to sense light of a predetermined wavelength; and an adhesive for bonding the light sensor to the PCB, wherein a hole is formed in the PCB and the opaque layer so as to allow the light sensor arrays to see through the hole formed in the PCB and the opaque layer, wherein a state of the vehicle lights is settable in dependence on the light sensor, and wherein the PCB is located in or is supported by the vehicle windshield.

21. The vehicle window of claim 20, wherein the light sensor of the PCB remains stable if the vehicle window or a component thereof reaches a temperature of about 120° C.

* * * * *